United States Patent [19]
Young et al.

[11] Patent Number: 6,153,740
[45] Date of Patent: Nov. 28, 2000

[54] CDNA ENCODING NUCLEOSIDE TRANSPORTER

[75] Inventors: James D. Young; Carol E. Cass, both of Edmonton, Canada

[73] Assignee: University of Alberta, Canada

[21] Appl. No.: 08/800,291

[22] Filed: Feb. 13, 1997

Related U.S. Application Data

[63] Continuation-in-part of application No. 08/499,314, Jul. 7, 1995, abandoned.
[51] Int. Cl.$^7$ ..................................................... C12N 15/12
[52] U.S. Cl. .................... 536/23.5; 435/69.1; 435/252.3; 435/320.1
[58] Field of Search ............................... 435/69.1, 252.3, 435/320.1; 536/23.5, 350

[56] References Cited

PUBLICATIONS

Huang et al., "Cloning and Functional Expression of a Complementary DNA Encoding a Mammalian Nucleoside Transport Protein", *The Journal of Biological Chemistry*, vol. 269, No. 27, Jul. 8, 1994 pp. 17757–17760.

Birnbaum et al. "Cloning and characterization of a cDNA encoding the rat brain glucose–transporter protein", P.N.A.S. 83:5784–5788, Aug. 1986.

Ramamoorthy et al. "Antidepressant– and cocaine–sensitive human serotonin transporter: Molecular cloning, expression, and chromosomal localization". P.N.A.S. 90:2542–2546, Mar. 1993.

Nelson et al. "Cloning of the human brain GABA transporter". FEBS Letters 269(1):181–184, Aug. 1990.

Bannon et al. "Dopamine transporter mRNA content in human substantia nigra decreases precipitously with age". P.N.A.S. 89:7095–7099, Aug. 1992.

Jhiang et al. "Cloning of the human taurine transporter and characterization of taurine uptake in thyroid cells". FEBS Letters 318(2):139–144, Mar. 1993.

Shashidharan et al. "Cloning and characterization of a glutamate transporter cDNA from human cerebellum". Bioch. et Biophys. acta 1216:161–164, Oct. 1993.

Kim et al. "Cloning of the Humen Glycine Transporter Type 1: Molecular and Pharmacological Characterizatyon of Novel Isoform Variants and Chromosomal Localization of the Gene in the Human and Mouse Genomes". Mol. Pharmocol. 45:608–617, Apr. 1994.

*Primary Examiner*—John Ulm
*Attorney, Agent, or Firm*—Fish & Richardson P.C.

[57] ABSTRACT

The invention features a method for identifying compositions which modulate the activity of a Na$^+$-dependent nucleoside transport polypeptide. This invention also features isolated DNA encoding the transport polypeptide, a method for recombinantly producing the transport polypeptide, antibodies which specifically bind to the polypeptide and polynucleotide sequences which specifically hybridize to polynucleotide encoding the transport polypeptide.

9 Claims, 29 Drawing Sheets

FIG. 1A (Linear) MAP of: cNT1rat

```
                CCTGACGCTGCCTTCTCACTGCAGATAAGTGAGTAG
157 TACAGGACCCTCTCCCCTCTCTATGCAGCCCTGTGTCTGTGAGTGCCCAGGGAGCAGGCA 216
    ---+---------+---------+---------+---------+---------+---------+
                                    M  A  D  N  T  Q  S  Q  R  E  S  I  S  L  T  P  M  A  H  G

217 TTACCAGTGTCTGGTGGTGCCTGTGTTCCACACGTCCTCATGAGGCTGAAGAGCCAAGCAC 276
    ---+---------+---------+---------+---------+---------+---------+
    CTGGAGAACATGGGGCAGAATTCCTGGAAAGCATGGAGGAAGGCCGACTCCCTCACAGT
    L  E  N  M  G  A  E  F  L  E  S  M  E  E  G  R  L  P  H  S

277 ATGGCAGAGACAACACAGAGCCAAAGAGAGTCCATTTCCCTCACGCCTATGGCCCACGGC 336
    ---+---------+---------+---------+---------+---------+---------+
    CACTCAAGCCCTGCCGGGAGGGTGAAGGTGCCTGAACAAAGCAGAGCGGAAGGCCTTCTCC
    H  S  S  L  P  E  G  E  G  G  L  N  K  A  E  R  K  A  F  S

337 CGATGGGAGGAGTCTGCAAGGCCGACTGTGCAAGGCGAGAAGCTTCTGCAGGAGCACCGGCAG 396
    ---+---------+---------+---------+---------+---------+---------+
    CTGTTTGGATGGATCTGCAAAGGCCTGCTCTCTACTGCATGTCTTGGCTTTCTTGATGGTC
    R  W  R  S  L  Q  P  T  V  Q  A  R  S  F  C  R  E  H  R  Q

397 ---+---------+---------+---------+---------+---------+---------+ 456
    L  F  G  W  I  C  K  G  L  L  S  T  A  C  L  G  F  L  M  V
```

```
457 GCCTGCCTCCTGGACCTCCAGAGGGCCCTAGCACTGTTGATCATCACCTGTGTGGTTCTC  516
     ---+---------+---------+---------+---------+---------+----
     GGACGGAGGACCTGGAGGTCTCCCGGGATCGTGACAACTAGTAGTGGACACACCAAGAG
     A   C   L   L   D   L   Q   R   A   L   A   L   L   I   I   T   C   V   V   L

517 GTCTTTCTGGCCTATGATCTGCTAAAGAGGCTTCTGGGGTCCAAGCTGAGGAGGTGTGTG  576
     ---+---------+---------+---------+---------+---------+----
     V   F   L   A   Y   D   L   L   K   R   L   L   G   S   K   L   R   R   C   V

577 AAGTTCAAGGCCATTCTTGCCCTGAGCCTCTGGCTGAAAAGAGGTCTAGCCCTTGCTGCT  636
     ---+---------+---------+---------+---------+---------+----
     K   F   Q   G   H   S   C   L   S   L   W   L   K   R   G   L   A   L   A   A

637 GGTGTGGGCCTGATCTCTGTGGCTATCTCTGGACACCGGCCCAGCGCCCTGAACAGCTGGTG  696
     ---+---------+---------+---------+---------+---------+----
     G   V   G   L   I   L   W   L   S   L   D   T   A   Q   R   P   E   Q   L   V

697 TCCTTTGCAGGGATCTGTGTGTTCCTTGTCCTTTTCGCTGGCTCAAAGCATCACCGT  756
     ---+---------+---------+---------+---------+---------+----
     S   F   A   G   I   C   V   F   L   V   L   F   A   G   S   K   H   H   R

757 GCGGGTGTCATGGCGAGCGTGTCCTGGGCCTTGGGCCAGTTTGTGCTTGGGCTCTTC  816
     ---+---------+---------+---------+---------+---------+----
     A   V   S   W   R   A   V   S   W   G   L   G   L   Q   F   V   L   G   L   F
```

FIG. 1B

```
817  GTCATCAGAACAGAACCAGGGTTCATTGCATTCCAGTGGCTAGGGGATCAGATCCAGGTC  876
     ---+---------+---------+---------+---------+---------+---
     TTCCTGAGTTACACCGAGGCAGGTTCCAGCTTCGTCTTCCGGAGAGGCTCTGGTGAAGGAT
      V  I  R  T  E  P  G  F  I  A  F  Q  W  L  G  D  Q  I  Q  V

877  TTCCTGAGTTACACCGAGGCAGGTTCCAGCTTCGTCTTCCGGAGAGGCTCTGGTGAAGGAT  936
     ---+---------+---------+---------+---------+---------+---
     GTCTTTGCCTTTCAGTTTTGCCCATCATCATCTTCTTCAGCTGCGTCATGTCTGTTCTG
      F  L  S  Y  T  E  A  G  S  S  F  V  F  G  E  A  L  V  K  D

937  GTCTTTGCCTTTCAGTTTTGCCCATCATCATCTTCTTCAGCTGCGTCATGTCTGTTCTG  996
     ---+---------+---------+---------+---------+---------+---
     TACTATCTGGGCCCTCAATGCAGTGGGTGATCCTGAAGATTGCCCTGGTTGATGCAGGTCACC
      V  F  A  F  Q  V  L  P  I  I  I  F  F  S  C  V  M  S  V  L

997  TACTATCTGGGCCCTCAATGCAGTGGGTGATCCTGAAGATTGCCCTGGTTGATGCAGGTCACC  1056
     ---+---------+---------+---------+---------+---------+---
     ATGGGCACCTCAGCCGAGACCACCGAGAGTGTGGCGGGAAACATCTTTGTGAGCCAGACT
      Y  Y  L  G  L  M  Q  W  V  L  K  I  A  W  L  M  Q  V  T

1057 ATGGGCACCTCAGCCGAGACCACCGAGAGTGTGGCGGGAAACATCTTTGTGAGCCAGACT  1116
     ---+---------+---------+---------+---------+---------+---
     GAAGCTCCCTGCTGATCCGGCCCTATCTGGCAGAGACATGACACTCTGAAGTTCACGTT
      M  G  T  S  A  T  E  T  L  S  V  A  G  N  I  F  V  S  Q  T

1117 GAAGCTCCCTGCTGATCCGGCCCTATCTGGCAGAGACATGACACTCTGAAGTTCACGTT  1176
     ---+---------+---------+---------+---------+---------+---
      E  A  P  L  L  I  R  P  Y  L  A  D  M  T  L  S  E  V  H  V
```

FIG. 1C

```
1177  GTCATGACTGGAGGCTATGCTACCATTGCTGGCAGCCTCCTGGGCGCCTACATCTCCTTT  1236
      ---+---------+---------+---------+---------+---------+
       V  M  T  G  G  Y  A  T  I  A  G  S  L  L  G  A  Y  I  S  F

1237  GGGATCGACGCTGCTTCCTTAATCGCAGCCCTCTGTCATGGCCCCCCCTTGTGCCGTTGGCT  1296
      ---+---------+---------+---------+---------+---------+
       G  I  D  A  A  S  L  I  A  A  S  V  M  A  A  P  C  A  L  A

1297  CTCTCCAAGCTGGTCTACCCAGAGGTGGAGGAGTCCAAGTTCCGGAGTGAGAATGGCGTG  1356
      ---+---------+---------+---------+---------+---------+
       L  S  K  L  V  Y  P  E  V  E  E  S  K  F  R  S  E  N  G  V

1357  AAGCTGACCTATGGAGACGCTCAGAACCTCTTGGAAGCAGCCAGTGCTGGGGCTGCCATC  1416
      ---+---------+---------+---------+---------+---------+
       K  L  T  Y  G  D  A  Q  N  L  L  E  A  A  S  A  G  A  A  I

1417  TCAGTGAAGGTCGTTGGCAACATTGCTGCCAATCTGATTGCCTTCCTGGCTGTACTAGCC  1476
      ---+---------+---------+---------+---------+---------+
       S  V  K  V  V  G  N  I  A  A  N  L  I  A  F  L  A  V  L  A

1477  TTCGTCAATGCTGCCCTCTCCTGGCTAGGGGACATGGTGGACATCCAGGGACTCAGCTTC  1536
      ---+---------+---------+---------+---------+---------+
       F  V  N  A  A  L  S  W  L  G  D  M  V  D  I  Q  G  L  S  F
```

FIG. 1D

```
1537 CAGCTCATCTGCTCCTACGTCCTGCGGCCTTCTTGATGGGTGTGGCCTGGGAG 1596
      Q   L   I   C   S   Y   V   L   R   P   V   A   F   L   M   G   V   A   W   E

1597 GACTGTCCGGTAGTGGCTGAGTTGCTGGGCATCAAGTTCTTTCTGAATGAGTTTGTGGCC 1656
      D   C   P   V   V   A   E   L   L   G   I   K   F   F   L   N   E   F   V   A

1657 TATCAAGAGAGCTTTCCCAGTACAAGCAACGCGCCTGGCAGGGGCTGAGGAGTGGCTTGGT 1716
      Y   Q   E   L   S   Q   Y   K   Q   R   R   L   A   G   A   E   E   W   L   G

1717 GACAAGAAACAGTGGATCTCTGTCAGAGCAGAAATCCTGACTACATACGCCCCTCTGTGGA 1776
      D   K   K   Q   W   I   S   V   R   A   E   I   L   T   T   Y   A   L   C   G

1777 TTTGCCAACTTCAGCTCCATCGGCATCATGTTGGGAGGCCTGACCTCCCTAGTCCCCCAG 1836
      F   A   N   F   S   S   I   G   I   M   L   G   G   L   T   S   L   V   P   Q

1837 CGGAGGAGCGACTTCTCCCAGATTGTACTCCGGGCACTGATCACAGGGGCTTTCGTGTCC 1896
      R   R   S   D   F   S   Q   I   V   L   R   A   L   I   T   G   A   F   V   S
```

FIG. 1E

```
1897  CTGCTAAACGCCCTGTGTGGCAGGGATCCTCTATGTACCCAGGGGGGTCGAGGTGGACTGC  1956
       ----+----+----+----+----+----+----+----+----+----+----+----+
       L  L  N  A  C  V  A  G  I  L  Y  V  P  R  G  V  E  V  D  C

1957  GTGTCCCTTCTGAACCAAACTGTCAGCAGCAGCTTTGAGGTTTACCTGTGTCGCCGC     2016
       ----+----+----+----+----+----+----+----+----+----+----+----+
       V  S  L  L  N  Q  T  V  S  S  S  F  E  V  Y  L  C  C  R

2017  CAAGTCTTCCAGAGCACTAGTCGGAGTTCAGCCAAGTGGCACTGGACAACTGTGTCGA   2076
       ----+----+----+----+----+----+----+----+----+----+----+----+
       Q  V  F  Q  S  T  S  S  E  F  S  Q  V  A  L  D  N  C  C  R

2077  TTTTACAACCACACAGTCTGCACATAG    2103
       ----+----+----+----+----+-
       F  Y  N  H  T  V  C  T  *

CTGGGACGGAGCATCTTCCTAGCCCTCATCCAGGCCTCATCCAGCCCAGAGAGGCCGTGGGACTC
      GTCACTACCTCCATCCCACAATTGGGAAGGGTGCAACGGTCATCGCTGCTCCCATGTCTG
      CCTCTCCAAGTACGAGTTCCCAGAGTCTGGTCTGCTCTGCCCTTTGGGAGCCAACAT
      TCTGGTCCTCTTGAGTCCTCTTTCCTTGGGAACCTCATGTGCACCAGCCAAAAGCCTCCT
      CCCTGCTCCCCCAAGCACCCAGCTTGTTGGGTATCCCCCAAAAGCTGTCTCTAGA
```

FIG. 1F (i) SEQ ID NO. 1:

ctggctgtgctgttcatctctcctagatgaatggatggtctacattcatccatttgattggccaaagacaccaaccc
cttctccctctacataagctgcactgcatggttgctgctggatggtgttcctgcttcctgctcctgatgctgacag
aacaaggctggaagtctgggacATGGAGAACGACCCCTCGAGACGAAGAGGCCAGCCTCCCTAGAGTGACTTGAGCTGCCAA
GGGTCTGGAGAACATGGGGGCTGATTTCTTGGAAAGCCTGGAAGCCTGGAACCTGCAGCCCTGAGAGCCAG
AGATCAGGAGCAGCTGGAGGAGCGGCCGAAGCCCTTCTCCAGATGGAGGAACCTGCAGCCCTGAGAGCCAGA
AGCTTCTGCAGGGAGCACATGCAGCTGTTTCGATGGATCGGCACAGGCCTGCTCTGCACTGGGCTCTCCTGCT
GGTGGCCTGCCTCCTGGATTTCCAGAGGGCCCTGCTCTGTTTGTCCTCACCTGTGTCCTCACCTTCCTGGCCACC
GCCTGCTGAAACGGCTTCTGGGGCCAAAGCTGAGGAGTTTCTTGTCAAGCCTGCATCCCCGCCTGCTCTGG
TTTAAGAGGGTCTAGCTCTTGCTTTCCCTGGCCTCGCTGTCTCCTGTCCCCAGCGGCCTGAGCA
ACTGGTGTCCTTGCAGGAATCTGCTGTTGCTGTCTCCTCTTTGCCTGCTCAAAGCATCATTGCGCAGTGTCCTGGA
GGGCCCGTGCTTGGGGACTTGGACTTGTACTTGGACTCCTCGTCATCAGAACAGAACCAGGATTCATTGCGTTC
GAGTGGCTGGGCGAGCAGATCCGGATCTTCCTGAGCTACACGTGTCTTTTCAGCTGTCATATCCGTTCTACCACGTGGCC
CAAGGATGTCTTTGCCTTTCAGGTTGCTGGTGAATCCTGAAGATTGCCTGGAAGTCCAAGTGATCGACAGCCCTGAGTGTGGT
TCATGCAGTGGGTGGGTGATCCTGAAGATCTTTGTGAGCCAGAGGTTACGCCAGAGCTCCATTACTCCGATCCGGCCTGATGCCA
GCTGGAAACATCTTTGACCGAGCCGAGGTTACGCCAGCCATCCTCCTTTGGATCTCCTTTGGATCGAGGTGGAGGAG
CCACGTTGTCATGACTGGCAGCCTCTGTGATGGCCTGCCCCCTTCTGCCCTCACAAACTGGTCTACCCGGAGGTGGAGGAG
CCTCGTTGATTGCAGCCCTCTGTGATGCCAGGGTGAAACTGACCTATGGAGATGCTCAGAGAAGCAGCACTGGGGC
TCCAAGTTAGGAGGAGGAGTCGCCAACATGCTGCCAACCTGATTGCGTTCCTGCTGTGCTGGACTTTATCAATGCTG
CGCCATCCGTGAAGGT

FIG. 6A

```
CCCTCCTCCTGGCTGGAGAGACATGGTGGACATCCAGGGGCTTCAGCTCATCTGCTCCTACATCCTGCGGCCTGTA
GCCTTCTTGATGGGTGTGGCCGTGGAGGACTGCCAGTGGTAGCTGAGCTGTGGGATCAAGCTGTTTCTGAACGAGTT
TGTGGCCTATCAAGACCTCCAAGTACAAGCCCGCCTGGCAGGGGCCGAGAGTGCCGGCGACAGGAAGCAGT
GGATCTCCGTCAGAGCTGAAGTCCTCACGACGTTTGCCCTCTGTGGATTTGCCAATTTCAGCTCCATTGGGATCATGCTG
GGAGGCTTGACCTCCATGGTCCCCAACGGAAGAGCGACTTCTCCCAGATAGTGCTCCGGGCGCTCTTCACGGGAGCCTG
TGTGTCCCTGGTGAACGCCTGTATGCCAGGATCCTCTACATGCCCAGGGGCTGAAGTTGACTGCATGTCCCTCTTGA
ACACGACCCTCAGCAGCAGCTTTGAGATTTACCAGTGCTGCCCGTGAGGCCTTCCAGAGCGTCAATCCAGAGTTCAGC
CCAGAGGCCCTGGACAACTGCTGTCGTTTACAACCACGATCTGTGCACAGTGAggacagaacatgctgtgcttct
gcgcttctgagggctgttctccccggaaccatctgtccccacctttccctttcccagagccctcttcagggaagccaca
ggacttagaccagctcaatccacatcccccattcctgctcccccagtgtgaattctcaggtgagtgaggacataaggaa
ggacatgtcccactccatcccccctccccctcctaactcccccagtgtgaattctcaggtcacttctgcc
tcctcccgtttccccctccacatccaaacagcaccctcctccctctatccccccacttcctgggtccctcacatgcccct
tccctttctgttgggctgcacaccaaagccctcctttcagagaaaccctcctttcctagcactaggatctctgtgcttccc
tgctgggtggtgtcacctcttctgctttcagagggcgttcagagggttccatgatggactaggtttccagtgctcccaaactgaggtc
ccatggcacactgtcctgggaggcgttcagagggttccatgatggactaggtttggaaccactggttaataacttag
agagggctgttTaaaaaaaaaaaaaaaaaaaaaaaaaaaaaaa
```

(ii) SEQ ID NO. 2:

tggaagtctgggacATGGAGAACGACCCCTCGAGACGGAGAGAGTCCATCTCTCCACACCTGTGGCCAAGGGTCTGGA
GAACATGGGGGCTGATTTCTTGGAAAGCCTGGAGAGAAGGCCAGCTCCCTAGGAGTGACTTGAGCCCCGCAGAGATCAGGA

FIG. 6B

```
GCAGCTGGAGCGAGGCGGCGCCGAAGCCCTTCTCCAGATGGAGGAACCTGCAGCCCTGAGAGCCAGAAGCTTCTGC
AGGGAGCACATGCAGCTGTTTCGATGGATCGGCACAGGCCTGCTCTGCACTGGGCTCTCTGCCTTCCTGCTGGCCTG
CCTCCTGGATTTCCAGAGGGCCCTGGCTCTCGTTGTCCTCACCTGTGTGGTCCTCAGGGCCATCCCCGCCTCTGCTGA
AACGGCTTCTGGGGCCAAAGCTGAGGAGGTTTCTCAAGCCTGCTGTCTCTGCCTGCTGCCTGAGCAGCTGGTGTCCTT
CTAGCTCTTGCTGTGTTCATCGCTTCTCCTCTTGCCTGCTCAAAGCATCATTGCGCAGTGTCCTGGAGGCCGTGTCTT
CGCAGGAATCTGCAGTTTGTACTTGGACTCCTCGTCATCAGAACAGGATTCATTGCGTTCGAGTGGCTGGGC
GGGGACTTGGACTGCAGTTTGTACTTGGACTCCTCGTGTTGGGGAGGCGCTGGTCAAGGATGCTT
GAGCAGATCCGGATCTTCCTGAGCTACACGAAGGCTGGCTTCGTGTTCGTATCCGTTCCCAGCCCTGTGGGAGCCCTGAGACCCTGAGTGTGGCTGGAAACATC
TGCCTTTCAGGTTCTGCCCATCATTGTCTTTTCAGCTCTGATGCAAGTCACCATGGCACCACAGCCCTACTGGGCTGGCCCTGTTGCCACGTGGGCTCTGAAGTCCACGTTGTCAT
TTTGTGAGCCAGACCGAGGCTCCATTACTGATCCGGCCCTGCCCCTTGCTGCTGGCAGACATGACACTCTCTTTGGGATCGATGCCACCTCGTTGATTG
GACCGGAGGTTACGCCACCATTGCTGCTGGCCAGCCTGGGTGCCTACATCTCCTTTGCCTACCGGTGCCCCAAGCTGGTACCCGGAGGTGGAGGAGTCCAAGTTTAGG
CAGCCTCTGTGATGGCTGCCCCTTGTGCCCTTGCCTATGGAGATGCTCAGAGCCTCAGTGCCTGCTGTGCTTCCGT
AGGGAGGAGGAGTGAAACTGACCTATGCTGCCAACCTGCCACCTCGCTGTGTTCCTGGACTTTATCAATGCTCCCTGGC
GAAGGTGCTGCCAACATCGCTCCAGGGCTCCACTGCCCTCCAGCTCCATCTGCTCCTACATCCTGCGGCCTGTAGCCTTCTTGATG
TGGGAGACATGGTGGACATCCAGGGCTCAGCTGCTGCTGCCTGCCTCAGCTGCTGTCGTGCTGGGATCAAGCTGTTTCTGAACGAGTTTGTGGCCTATCA
GGTGTGGCGTGGGAGGACTGCCCAGTGGACTGCCTGGTAGCTGAGCTGCCAGGGCCGAGGAGTGGTCGGCAACAGGAAGCAGTGGATCCCGTCA
AGACCTCTCCAAGTACAAGCAACGCCGCCTGGCAGTGAGCGCCGAGGAGTCCAATTTCAGCTCCATTGGGATCATGCTGGGAGGCTTGACC
GAGCTGAAGTCCCTCACGACGTTTGCCCTCTGTGGATTGCCAGATAGTGCTCCGGGCGCTCTTCACGGGAGCCTGTGTGACC
TCCATGGTCCCCCCAACGGGAAGAGCGACTTCTCCCCAGATAGTGCTCCGGGCGCTCTTCACGGGAGCCTGTGTGTCCCTGGT
```

FIG. 6C

```
GAACGCCCTGTATGGCAGGATCCTCTACATGCCCAGGGGGCTGAAGTTGACTGCATGTCCCTCTTGAACACGACCCTCA
GCAGCAGTAGCTTTGAGATTTACCAGTGCTGCCCGTGAGGCCTTCCAGAGCGTCAATCCAGAGTTCAGCCCAGAGCCCTG
GACAACTGCTGTCGGTTTTACAACACAGATCTGCGCACAGTGAggacagaacatgctgtgttctgcgttctgagg
gctgttctccccggaaccatctgtccccaccttccctttcccagagccctcttcaggaaagccacaggacttagat (iii) SEQ ID NO. 3:
tggaagtctggacATGGAGAACGACCCCTCGAGACGGAGAGAGTCCATCTCTCTCACACCTGTGGCCAAGGGTCTGGA
GAACATGGGGGCTGATTTCTTGGAAAGCCTGGAGAAGGCCAGCTCCTCCTAGGAGTGACTTGAGCCCCGCAGAGATCAGGA
GCAGCTGGAGCGCCGAAGCCCTTCTCCAGATGGAGAACCTGCAGCCCAGCCTGAGAGCCAGAAGCTTCTGC
AGGGAGCACATGCAGCTGTTTCGATGGATCGGCACAGGCCTGCTCTGACCTGTGTGTCCCTCAAGCCTGGGCTCCTGG
CCTCCTGGATTCCAGAGGCCTTGGGGCCAAAGCTGAGGAGTTTCTCAAGCCTGTGGCTCTGTTGCCTCTGGTTAAGAGGGT
AACGGGCTTCTGGGCTGCTTTCCTGGCCTGCTGTTCTGCTCCCTAGGAGCCGCTCCCAGCCTCCCAGCCTGAGCAGCTGGTGTCCTT
CTAGCTCTGTTGCTTCATCGCTGTGTTCATCGCTTCTCCTTGCCTCGTCAGTGTCCTGGAGGGCCGTGTCTT
CGCAGGAATCTGCGTGTTCATCGCTGTTCATCGCTTCTCCTTGCCTCTCGTCATCAGAACAGGATTCATTGCGTTCGAGTGGCGTGGGC
GGGGACTTGGACTGCAGTTTGTACTTGACTCCGTCATCAGAACAGGATTCATTGCGTTCGAGTGGCGTGGGC
GAGCAGATCCGGATCTTCCTGAGCTACACGAAGGCTGGCTTCGTGTTTGGGAGGCCTGGTCAAGGATGTCTT
TGCCTTTCAGGTTCAGCTTGCTGCCCATCATTGTCTTTTTCAGCTGTCATATCCGTTCATCAGACCCTGGGCCATGCAGTGGG
TGATCCTGAAGATTGCCTGGTCAAGTCACCATGGCCACCACGTGAGACCCACTGAGTGTGGCTGGAAACATC
TTTGTGAGCCAGACCGAGGCTCCATTACTGATCCGGCCTACTTGGCAGACATGACACTCTGAAGTCCACGTTGTCAT
GACCGGAGGTTACGCCCACCATTGCTGGCAGCCTGCTGGGTGCCTACATCTCCTTTGGGATCGATGCCACCTCGTTGATTG
```

FIG. 6D

```
CAGCCCTCTCTGTGATGGCTGCCCCCTTGTGCCTTGGCCCCTCTCCAAGCTGGTCTACCCGGAGGTGGAGGAGTCCAAGTTTAGG
AGGGAGGAAGGAGTGAAACTGACCTATGGAGATGCTCAGAACCTCATAGAAGCAGCACTGGGCCGCCATCTCCGT
GAAGGTGGTCGCCAACATCGCTGCCAACCTGATTGCTGTTCCTGGCTGTGTGCTGGACTTTATCAATGCTGCCTGC
TGGGAGACATGGTGTGGACATCCAGGGCTCAGCTTCCAGCTCCATCTGCTCCTACATCCTGCGCCTGTAGCCTTCTTGATG
GGTGTGCCGTGGGAGGACTGCCAGTGGTAGCTGCCCAGTGGTAGCTGCTGCTGAGCTGTTTCTGAACGAGTTTGTGGCCTATCA
AGACCCTCCAAGTACAAGCAACGCCCGGCCAGGGCCGAGGAGTGGGTCGGCAACAGGAAGCAGTGGATCTCCGTCA
GAGCTGAAGTCCTCACGACGTTTGCCCCCTCTGTGGATTTGCCAATTTCAGCTCCATTGGATCATGCTGGGAGGCTTGACC
TCCATGGTCCCCCAACGGAAGAGCGACTTCTCCCCAGATAGTGCTCCGGCGCTCTTCACGGCCTGTGTGCCCTGGT
GAACGCCTGTATGGCAGGAGATCCTCTACAGGCCCAGGGGGCTGAAGTTGACTGCATGTCCCTCTTGAACACGACCCTCA
GCAGCAGTAGCTTTGAGATTTACCAGTGCCTTGCCGCGTGAGGCCTTGCAGCCTCAATCCAGAGTTCAGCCACGAGGCCCTG
GACAACTGCTCGTGTCGGTTTTACAACCACACGATCTGCGCACAGTGAggacagaacatgcttgtgcttctgcgcttctgagg
gctgttctccccggaaccatctgtcccaccttcccctttcccagagccctcttcaggaagccacagaccttagat
```

*FIG. 6E*

(i) SEQ ID NO. 4:

MENDPSRRRESISLTPVAKGLENMGADFLESLEGGQLPRSDLSPAEIRSSWSEAAPKPFSRWRNLQPALRARSFCREHMQ
LFRWIGTGLLCTGLSAFLLVACLLDFQRALALFVLTCVVLTFLGHRLLKRLLGPKLRRFLVKPQGHPRLLLWFKRGLALA
AFLGLVLWLSLDTSQRPEQLVSFAGICVFVALLFACSKHHCAVSWRAVSWGLGLQFVLGLLVIRTEPGFIAFEWLGEQIR
IFLSYTKAGSSFVFGEALVKDVFAFQVLPIIVFFSCVISVLYHVGLMQWVILKIAWLMQVTMGTTATETLSVAGNIFVSQ
TEAPLLIRPYLADMTLSEVHVVMTGGYATIAGSLLGAYISFGIDATSLIAASVMAAPCALALSKLVPEVEESKFRREEG
VKLTYGDAQNLIEAASTGAAISVKVVANIAANLIAFLAVLDFINAALSWLGDMVDIQGLSFQLICSYILRPVAFLMGVAW
EDCPVVAELLGIKLFLNEFVAYQDLSKYKQRRLAGAEEWVGDRKQWISVRAEVLTTFALCGFANFSSIGIMLGGLTSMVP
QRKSDFSQIVLRALFTGACVSLVNACMAGILYMPRGAEVDCMSLLNTTLSSSSFEIYQCCREAFQSVNPEFSPEALDNCC
RFYNHTICAQZ (ii) SEQ ID NO. 5:

MENDPSRRRESISLTPVAKGLENMGADFLESLEEGQLPRSDLSPAEIRSSWSEAAPKPFSRWRNLQPALRARSFCREHMQ
LFRWIGTGLLCTGLSAFLLVACLLDFQRALALFVLTCVVLTFLGHRLLKRLLGPKLRRFLKPQGHPRLLLWFKRGLALAA
FLGLVLWLSLDTSQRPEQLVSFAGICVFIALLFACSKHHCAVSWRAVSWGLGLQFVLGLLVIRTEPGFIAFEWLGEQIRI
FLSYTKAGSSFVFGEALVKDVFAFQVLPIIVFFSCVISVLYHVGLMQWVILKIAWLMQVTMGTTATETLSVAGNIFVSQT
EAPLLIRPYLADMTLSEVHVVMTGGYATIAGSLLGAYISFGIDATSLIAASVMAAPCALALSKLVPEVEESKFRREEGV
KLTYGDAQSLIEAASTGAAISVKVVANIAANLIAFLAVLDFINAALSWLGDMVDIQGLSFQLICSYILRPVAFLMGVAWE

FIG. 7A

DCPVVAELLGIKLFLNEFVAYQDLSKYKQRRLAGAEEWVGNRKQWISVRAEVLTTFALCGFANFSSIGIMLGGLTSMVPQ
RKSDFSQIVLRALFTGACVSLVNACMAGILYMPRGAEVDCMSLLNTTLSSSSFEIYQCCREAFQSVNPEFSPEALDNCCR
FYNHTICAQ (iii) SEQ ID NO. 6:

MENDPSRRRESISLTPVAKGLENMGADFLESLEEGQLPRSDLSPAEIRSSWSEAAPKPFSRWRNLQPALRARSFCREHMQ
LFRWIGTGLLCTGLSAFLLVACLLDFQRALALFVLTCVVLTFLGHRLLKRLLGPKLRRFLKPQGHPRLLLWFKRGLALAA
FLGLVLWLSLDTSQRPEQLVSFAGICVFIALLFACSKHHCAVSWRAVSWGLGLQFVLGLLVIRTEPGFIAFEWLGEQIRI
FLSYTKAGSSFVFGEALVKDVFAFQVLPIIVFFSCVISVLYHVGLMQWVILKIAWLMQVTMGTTATETLSVAGNIFVSQT
EAPLLIRPYLADMTLSEVHVVMTGGYATIAGSLLGAYISFGIDATSLIAASVMAAPCALALSKLVYPEVEESKFRREEGV
KLTYGDAQNLIEAASTGAAISVKVVANIAANLIAFLAVLDFINAALSWLGDMVDIQGLSFQLICSYILRPVAFLMGVAWE
DCPVVAELLGIKLFLNEFVAYQDLSKYKQRRLAGAEEWVGNRKQWISVRAEVLTTFALCGFANFSSIGIMLGGLTSMVPQ
RKSDFSQIVLRALFTGACVSLVNACMAGILYMPRGAEVDCMSLLNTTLSSSSFEIYQCCREAFQSVNPEFSPEALDNCCR
FYNHTICAQZ

FIG. 7B

```
hCNT1a   1 MENDPSRRRE SISLTPVAKG LENMGADFLE SLEGGQLPRS DLSPAEIRS.
rCNT1      MADNTQSQRE SISLTPMAHG LENMGAEFLE SMEEGRLPHS HSSLPEGEG.
SPNT       ..MAKSEGRK SASQDTSENG MENPG....LE LMEVGNLEQG KTLEEVTQGH
NUPC hCNT1a  51 SWSEAAPKPF SRWRNLQPAL RARSFCREHM QLFRWIGTGL LCTGLSAFLL
rCNT1      GLNKAERKAF SRWRSLQPTV QARSFCREHR QLFGWICKGL LSTACLGFLM
SPNT       SLKDGDGHSS LWRRILQPFT KARSFYQRHA GLFKKILLGL LCLAYAAYLI
NUPC hCNT1a 101 VACLLDFQRA LALFVLTCVV LTFLGHRLLK RLLGPKLRRF LVKPQGHPRL
rCNT1      VACLLDLQRA LALLITCVV LVFLAYDLLK RLLGSKLRRC VKFQGHSCL
SPNT       AACILNFRRA LALFVITCLV IFILACHFLK KFFAKKSIRC LKPLKNTRL
NUPC       ...MDRVLHF hCNT1a 151 LLWEKRGLAL AAFLGLVLWL SLDTSQRPEQ LVSFAGICVF VALLFACSKE
rCNT1      SLWLKRGLAL AAGVGLILWL SLDTAQRPEQ LVSFAGICVF LVLLFAGSKE
SPNT       RLWLKRVFMG AAVVGLILWL ALDTAQRPEQ LISFAGICME ILILFACSKE
NUPC       ........... .......... .......... VLALAVVAIL ALIV....SSD
```

FIG. 8A

|          | 201                                                                                     | 250 |
|----------|-----------------------------------------------------------------------------------------|-----|
| hCNT1a   | HCAVSWRAVS  WGLGLQFVLG  LLVIRTEPGF  IAFEWLGEQI  RIFLSYTKAG                              |     |
| rCNT1    | HRAVSWRAVS  WGLGLQFVLG  LFVIRTEPGF  IAFQWLGDQI  QVELSYTEAG                              |     |
| SPNT     | HSAVSWRTVF  WGLGLQFVEG  ILVIRTEPGF  NAFQWLGDQI  QIFLAYTVEG                              |     |
| NUPC     | RKKIRIRYVI  QILVIEVLLA  WFFLNSDVGL  GFVKGFSEMF  EKLLGFANEG                              |     |

|          | 251                                                                                     | 300 |
|----------|-----------------------------------------------------------------------------------------|-----|
| hCNT1a   | FSSVFG..EA  LVKDVFAFQV  LPIVFFSCV  ISVLYHVGLM  QWVILKIAWL                               |     |
| rCNT1    | SSEVFG..EA  LVKDVFAFQV  LPIIFFSCV  MSVLYLYLGLM  QWVILKIAWL                              |     |
| SPNT     | SSEVFG..DT  LVQSVFAFQS  LPIIFFGCV  MSILYYLGLV  QWVIQKIAWF                               |     |
| NUPC     | TNEVFGSNDQ  GLAEFFLKV  LCPIVFISAL  IGILQHIRVL  PVIIRAIGFL                               |     |

|          | 301                                                                                     | 350 |
|----------|-----------------------------------------------------------------------------------------|-----|
| hCNT1a   | MQVTMGTTAT  ETLSVAGNIF  VSQTEAPLLI  RPYLADMTTS  EVHVVMTGGY                              |     |
| rCNT1    | MQVTMGTSAT  ETLSVAGNIF  VSQTEAPLLI  RPYLADMTTS  EVHVVMTGGY                              |     |
| SPNT     | LQITMGTTAA  ETLAVAGNIF  VGMTEAPLLI  RPYLADMTTS  ETHAVMTGGF                              |     |
| NUPC     | LSKVNGMGXL  ESFNAVSSLI  LGQSENFIAY  KDILGKISRN  RMYTMAATAM                              |     |

|          | 351                                                                                     | 400 |
|----------|-----------------------------------------------------------------------------------------|-----|
| hCNT1a   | ATTAGSLLGA  YISFGIDATS  LIAASVMAAP  CALALSKLVY  PEVEESKFRR                              |     |
| rCNT1    | ATTAGSLLGA  YISFGIDAAS  LIAASVMAAP  CALALSKLVY  PEVEESKFRS                              |     |
| SPNT     | ATTAGTVLGA  FISFGIDASS  LISASVMAAP  CALALSKLVY  PEVEESKFKS                              |     |
| NUPC     | STVSMSIVGA  YMTM.LEPKY  VVAALVLNMF  STFIVLSLIN  PYRVDA....S                             |     |

FIG. 8B

|       | 401         |            |            |            | 450 |
|-------|-------------|------------|------------|------------|-----|
| hCNT1a | EEGVKLT.YG | DAQNLIEAAS | TGAAISVKVV | ANIAANLIAF | LAVLDFINAA |
| rCNT1 | ENGVKLT.YG | DAQNLLEAAS | AGAAISVKVV | GNIAANLIAF | LAVLAFVNAA |
| SPNT  | KEGVKLP.RG | EERNILEAAS | NGATDAIALV | ANVAANLIAF | LAVLAFINST |
| NUPC  | EENIQMSNLH | EGQSFFEMLG | EYILAGFKVA | IIVAAMLIGE | IALIAALNAL |

|       | 451         |            |            |            | 500 |
|-------|-------------|------------|------------|------------|-----|
| hCNT1a | LSWLGDMVDI | QGLSFQLICS | YILRPVAFLM | GVAWEDCPVV | AELLGIKLFL |
| rCNT1 | LSWLGDMVDI | QGLSFQLICS | YVLRPVAFLM | GVAWEDCPVV | AELLGIKLFL |
| SPNT  | LSWLGFMVDI | HGLTFQVICS | YVLRPMVFMM | GVQWADCPLV | AEIVGVKEFI |
| NUPC  | FATVTGWFGY | .SISFQGILG | YIFYPIAWVM | GVPSSEALQV | GSIMATKLVS |

|       | 501         |            |            |            | 550 |
|-------|-------------|------------|------------|------------|-----|
| hCNT1a | NEFVAYQDLS | KYKQRRLAGA | EEWVGDRKQW | ISVRAEVLTT | FALCGFANFS |
| rCNT1 | NEFVAYQELS | QYKQRRLAGA | EEWLGDKKQW | ISVRAEILTT | YALCGFANFS |
| SPNT  | NEFVAYQQLS | QYKNKRLSGV | EEWINGEKQW | ISVKAEIIAT | ESLCGFANFS |
| NUPC  | NEFVAMMDL. | .....QKIAST | ........... | LSPRAEGIIS | VFLVSFANFS |

*FIG. 8C*

```
             551                                                                              600
hCNT1a       SIGIMLGGLT   SMVPQRKSDF   SQLVLRALFT   GACVSLVNAC   MAGILYMPRG
rCNT1        SIGIMLGGLT   SLVPQRRSDF   SQIVLRALIT   GAEVSLLNAC   VAGILYVPRG
SPNT         SIGITLGGLT   SMVPQRKSDL   CKILVVRALFT  GACVSFISAC   MAGILYVPRG
NUPC         SIGIIAGAVK   GLNEEQGNVV   SRFGLKLVYG   STLVSVLSAS   IAALVL....

601                                                                              650
hCNT1a       AEVDCMSLLN   TTLSSSSFEI   YQCCREAFQS   V.........   .....NPEF
rCNT1        VEVDCVSLLN   QTVSSSSFEV   YLCCRQVFQS   T.........   .....SSEE
SPNT         AETDCVSFLN   TNFTNRTYET   YVCCRELFQS   TLLNGTNMPS   FSGPWQDKES
NUPC         .........   ..........   ..........   ..........   .........

651                          670
hCNT1a       SPEALDNCCR   FYNHTICAQ
rCNT1        SQVALDNCCR   FYNHTVCT.
SPNT         SLRNLAKCCD   LYTSTVCA.
NUPC         .........   .........
```

FIG. 8D

| | Residue Number | | | | | | | | | | | |
|---|---|---|---|---|---|---|---|---|---|---|---|---|
| | 9 | 34 | 134 | 135 | 141 | 190 | 216 | 266 | 377 | 410 | 522 | 640 |
| pMHK1/hCNT1a | R | G | P | K | V | V | F | Q | P | N | D | C |
| pMHK2/hCNT1b | R | E | P | K | - | I | F | Q | P | S | N | C |
| pMHK3 | STOP | E | T | K | - | V | L | Q | P | N | N | C |
| pMHK4 | R | E | P | E | - | I | F | R | S | N | N | STOP |
| RTPCR direct | R | E | P | K | - | I | F | Q | P | N | N | C |

FIG. 10

CDNA ENCODING NUCLEOSIDE TRANSPORTER

This is a Continuation-In-Part Application of U.S. patent application Ser. No. 08/499,314, filed Jul. 7, 1995 now abandoned.

FIELD OF THE INVENTION

This invention relates generally to $Na^+$-dependent nucleoside transporters and specifically to cDNA sequences encoding $Na^+$-dependent nucleoside transport proteins.

BACKGROUND OF THE INVENTION

Natural and synthetic nucleosides have important physiologic and pharmacologic activities in humans. Adenosine, for example, is a local signaling molecule with regulatory functions in lipolysis, neurotransmitter release, platelet aggregation, coronary vasodilation, and cardiac contractility (Belardinelli et al., 1989; Jacobson et al., 1990). Nucleoside antimetabolites have therapeutic applications in human neoplastic and viral diseases, including leukemias and AIDS (Perigaud et al., 1992; Handschumacher and Cheng, 1993).

Most nucleoside drugs act intracellularly, after anabolic phosphorylation, by interfering, either directly or indirectly, with DNA synthesis. For those nucleosides that are hydrophilic, mediated transport systems (NT processes) are required for passage across the plasma membrane. In experimental systems, there is evidence that the activity of NT The abbreviations used are: AIDS, acquired immunodeficiency syndrome; HIV, human immunodeficiency virus; NBMPR, nitrobenzylthioinosine (6-[(4-nitrobenzyl)thio]-9-p-D-ribofuranosylpurine); AZT, 3'-azido-3'-deoxythymidine; ddC, 2',3'-dideoxycytidine; ddG, 2',3'-dideoxyguanosine; ddI, 2',3'-dideoxyinosine; bp, base pair(s); kb, kilobase(s). cDNA, complementary DNA; DAPI, 4',6-diamidin-2-phenylindol-dihydrochloride; ddC, 2',3'-dideoxycytidine; FISH fluorescence in situ hybridization; avidin-FITC, avidin-fluorescein isothiocyanate; HIV, human immunodeficiency virus; kb, kilobase(s); NT, nucleoside transporter; PAC, P1-derived artificial chromosome; poly(A)$^+$, polyadenylated; PCR, polymerase chain reaction; RT-PCR, reverse manscriptase polymerase chain reaction; CNT1 and CNT1 both represent concentrative nucleoside transporter 1.

processes can be an important determinant of pharmacologic action of cytotoxic nucleoside drugs. For example, cultured cells made incapable of transporting nucleosides by genetic mutations or treatment with NT inhibitors exhibit low levels of uptake of adenosine and other endogenous nucleosides and are resistant to a variety of nucleoside analogs with anticancer activity The permeant selectivities and mechanisms regulating distribution and expression of NT processes are important factors to be considered in the design of nucleoside analogs as therapeutic agents in human diseases.

Both equilibrative and $Na^+$-dependent nucleoside transport mechanisms are present in mammalian cells. In human erythrocytes, transport of purine and pyrimidine nucleosides is equilibrative ($Na^+$-independent) and inhibited by namomolar concentrations of NBMPR (Young and Jarvis, 1983; Paterson et al, 1983). The erythrocyte transporter, an integral membrane glycoprotein of apparent $M_r$ 55,000 (Wu et al 1983), has been purified to apparent homogeneity by a combination of ion-exchange and immunoaffinity chromatography (Kwong et al 1988). Functionally and structurally similar equilibrative nucleoside transporters (designated es) are widely distributed in mammalian cells and tissues (Paterson et al, 1991; Kwong et al, 1993)). In addition, some mammalian cells and tissues (Paterson et al, 1991) possess $Na^+$-independent nucleoside transport systems with low (micromolar) sensitivity to inhibition by NBMPR (designated ei). The molecular properties of ei transporters are unknown.

$Na^+$-dependent nucleoside transport systems have been demonstrated in a variety of cell types, including intestinal (Vijayalakshimi and Belt, 1988; Jarvis, 1989; Roden et al, 1991), renal epithelia (Lee et al, 1990; Williams and Jarvis, 1991; Gutierrez and Giacomini, 1993), and choroid plexus (Wu et al, 1992), liver (Che et al., 1992); splenocytes (Plagemann et al., 1990), macrophages (Plagemnann, 1991) and leukemia cells (Belt et al., 1993, Paterson et al. 1993). Active, $Na^+$-linked NT processes are present in intestinal (Betcher et al., 1990; Vijayalakshmi and Belt, 1988) and renal epithelia (Gutierrez and Giacomini 1993; Le Hir and Dubach, 1984; Williams et al., 1989), choroid plexus (Wu et al., 1994), liver (Che et al., 1992), splenocytes (Plagemann et al., 1990), macrophages (Plagemann, 1991) and leukemic cells (Belt et al. 1993; Paterson et al., 1993). The two principal $Na^+$-dependent NT subtypes, designated N1 (or cif) and N2 (or cit), have complementary and overlapping selectivities for purine nucleosides and uridine (N1/cif) and pyrimidine nucleosides and adenosine (N2/cit). N1/cif and N2/cit NTs have been found in tissues and cells of rat, rabbit, murine and bovine origin (Cass, 1995). A third class of $Na^+$-dependent NTs, designated N3 (or cib), found to date only in rat jejunum (Huang et al., 1993), rabbit choroid plexus (Wu et al., 1994) and human leukemic cells (Belt et al., 1993), has the ability to transport a wide range of both purine and pyrimidine nucleosides. A human kidney N2/cit-like process that is selective for guanosine in addition to pyrimidine nucleosides and adenosine has been given the designation N4 (Gutierrez and Giacomini, 1993; Gutierrez and Giacomini, 1994). Finally, a $Na^+$-dependent NT activity that is inhibited by NBMPR and designated N5 (or cs) has been observed in freshly isolated human leukemic cells (Paterson et al., 1993). It is not known from the current literature if human cells express the N1/cif and N2/cit NT subtypes (Cass, 1995).

It has been demonstrated that Xenopus oocytes express $Na^+$-dependent nucleoside transport activity after microinjection of poly $(A)^+$ RNA from rat jejunum (Huang et al, 1993).

BRIEF DESCRIPTION OF THE DRAWINGS

FIG. 1 shows the cDNA nucleotide sequence and deduced amino acid sequence of rat jejunal concentrative nucleoside transporter 1 (CNT1) (SEQ ID NO. 7 and 8 respectively).

FIG. 6 shows the cDNA nucleotide sequences from human kidney and obtained from 2-different humans (hCNT1b and hCNT1c are derived from the same human kidney preparation.) (i) hCNT1a herein referred to as SEQ ID NO. 1, (ii) hCNT1b herein referred to as SEQ ID NO. 2 and (iii) hCNT1c is the RT-PCR direct sequence herein referred to as SEQ ID NO. 3.

FIG. 7 shows the deduced amino acid sequences for (i) hCNT1a herein referred to as SEQ ID NO. 4, (ii) hCNT1b herein referred to as SEQ ID NO. 5 and (iii) hCNT1c herein referred to as SEQ ID NO. 6.

FIG. 8 shows the multiple alignment of human kidney hCNT1a, rat jejunal rCNT1, 4 rat liver SPNT (rCNT2) and *E. coli* nuc. The amino acid sequence of hCNT1a (650 amino acid residues) was deduced from the nucleotide open reading frame of clone pMHK1 (GeneBank™/EMBL Data Bank accession number U62966). Alignment of hCNT1a, rCNT1, SPNT (rCNT2 in our nomenclature)(Che et al. 1992) and *E. coli* nupC (Craig et al. 1994) was performed using the GCG PILEUP program. Amino acid residues in rCNT1, SPNT (rCNT2) and nupC identical to those in hCNT1a are highlighted. Conserved regions corresponding to rCNT1 PCR primers Q1 and Q2 are underlined.

FIG. 10 shows differences in the deduced amino acid sequences of hCNT1a and hCNT1 cDNAs produced by RT-PCR amplification of human kidney RNA. The sequences of three randomly selected hCNT1 RT-PCR clones (pMHK2–pMHK4) were aligned with hCNT1a Only one, hCNT1b (649 amino acid residues, plasmid pMHK2), exhibited uridine transport activity when expressed in oocytes (GeneBank™/EMBL Data Bank accession number U62967). Also included in the alignment was the open reading frame derived from direct sequencing of the RT-PCR product from which pMHK2–pMHK4 were cloned (GeneBank™/EMBL Data Bank accession number U62968). There was >99% identity between the five amino acid sequences. Putative polymorphic sites are boxed. Putatitive PCR-induced mutations are highlighted.

DETAILED DESCRIPTION OF THE INVENTION

Figure 2:
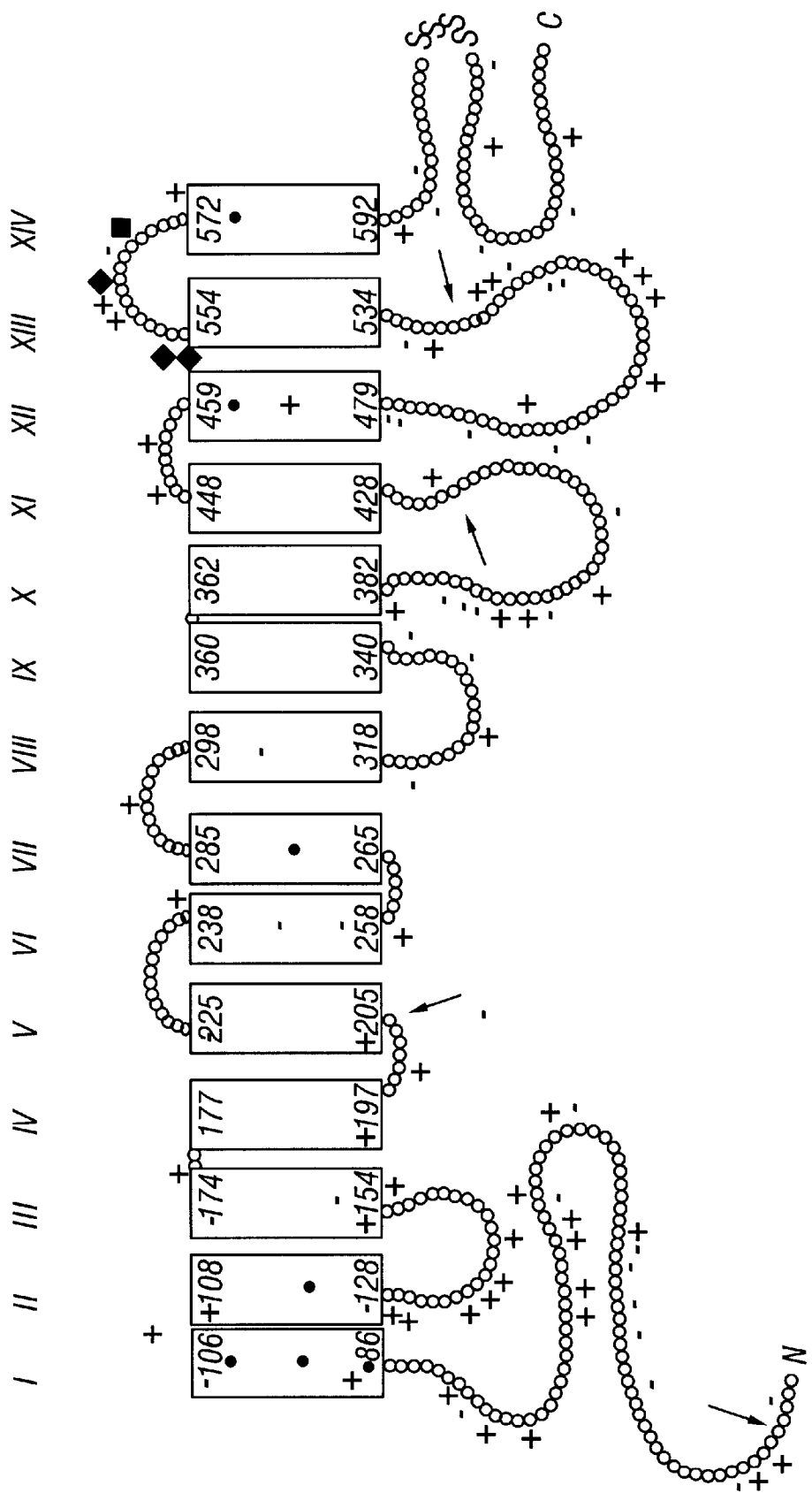
FIG. 2 shows a topographical model of CNT1. Potential membrane spanning domains are numbered and shown as rectangles. The relative positions of acidic (glutamate, aspartate), basic (lysine, arginine), and cysteine residues are indicated by −, +, and ·, respectively. One potential N-linked glycosylation site (asparagine 543) is located within transmembrane segment 13, while the other two (asparagines 605 and 643) are predicted to be intracellular. Four possible O-linked glycosylation sites are located in the extracellular loop linking transmembrane domains 13 and 14 (■). All four potential protein kinase C-dependent phosphorylation sites are predicted to be intracellular (↑).

The present invention provides a cDNA sequence encoding an Na$^+$-dependent nucleoside transporter. The isolation, functional expression and chromosomal localization of cDNAs encoding human isoforms of rCNT1 is herein reported. This is the first molecular cloning of human NT cDNAs and the first demonstration that members of the CNT family of NT proteins and their associated transport activities exist in human cells. The present invention describes herein the isolation from human kidney of a series of cDNAs (pMHK1–pMHK4) encoding human homologs (hCNT1a and hCNT1b) of rCNT1 and their functional expression in Xenopus oocytes.

The present invention provides a new human nucleoside transporter protein by molecular cloning and functional expression of its cDNA. cDNAs for a human homolog of rCNT1, designated hCNT1, have now been isolated from human kidney by hybridization cloning and reverse transcriptase polymerase chain reaction amplification strategies. hCNT1 was 83% identical to rCNT1 in amino acid sequence and exhibited the transport characteristics of a Na$^+$-dependent nucleoside transporter with selectivity for pyrimidine nucleosides and adenosine when expressed in Xenopus oocytes. Deoxyadenosine, which undergoes net renal secretion, and guanosine were poor permeants. hCNT1 did, however, transport 3'-azido-3'-deoxythymidine. This is the first demonstration that members of the CNT family exist in human cells and provides evidence of their involvement in the renal transport of physiological nucleosides and nucleoside drugs. The hCNT1 gene was mapped to chromosome 15q25-26.

In a first embodiment, the invention provides substantially pure CNT1 characterized by having a molecular weight of about 71 kD as determined by reducing SDS-PAGE and having essentially the amino acid sequence shown in FIGS. 1 and 7 (rat and human, respectively). The term "substantially pure" as used herein refers to CNT1 which is substantially free of other proteins, lipids, carbohydrates or other materials with which it is naturally associated. One skilled in the art can purify CNT1 using standard techniques for protein purification. The substantially pure polypeptide will yield a single major band on a non-reducing polyacrylamide gel. The purity of the CNT1 polypeptide can also be determined by amino-terminal amino acid sequence analysis. CNT1 polypeptide includes functional fragments of the polypeptide, as long as the activity of CNT1 remains. Smaller peptides containing the biological activity of CNT1 are included in the invention.

The invention provides polynucleotides encoding the CNT1 protein. These polynucleotides include DNA, cDNA and RNA sequences which encode CNT1. It is understood that all polynucleotides encoding all or a portion of CNT1 are also included -herein, as long as they encode a polypeptide with CNT1 activity. Such polynucleotides include naturally occurring, synthetic, and intentionally manipulated polynucleotides. For example, CNT1 polynucleotide may be subjected to site-directed mutagenesis. The polynucleotide sequence for CNT1 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of CNT1 polypeptide encoded by the nucleotide sequence is functionally unchanged.

Specifically disclosed herein is a DNA sequence encoding the rat and human CNT1 genes. The 2420-bp nucleoside transporter cDNA, identified as pQQH1, has an open reading frame encoding a 648-amino acid protein with a relative molecular mass of 71,000. The protein has been named concentrative nucleoside transporter (CNT1). The nucleotide sequence of pQQH1 and the deduced amino acid sequence are shown in FIG. 1. The open reading frame of pQQH1 is flanked by ~170 bp of 5'-untranslated sequence and ~300 bp of 3'-untranslated sequence. The start of the coding sequence is defined by the first ATG downstream of four in-frame stop codons. CNT1 is an integral membrane protein located in the cell plasma membrane. Its amino terminus is predicted to be endofacial rather than exofacial.

The protein has three potential N-linked glycosylation sites (asparagine residues 543, 605, and 643), four potential protein kinase C-dependent phosphorylation sites (residues 5, 203, 421 and 527), and a cluster of 4 serines at residues 609–612. Hydropathy/charge-bias analysis (von Heijne, 1992) of the amino acid sequence predicts a topographical model of CNT1 with 14 potential transmembrane segments (FIG. 2). The protein has a relatively high cysteine content (3.1%). Serine clusters also occur in mammalian $Na^+/K^+$-dependent glutamate transporters (Kanai et al, 1993) and acetylcholine and biogenic amine receptors (Wang et al, 1991).

Potential transmembrane domains were identified using physiochemical (Goldman, Engelman, Steitz) and statistical (von Heijne) hydropathy scales and a 21-residue trapezoid sliding window (von Heijne, 1992). The topographical model shown has the maximum number of 14 potential transmembrane segments and a (+)-charge difference of 21 (von Heijne, 1992). Assignments for the termini of the membrane-spanning domains are those predicted by the von Heijne hydropathy scale. A panel of other hydropathy analyses (Turner and Weiner, 1993) predicted the presence of between 10 and 24 transmembrane domains, so that alternative secondary structures are conceivable. A search of DNA and protein sequence data bases revealed significant sequence similarity between CNT1 and the nupC_ECOLI proton/pyrimidine nucleoside symporter of E. coli (Munch-Petersen and Mygind, 1983) and between these proteins and two E. coli sequences of unknown function (ECOHU4748 and ECOHU4751). (Codes for identifying the sequences are those from the OWL protein sequence data base (Bleasby and Wootton, 1990). CNT1 is 27% identical in amino acid sequence to nupC and 34% identical to ECOHU4748 and ECOHU4751. The similarity was particularly evident in the carboxyl-terminal half of the CNT1 sequence. In contrast, no sequence similarity was found between CNT1 and proteins of mammalian origin, including $Na^+/Cl^-$-dependent and $Na^+/K^+$-dependent amino acid/neurotransmitter transporters (Kanai et al, 1993; Amara and Kuhar, 1993) and the $Na^+$ dependent glucose transporter (SGLT) family (Hediger et al, 1987). The latter includes a putative $Na^+$-linked nucleoside transporter cDNA isolated from rabbit kidney (SNST1)(Pajor and Wright, 1992). Message for SNST1, which induces only modest increases in uridine transport activity in Xenopus oocytes, is absent from rabbit intestine but present in heart, a tissue that has not previously been shown to express $Na^+$-dependent nucleoside transport activity.

The polynucleotide encoding CNT1 includes the sequences in FIGS. 1 and 7 as well as nucleic acid sequences complementary to the sequences in FIGS. 1 and 7. A complementary sequence may include an antisense nucleotide. When the sequence is RNA, the deoxynucleotides A, G, C, and T is replaced by ribonucleotides A, G, C, and U, respectively. Also included in the invention are fragments of the above-described iL nucleic acid sequences that are at least 15 bases in length, which is sufficient to permit the fragment to selectively hybridize to DNA that encodes the protein of FIGS. 1 and 7 under physiological conditions. Specifically, the fragments should hybridize to DNA encoding CNT1 protein under stringent conditions. Fragments of CNT1 are useful for isolating other CNT1 polynucleotides.

Minor modifications of the CNT1 primary amino acid sequence may result in proteins which have substantially equivalent activity as compared to the CNT1 polypeptide described herein. Such proteins include those as defined by the term "having essentially the amino acid sequence of FIGS. 1 or 7". Such modifications may be deliberate, as by site-directed mutagenesis, or may be spontaneous. All of the polypeptides produced by these modifications are included herein as long as the biological activity of CNT1 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for CNT1 biological activity.

The nucleotide sequence encoding the CNT1 polypeptide of the invention includes the disclosed sequences (FIGS. 1 or 7; SEQ ID NO. 1, 2, 3, 7 and 8), and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

CNT1-specific oligonucleotide probes representing the entire CNT1 coding sequence, or variants or fragments thereof, may be used in hybridization or PCR (polymerase chain reaction) protocols to isolate cDNAs encoding structurally-related transport proteins with similar or different funtional properties from rat or their homologues from other species using techniques known to those skilled in the art (e. g. as described in Molecular Cloning—A Laboratory Manual (2nd Edition), Sambrook, J., Fritsch, E. F & Maniatis, T. Cold Spring Harbor Laboratory Press (1989); PCT Protocols—A Guide to Methods and Applications, Innis, M. A., Gelfand, D. H., Sninsky, J. J. & White, T. J. Academic Press, Inc. 1990). Using these methods, it has been demonstrated that a homologue of CNT1 is present in human kidney. DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the CNT1 polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of MRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989).

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. An example of progressively higher stringency conditions is as follows: 2× SSC/0.1% SDS at about room temperature (hybridization conditions); 0.2× SSC/0.1% SDS at about room temperature (low stringency conditions); 0.2× SSC/0.1% SDS at about 42° C. (moderate stringency conditions); and 0.1× SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The development of specific DNA sequences encoding CNT1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of MRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of MRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt 11, can be screened indirectly for CNT1 peptides having at least one epitope, using antibodies specific for CNT1. Such antibodies can be either polyclonally or monoclonally derived and used to detect expression product indicative of the presence of CNT1 cDNA.

DNA sequences encoding CNT1 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the CNT1 polynucleotide sequences may be inserted into a recombinant expression vector. The term "recombinant expression vector" refers to a plasmid, virus or other vehicle known in the art that has been manipulated by insertion or incorporation of the CNT1 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding CNT1 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the CNT1 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The CNT1 polypeptides of the invention can also be used to produce antibodies which are immunoreactive or bind to epitopes of the CNT1 polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, N.Y. (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the CNT1 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

For purposes of the invention, an antibody or nucleic acid probe specific for CNT1 may be used to detect CNT1 polypeptide (using antibody) or polynucleotide (using nucleic acid probe) in biological tissues or fluids. The invention provides a method for detecting a cell proliferative disorder of cardiac tissue or neural tissue, for example, which comprises contacting an anti-CNT1 antibody or nucleic acid probe with a cell suspected of having a CNT1 associated disorder and detecting binding of CNT1 antigen or mRNA to the antibody or nucleic acid probe, respectively. The antibody or nucleic acid probe reactive with CNT1 is preferably labeled with a compound which allows detection of binding to CNT1. Any specimen containing a detectable amount of antigen can be used. The level of CNT1 in the suspect cell can be compared with the level in a normal cell to determine whether the subject has a CNT1-associated cell proliferative disorder. Preferably the subject is human.

When the cell component is nucleic acid, it may be necessary to amplify the nucleic acid prior to binding with an CNT1 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and 56Fe.

The monoclonal antibodies or polynucleotides of the invention can be used in vitro and in vivo to monitor the course of amelioration of a CNT1-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the CNT1-associated disease is effective. The term "ameliorate" denotes a lessening of the detrimental effect of the CNT1-associated disease in the subject receiving therapy.

Figure 5:
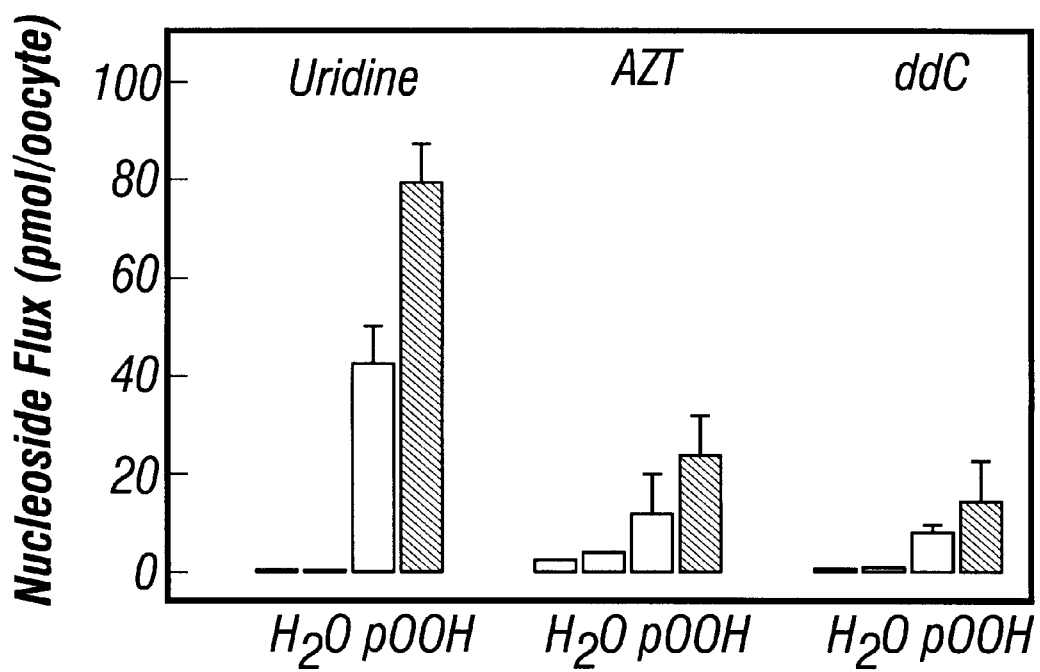
FIG. 5 shows uptake of uridine, AZT and ddC into Xenopus oocytes.

The present invention also demonstrates functional expression of cDNA pQQH1 as shown in FIGS. 3 and 5 and described in Example 2. $^3$[H] Uridine uptake (10 μM, 20° C.) by Xenopus oocytes micro-injected with pQQH1 cRNA is shown in FIG. 3a. After 30 min, the cellular content of uridine, which is only slowly metabolized by oocytes (Huang et al, 1993), was 64 pmol/oocyte, corresponding to an intra-cellular concentration approximately 6-fold higher than that present in the extracellular medium. Uridine uptake (30 min) in water-injected cells was 0.03 pmol-oocyte, giving an expressed: basal flux ratio in excess of 20,000. In subsequent experiments, a 1-min incubation period was used to define initial rates of uridine transport (FIG. 3a, inset). The expressed transport activity was saturable with an apparent $K_m$ of 37 μM (FIG. 3b), which is within the range for Na$^+$-dependent uridine transport in intact mammalian cells and vesicle preparations (Vijayalakshimi and Belt, 1988; Jarvis, 1989; Roden et al, 1991; Lee et al, 1990; Williams and Jarvis, 1991; Gutierrez and Giacomini, 1993; Wu et al, 1992; Belt et al, 1993). The $V_{max}$ was 21 pmol/oocyte-min$^{-1}$. Na$^+$-independent uridine influx in cRNA-injected oocytes was 3.6-fold greater than uridine influx in water-injected oocytes in Na$^+$ medium; the latter may represent uncoupled uridine transport (slippage) by the transporter (Huang et al, 1993; Stein, 1986). The possibility that CNT1 might be C$^-$-dependent was tested in ion-substitution experiments in which Cl$^-$ in the transport buffer was substituted by gluconate. To permit complete Cl$^-$-replacement, the normal transport buffer was simplified to contain only NaCl or sodium gluconate (100 mM) and 10 mM HEPES, pH 7.6. Omission of KCl, CaCl$_2$, and MgCl$_2$ from the medium had no significant effect on the initial rate of uridine uptake, and the flux was unaffected by substitution of Cl$^-$ by gluconate.

Figure 3A:
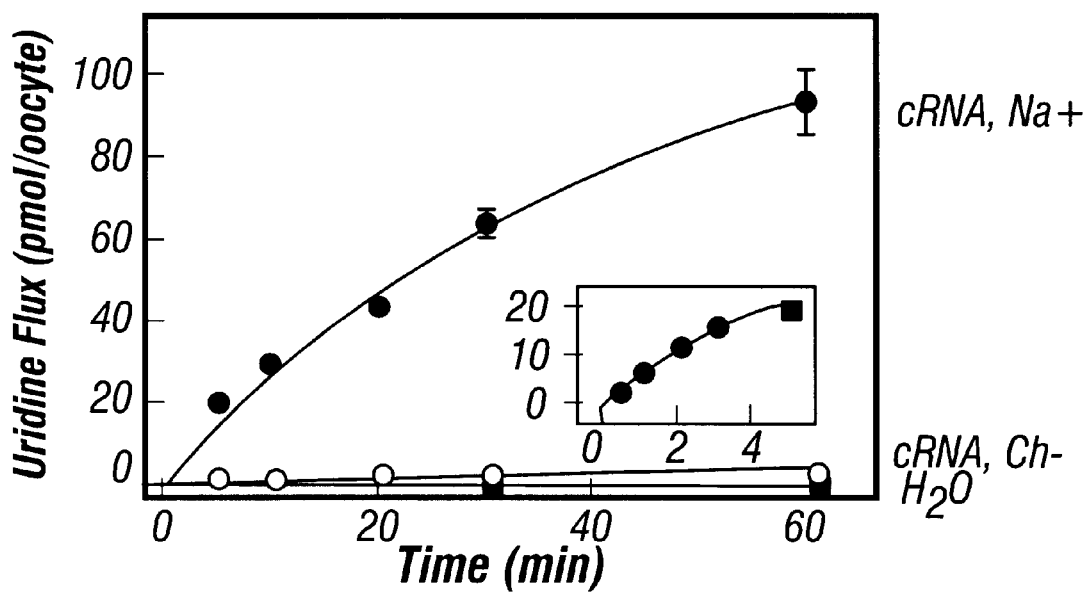
FIG. 3 shows expression of CNT1 in Xenopus oocytes. Panel a: time course of uridine uptake (10 μM, 20° C.). Oocytes were injected with water or RNA transcribed in vitro from the nucleoside transporter cDNA (pQQH1). Each value represents the mean ±S.E. of 8–10 oocytes. The inset shows a time course of uridine uptake by cRNA-injected oocytes in $Na^+$ medium measured from 30 s to 5 min. Panel b: concentration dependence of pQQH1-mediated uridine influx. Apparent $K_m$ and $V_{max}$ values were determined by non-linear regression analysis (ENZFITTER, Elsevier-Biosoft). Panel c: specificity of pQQH1-mediated uridine influx (T, thymidine; C, cytidine; G, guanosine; I, inosine; A, adenosine; U, uridine). Panel d: thymidine transport in oocytes injected with pQQH1 cRNA. For panels c and d, the permeant concentration was 10 μM and competing nonradioactive nucleosides were present at a concentration of 1 mM. Fluxes were not corrected for the small (<0.1%) contribution of endogenous activity.
Figure 3B:
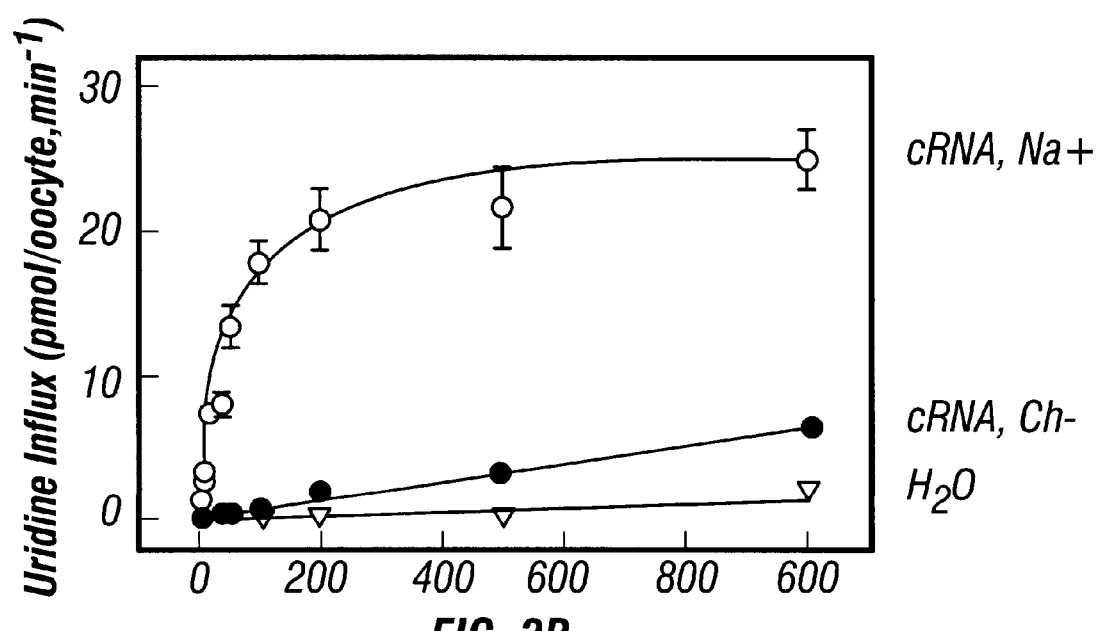
Figure 3C:
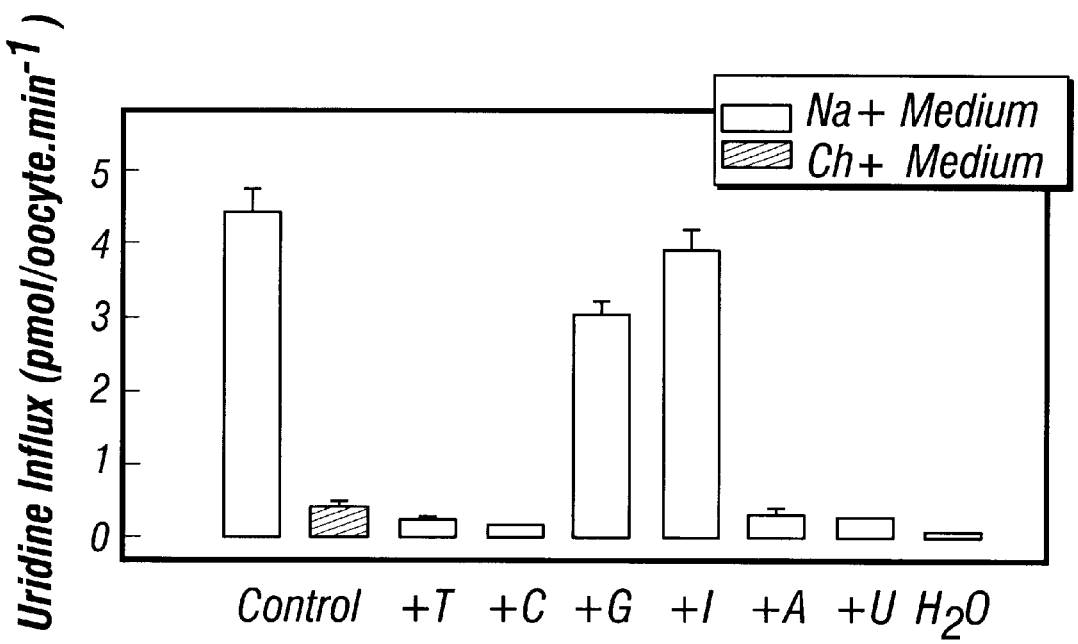
Figure 3D:
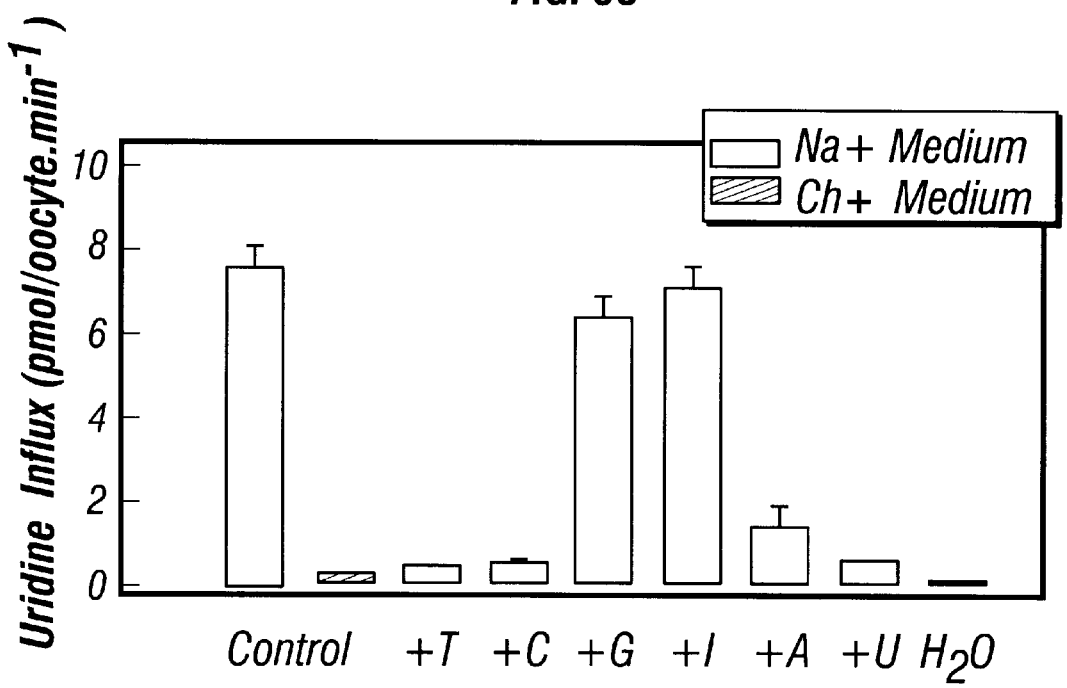

Unlike some Na$^+$-dependent amino acid-neurotransmitter transporters (Amara and Kuhar, 1993), CNT1 does not require Cl$^-$0 ions for activity. Transport was unaffected by 1 μM NBMPR. All three Na$^+$-dependent nucleoside transporters (cif, cit and cib) are expressed in oocytes injected with intestinal mRNA (Huang et al, 1993; Jarvis and Griffith, 1991; Terasaki et al, 1993). Inhibition experiments identified CNT1-mediated uridine transport activity as cit-type (FIG. 3c). The model system cit permeant thymidine gave similar results (FIG. 3d). Uracil, UMP, UDP, and UTP (1 mM) had no effect on expressed uridine fluxes.

Figure 4A:
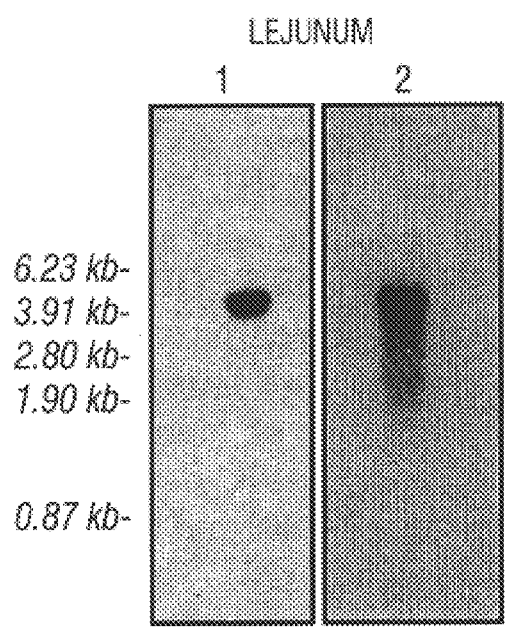
FIG. 4 shows the results of a high stringency Northern analysis of MRNA from rat tissues probed with $^{32}$P-labeled CNT1 cDNA. Panel a: rat jejunal MRNA probed with radiolabeled coding sequences of CNT1 corresponding to amino acid residues 75–213 (lane 1) or 385–588 (lane 2). Arrows indicate the positions of two bands (1.9 and 2.5 kb) visible on the original autoradiogram. Panel b: a multiple rat tissue blot probed with the CNT1 75–213-amino acid residue coding sequence.
Figure 4B:
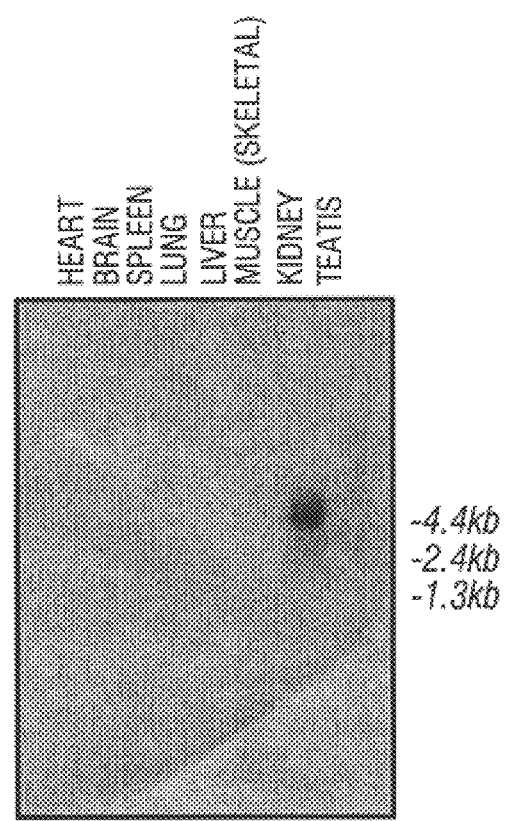

Hybridization of rat jejunal mRNA at high stringency with a radiolabeled probe of CNT1 corresponding to amino acid residues 75–213 identified a single transcript at 3.4 kb (FIG. 4a, lane 1). A Northern blot at the same level of stringency with a different CNT1 probe representing amino acid residues (385–588) closer to the carboxyl terminus of the protein revealed additional transcripts in the 1.5–3.0-kb range, including bands at 1.9 and 25 kb that might possibly encode other related rat intestinal Na$^+$-dependent nucleoside transporters (FIG. 4a, lane 2)(Huang et al, 1993). When a rat multiple tissue Northern blot was screened at high stringency with the 385–588-amino acid residue CNT1 probe, only kidney gave a positive hybridization signal (FIG. 4b). System cit transport activity has only been demonstrated definitively in intestinal and kidney epithelia (Vijayalakshimi and Belt, 1988; Lee et al, 1990; Williams and Jarvis, 1991.

Two pyrimidine nucleoside analogs (AZT and ddC) are used to treat AIDS. AZT is absorbed efficiently by the gastrointestinal systems of humans and rats (Melvin et al, 1990), and both AZT and ddC are administered orally. Plasma concentrations of AZT (therapeutic range 6–10 μM) are determined primarily by intestinal absorption and not by drug elimination (Melvin et al, 1990). AZT inhibited cit-mediated uridine transport in oocytes injected with rabbit intestinal mRNA (Terasaki et al, 1993), suggesting that it might be a substrate of the cit transporter. For CNT1, uridine transport (10 μM) was inhibited by both AZT and ddC (IC$_{50}$ values <1 mM), while ddI and ddG (1 mM) had no effect. Oocytes injected with pQQH1 cRNA showed large increases in [$^3$H]AZT and [$^3$H]ddC (10 μM) uptake compared to water-injected controls, demonstrating substantial CNT1-mediated transport of both nucleoside analogs (FIG. 5). Fluxes in water-injected oocytes, which reflect primarily nonfacilitated diffusion (Huang et al, 1993), were greater for AZT than for ddC or uridine. Initial rates (10-min flux) of expressed AZT and ddC uptake (10 μM) were 77 and 93% Na$^+$ dependent and inhibited >95% by uridine (1 mM). Rate versus concentration studies for AZT and ddC (not shown) yielded apparent $K_m$ values of 0.49 and 0.51 mM, respectively ($V_{max}$ 28 and 20 pmol/oocyte.min$^{-1}$). These apparent affinities are within the range of anticipated luminal concentrations of AZT and ddC during oral administration and suggest a role for CNT1 in their intestinal absorption. While ddC has previously been shown (Domin et al, 1993) to be a substrate of the human erythrocyte es transporter ($K_m$ 23 mM), this is the first direct demonstration of mediated transport of AZT. CNT1 may also contribute to AZT and ddC transport in the kidney (FIG. 4).

In addition to physiological nucleosides, therefore, CNT1 was found to transport the antiviral pyrimidine nucleoside analogs AZT and ddC. Most previous studies of AZT and ddC membrane permeability have focused on nonepithelial cells. AZT is not transported by equilibrative nucleoside transporters and enters human erythrocytes, lymphocytes, macrophages, and bone marrow progenitor cells mainly by nonfacilitated diffusion (Zimmerman et al, 1987; Chan et al, 1992; Chan et al, 1993). ddC is a low affinity es substrate (Ullman, 1989; Domin et al, 1993). Rates of entry of AZT and ddC into human erythrocytes are much less (<2%) than those of thymidine and cytidine, and it is likely that slow entry of AZT and ddC into HIV-infected cells reduces therapeutic effectiveness. The cloning and expression of CNT1 provides the first direct evidence that AZT permeation in some cell types is mediated.

Nucleosides are translocated across the brush-border and basolateral membranes of intestinal and renal epithelia by Na$^+$-dependent and Na$^+$-independent mechanisms, respectively (Betcher et al. 1990; Gutierrez et al., 1994; Le Hir and Dubach, 1984; Williams et al., 1989). By analogy with the intestinal absorption and renal handling of glucose, these NTs may combine to mediate transepithelial nucleoside fluxes. rCNT1 and rCNT2 (Che et al., 1995; Yao et al. unpublished), which are expressed in jejunum/kidney and jejunum/liver, respectively, are the first recognized mammalian representatives of a new transporter gene family that includes E. coli and other bacterial nupC proton/nucleoside symporters (Che et al. 1995; Craig et al. 11994). rCNT1 and rCNT2 are selective for pyrimidine and purine nucleosides, respectively, and correspond functionally to the two major Na$^+$-dependent NT processes that have been observed in mammalian cells of rodent, rabbit and bovine origin (Cass, 1995).

hCNT1a—Plasmid pMHK1 is a composite full-length cDNA assembled from two incomplete, overlapping cDNAs cloned by hybridization screening of a human kidney cDNA library. The open reading frame encoded a 650 amino acid residue protein (compared with 648 for rCNT1) that was 83% identical in sequence to rCNT1 (FIG. 8) and was designated hCNT1a. The sequence identity between hCNT1a and rat liver rCNT2 (SPNT) (Che et al. 1995) was 72% (FIG. 8). Northern blot analysis of human kidney mRNA identified a single transcript at 3.4-kb. The rat kidney rCNT1 transcript was of similar size.

Figure 9:
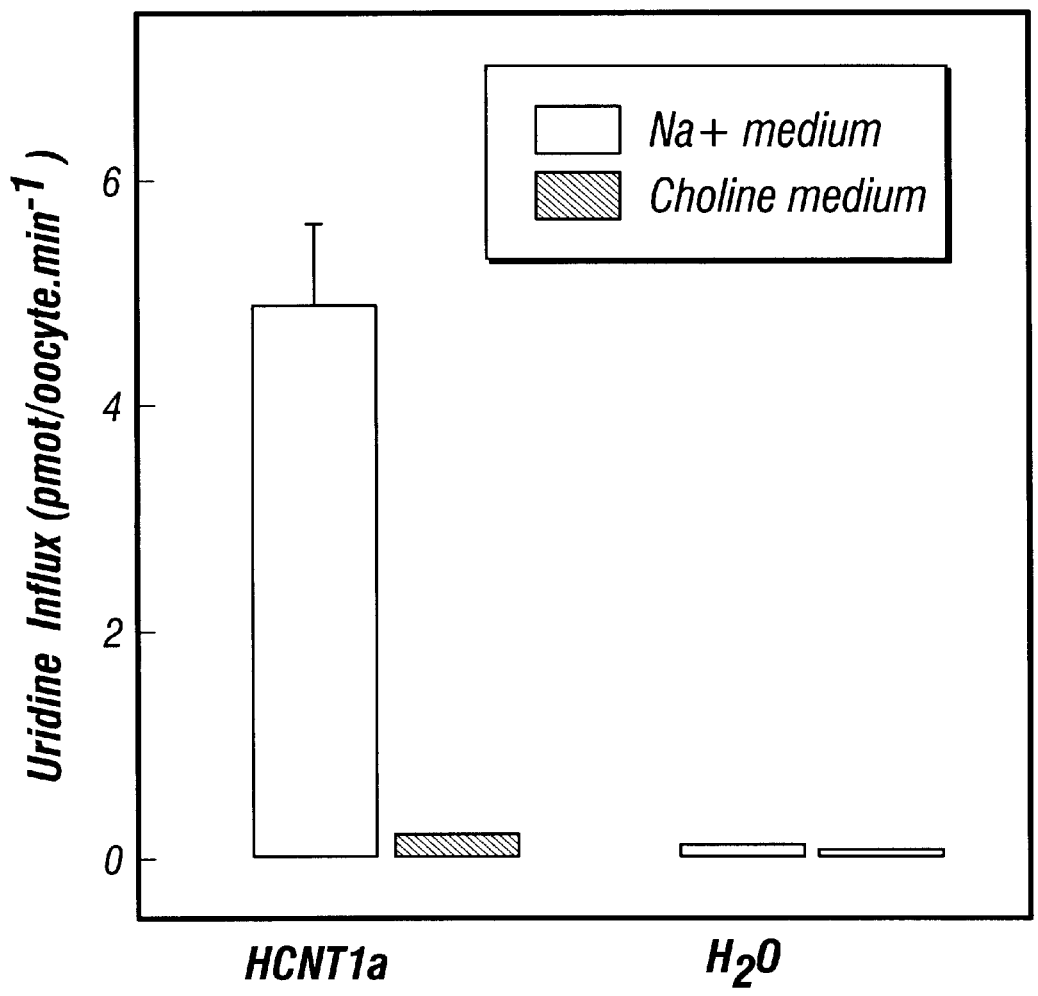
FIG. 9 shows expression of hCNT1a in Xenopus oocytes. Oocytes were injected with either water alone or water containing hCNT1a RNA transcript. Influx of [$^3$H]uridine (10 μM) was determined in transport buffer containing 100 mM NaCl or 100 mM choline chloride.

Uptake of [$^3$H]uridine (10 $\mu$M) by Xenopus oocytes injected with hCNT1a transcript was rapid and $Na^+$-dependent (4.88±0.70 and 0.18±0.01 pmol/oocyte.min$^{-1}$ in $Na^+$-medium and choline-medium, respectively) (FIG. 9). In $Na^+$-medium, uridine influx in control water-injected oocytes was only 0.07±0.01 pmol/oocyte.min$^{-1}$, giving an expressed:basal flux ratio of 69:1. This uridine flux was similar to that reported previously for rCNT1.

hCNT1b—Plasmids pMHK2–pMHK4 were three randomly selected hCNT1 clones isolated by RT-PCR amplification of human kidney RNA using primers flanking the pMHK1 open reading frame. Their predicted amino acid sequences were similar (>99% correspondence), but not identical, to that of hCNT1a (pMHK1) (FIG. 10). Three amino acid substitutions (G34E [codons GGA or GAA], V1901 [codons GTC or ATC], D522N [codons GAC or AAC) and deletion of V141 were present in the direct RT-PCR sequence (FIG. 10) and may reflect hCNT1 genetic polymorphism (pMHK1 and pMHK2–pMHK4 were derived from different human donors). Other differences unique to one or two of the RT-PCR clones most likely represented PCR-induced changes. Only one of the three cloned RT-PCR cDNAs (pMHK2) was functional in oocytes. The protein encoded by this cDNA differed from hCNT1a at five positions (the four putative polymorphic sites noted above, plus N41OS [codons AAC or AGC), and was designated hCNT1b. pMHK3 and pMHK4 (inactive) contained stop codons at amino acid positions 9 and 640, respectively. Subsequent experiments investigated the transport characteristics of hCNT1a and hCNT1b.

Figure 11:
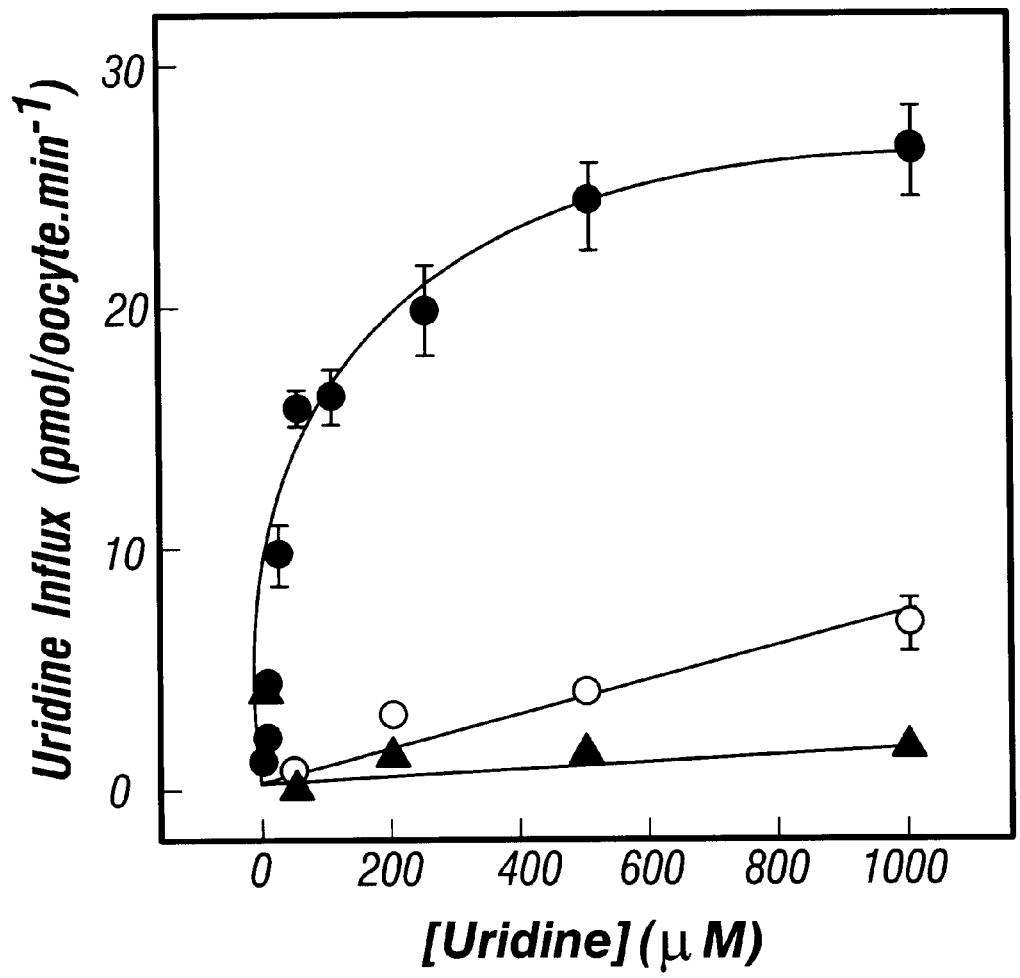
FIG. 11 shows concentration dependence of hCNT1a-mediated uridine influx. Oocytes were injected with either water alone (▲) or water containing hCNT1a RNA transcript (○,●). Influx of [$^3$H]uridine was determined in NaCl (▲,●) or choline chloride (○) transport buffer.

Kinetic properties of recombinant hCNT1a and hCNT1b—hCNT1a-mediated influx of uridine (defined as the difference in uptake between RNA-injected and water-injected oocytes) was saturable, with an apparent $K_m$ value of 45±8 $\mu$M and a $V_{max}$ of 26±1 pmol/oocyte.min$^{-1}$ (FIG. 11). Similar kinetic constants were obtained for hCNT1b: apparent Km 37±10 $\mu$M; $V_{max}$ 22±2 pmol/oocyte.min$^{-1}$ (concentration-dependence curve not shown). These apparent $K_m$ values are within the range of those reported for $Na^+$-dependent uridine transport in intact mammalian cells and vesicle preparations (Cass, 1995). An apparent $K_m$ value of 37 $\mu$M and a $V_{max}$ value of 21 pmol/oocyte.min$^{-1}$ were determined previously for recombinant rCNT1 produced in Xenopus oocytes under similar conditions. The three recombinant transporters were therefore functionally indistinguishable with respect to the kinetics of uridine influx.

$Na^+$-independent uridine influx by hCNT1a exhibited a linear concentration-dependence that was 5.9-fold greater than the uridine flux in water-injected oocytes in $Na^+$-medium (0.81±0.14 and 0.14±0.01 pmol/oocyte.min$^{-1}$ at 50 $\mu$M uridine, respectively)(FIG. 11). This difference is consistent with previous observations for recombinant rCNT1 in the oocyte expression system and suggests ordered binding of $Na^+$ and nucleoside to the transporter, with the cation binding first, thereby increasing the protein's affinity for nucleosides.

Figure 12A:
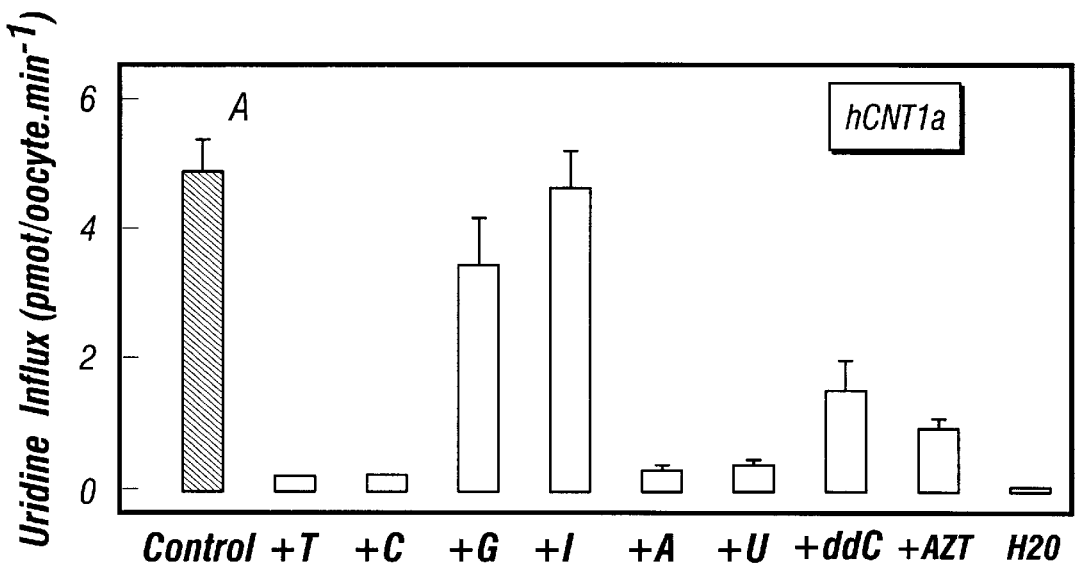
FIG. 12 illustrates the nucleoside specificity of hCNT1a (A) and hCNT1b (B). [$^3$H]Uridine influx (10 μM) was measured in hCNT1a and hCNT1b RNA transcript-injected oocytes in the absence (control) or presence of 1 mM of the nonradioactive physiological nucleosides (T, thymidine; C, cytidine; G, guanosine; I, inosine; A, adenosine; U, uridine) or 5 mM of the antiviral nucleoside analogs AZT and ddC. H$_2$O, water-injected oocytes. Fluxes were not corrected for the contribution of endogenous transport activity.

Permeant selectivity of recombinant hCNT1a and hCNT1b—Classification of rCNT1 as a pyrimidine-selective NT was based upon selective inhibition of uridine and thymidine fluxes by pyrimidine nucleosides and adenosine (adenosine, thymidine, cytidine, uridine>>guanosine, inosine). In FIGS. 12A and B, uridine fluxes in oocytes expressing recombinant hCNT1a and hCNT1b were inhibited by adenosine, thymidine, cytidine and uridine, but not by guanosine and inosine, suggesting close functional homology of both human NTs with rCNT1.

Transport of adenosine and deoxyadenosine—Recombinant rCNT1 transports adenosine with the same high affinity as uridine, but with a lower $V_{max}$ (Fang et al, 1996, Yao et al. unpublished). Consistent with these findings, adenosine blocked hCNT1a-mediated influx of uridine (10 $\mu$M) (FIG. 13) with a calculated apparent $K_i$ value of 50±11 $\mu$M (determined assuming competitive inhibition and a uridine apparent $K_m$ of 45 $\mu$M). The corresponding inhibition constant for recombinant rCNT1 was 29 $\mu$M (Yao et al. unpublished).

Mediated fluxes of 10 $\mu$M [$^3$H]adenosine by the human and rat NTs (FIG. 14A) were also similar (0.49±0.03 and 0.51±0.05 pmol/oocyte.10 min$^{-1}$, respectively). To control for possible differences in the production of functional NT protein in this experiment, we also measured corresponding fluxes for 10 $\mu$M uridine, which were 3.68±0.46 and 5.60±0.38 pmol/oocyte.min$^{-1}$ for hCNT1a and rCNT1, respectively, giving uridine:adenosine flux ratios of 75 (hCNT1a) and 110 (rCNT1). Thus, the NTs of both species treated adenosine as a high-affinity, low capacity permeant. In human, mouse and rat kidney, adenosine undergoes a net renal reabsorption by a high affinity, low capacity process (Kuttesch and Nelson, 1982; Trimble and Coulson, 1984). For example, adenosine is reabsorbed at plasma concentrations less than 50 $\mu$M, but is secreted at higher concentrations in isolated perfused rat kidneys (Trimble and Coulson, 1984).

Figure 13:
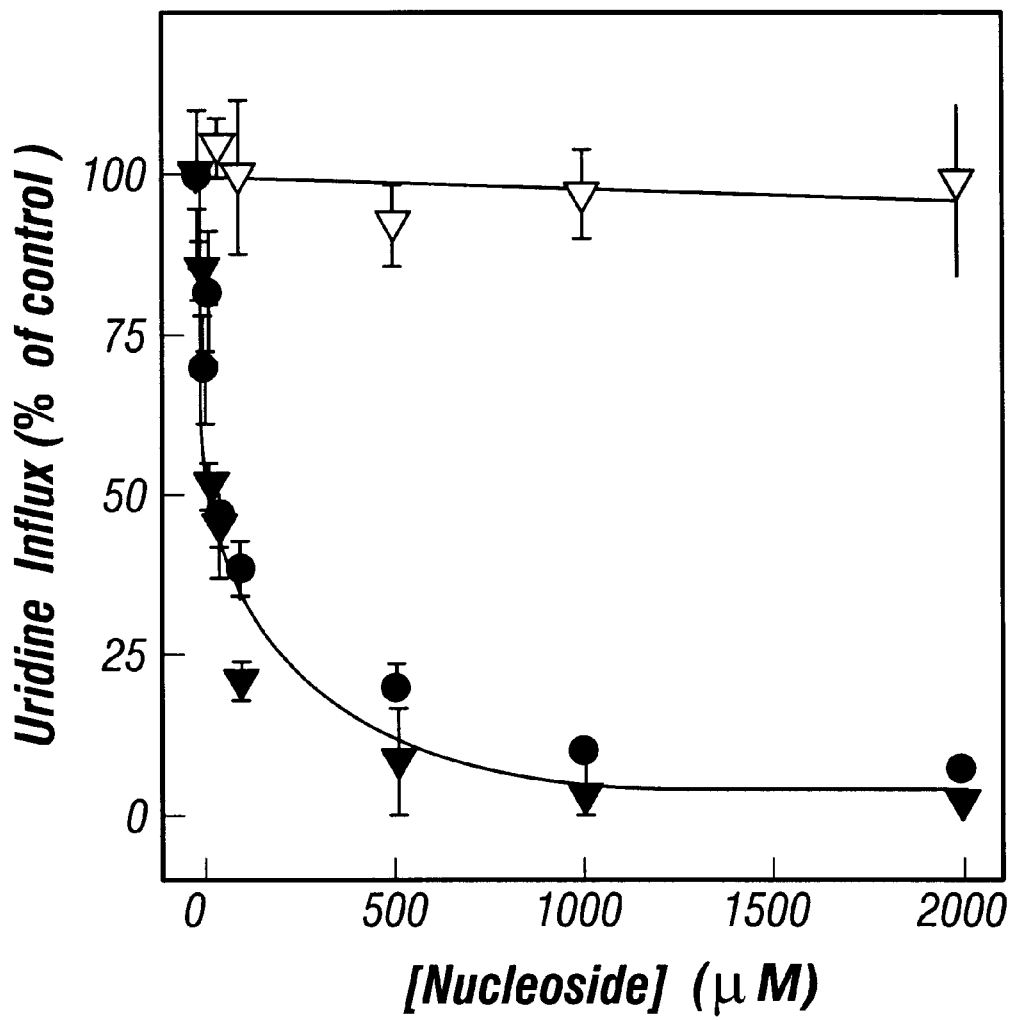
FIG. 13 illustrates the inhibition of hCNT1a-mediated influx of uridine by adenosine, deoxyadenosine and guanosine. [$^3$H]Uridine influx (10μ) was measured in hCNT1a RNA transcript-injected oocytes in the absence or the presence of increasing concentrations (20 μM–21 mM) of nonradioactive adenosine (⊙), deoxyadenosine (▼) guanosine (▽). Fluxes were not corrected for the contribution of endogenous uridine transport activity.

Unlike adenosine, deoxyadenosine undergoes net renal secretion in humans and in mice (Kuttesch and Nelson, 1982). Other sugar-modified adenosine analogs (tubercidin compounds) are also secreted (Nelson et al. 1983). Deoxyadenosine inhibited hCNT1a transport activity with an apparent $K_i$ value (46±14 $\mu$M) similar to that determined for adenosine, demonstrating high affinity binding of deoxyadenosine to the recombinant NT (FIG. 13). Consistent with the kidney's ability to differentiate its handling of adenosine (reabsorption) and deoxyadenosine (secretion), however, transport of deoxyadenosine by hCNT1a and rCNT1 was slower than for adenosine (inset, FIG. 14A). Mediated influx of 10 $\mu$M [$^{14}$C]deoxyadenosine by the human and rat NTs was 0.14±0.02 and 0.11±0.02 pmol/oocyte.10 min$^{-1}$, respectively. Adenosine fluxes (10 $\mu$M) in the same experiment were 0.60±0.01 and 0.70±0.0 pmol/oocyte.10 min$^{-1}$, respectively, giving adenosine:deoxyadenosine flux ratios of 4:1 for hCNT1 and 7:1 for rCNT1. These results establish that the ribose moiety of adenosine is important for transport by hCNT1 and rCNT1 and are compatible with CNT1 participation in renal adenosine reabsorption. The relative contribution of hCNT1 to that process, assuming that the NT is located in the brush border membrane, will depend upon the extent to which human kidney expresses other $Na^+$-linked NTs that accept adenosine.

Figure 14:
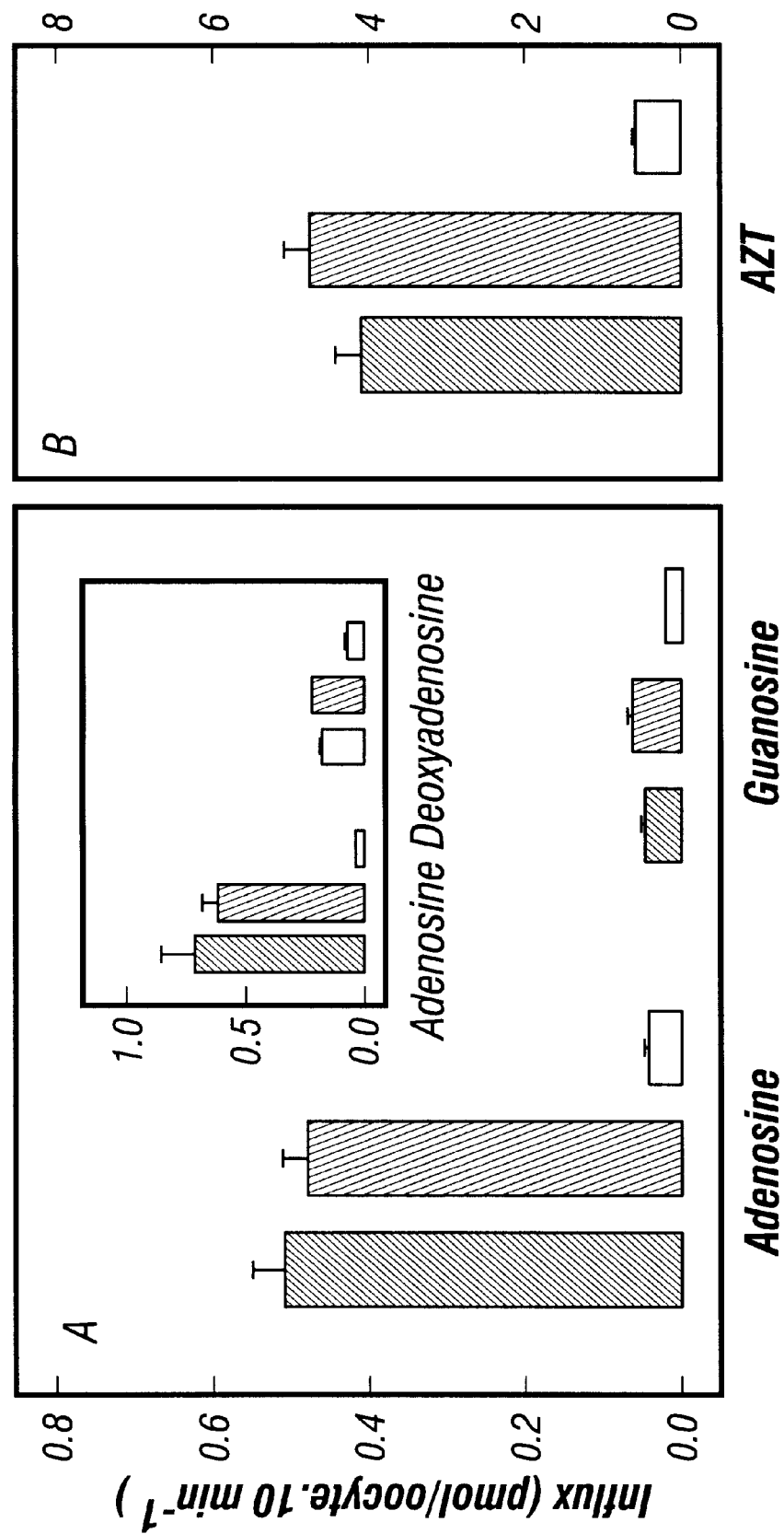
FIG. 14 shows the transport of adenosine, deoxyadenosine and guanosine (μ) and AZT (B) by recombinant hCNT1a and rCNT1. Adenosine, guanosine and AZT (10 μM) fluxes were compared in the same batch of oocytes injected either with water (open columns) or with RNA transcript for hCNT1a or rCNT1 (hatched and solid columns, respectively). The inset to panel A shows results from a separate experiment comparing uptake of adenosine and deoxyadenosine.

Transport of guanosine—Unlike adenosine and deoxyadenosine, hCNT1a transport of uridine was not inhibited by guanosine, a presumed N4/cit permeant (FIG. 13). Measurements of [$^3$H]guanosine fluxes (10 $\mu$M) gave a value for mediated transport of guanosine by hCNT1a (0.06±0.01 pmol/oocyte.10 min$^{-1}$) that was substantially smaller than that determined for adenosine in the same experiment and similar to the guanosine flux for rCNT1 (0.05±0.01 pmol/oocyte.10 min$^{-1}$)(FIG. 14A). Adenosine:guanosine and uridine:guanosine flux ratios for the human NT were 8:1 and 610:1, respectively. Similar very low guanosine fluxes were observed for hCNT1b (results not shown). These data demonstrate that guanosine is a poor CNT1 permeant. Human kidney brush border membrane vesicles (Gutierrez and Giacomini, 1993) and oocytes injected with human kidney MRNA (Gutierrez and Giacomini, 1994) have previously been shown to exhibit an NT activity that accepts pyrimidine nucleosides, adenosine and guanosine as permeants. The role of hCNT1a/b in these processes remains to be determined. The conclusion that guanosine is a permeant of the human kidney pyrimidine-selective NT was based upon results from indirect inhibition and trans-acceleration assays (Gutierrez and Giacomini, 1993; Gutierrez and Giacomini, 1994), and not from direct measurements of [$^3$H]guanosine fluxes.

Transport of AZT—The pyrimidine nucleoside drug AZT is widely used in the treatment of AIDS (Clumeck, 1993). It is administered orally, is absorbed efficiently by the gastrointestinal systems of rats and humans (Clumeck, 1993; Melvin et al. 1990; Park and Mitra, 1992), and is excreted in the urine either unchanged or as the glucuronide conjugate (Good et al. 1990, Griffiths et al. 1992). Recombinant rCNT1 expressed in oocytes transports AZT (Yao et al. in prss), and uptake of [$^3$H]AZT by rat jejunum in vivo is both Na$^+$-dependent and inhibited by uridine.

Figure 12B:
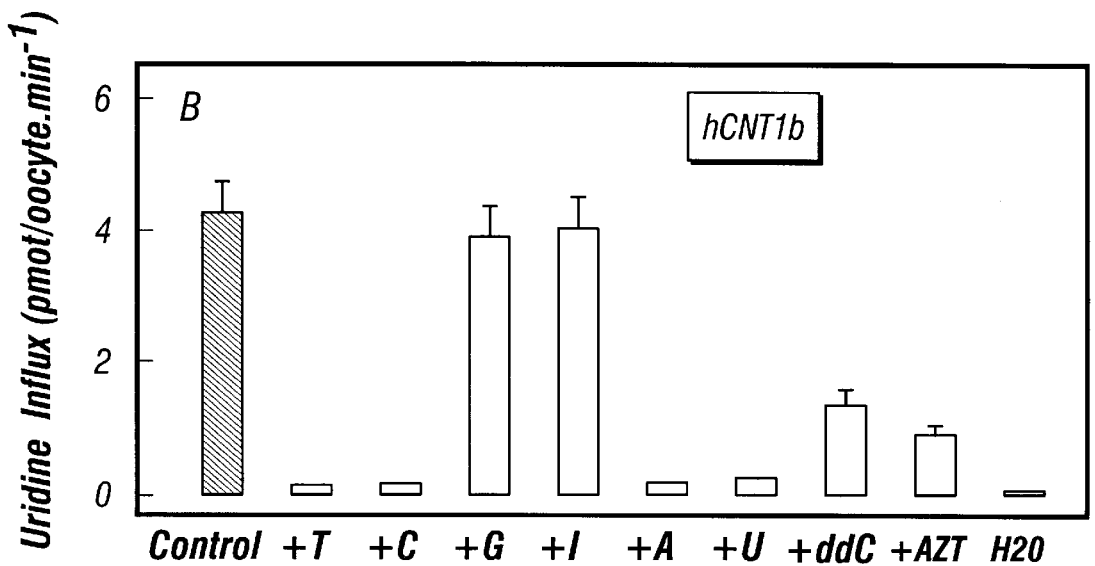

In the present series of experiments, AZT inhibited hCNT1a- and hCNT1b-mediated influx of uridine (FIGS. 12A and 12B). In FIG. 14B, recombinant hCNT1a transported 10 $\mu$M [$^3$H]AZT at a rate similar to rCNT1 (4.79±0.41 and 4.10±0.34 pmol/oocyte.10 min$^{-1}$, respectively). Similar AZT fluxes were observed for hCNT1b (results not shown). Another antiviral pyrimidine nucleoside drug, ddC, also inhibited hCNT1a- and hCNT1b-mediated influx of uridine (FIGS. 12A and 12B), indicating that it also may be a hCNT1 permeant. Therefore, although AZT undergoes net renal secretion (Griffiths et al. 1992), our results demonstrate the existence in human kidney of an active transport system that may contribute to AZT (and ddC) reabsorption.

Figure 15:
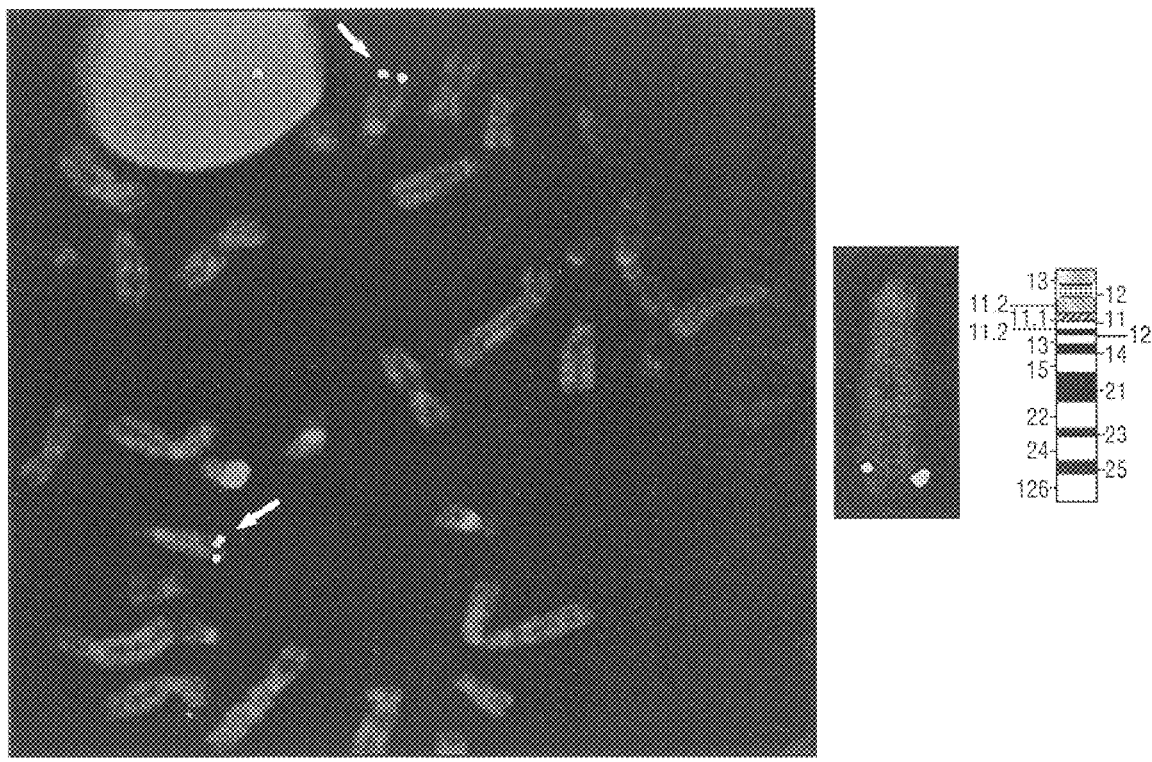
FIG. 15 shows chromosomal mapping of the hCNT1 gene. Separate images of DAPI banded chromosomes and of FITC targeted chromosomes were captured by a thermoelectrically cooled charge coupled camera (Photometrics, Tuscon, Ariz.), overlaid electronically using image analysis software, and pseudo coloured blue (DAPI) and yellow (FTC). The band assignment was determined by measuring the fractional chromosome length and by analyzing the banding pattern generated by the DAPI counterstained image. A DAPI-banded chromosome 15 together with schematic idiogram is shown to indicate that the probe hybridized to q25-26.

Chromosomal localization of the hCNT1 gene—FISH analysis mapped a 2 kb hCNT1a probe to chromosome 15q25-26 (FIG. 15). The same chromosomal band location was determined by screening a human P1-derived artificial chromosome (PAC) library. Three PAC clones were isolated and two mapped exclusively to 15q25-26. The third clone mapped primarily to 15q25-26, but showed cross-hybridization to chromosomes 2 and 11, suggesting that it contained additional repetitive sequence. PCR demonstrated that all of the clones overlapped the majority of the genomic sequence for hCNT1.

The inventors have isolated and expressed human kidney cDNAs encoding structural and functional homologs (hCNT1a and hCNT1b) of rat jejunal/kidney Na-dependent NT rCNT1. Differences in amino acid sequence between hCNT1 a and hCNT1b did not result in differences in nucleoside transport activity and both human NT isoforms mediated Na-dependent fluxes of uridine, AZT and adenosine. Deoxyadenosine, which undergoes net renal secretion, and guanosine were poor hCNT1 permeants. hCNT1 was localized to chromosome 15q25-26 and represents a potential mechanism for renal reabsorption of physiological nucleosides and synthetic nucleoside drugs.

The invention further provides methods based on the use of this novel cDNA sequence in association with currently available technologies known to those skilled in the art, for example methods for expressing the cDNA to produce the encoded protein, for raising antibodies to the expressed protein, for designing new nucleoside drugs and new nucleoside transport inhibitor drugs and screening potential drug candidates for efficacy, for development of CNT-specific oligonucleotide and antibody probes and use of these probes to isolate further CNT genes, for development of CNT-specific inhibitors, for cellular targeting of therapeutic nucleotides, for gene therapy of cancer and viral diseases and for clinical and research applications of CNT-specific oligonucleotide and antibody probes.

The Xenopus oocyte expression system described herein provides a screening assay system to identify compounds which inhibit or stimulate CNT1-mediated nucleoside fluxes. Compounds of interest are applied to Xenopus oocytes and nucleoside fluxes determined as described above.

In another embodiment, the invention provides a method for identifying a composition which affects CNT1 activity. The method includes using cells which functionally express CNT1 or CNT1 to screen drugs. Cells which functionally express CNT1 or CNT1 can also be used to screen potential inhibitors or inducers (stimulators) of CNT1 activity. The method includes incubating components comprising the composition and CNT1 under conditions sufficient to allow the components to interact and measuring the effect of the composition on the transporter or the polynucleotide encoding the transporter. Compositions that affect CNT1 include peptides, peptidomimetics, polypeptides, chemical compounds and biologic agents.

Incubating includes conditions which allow contact between the test composition and CNT1. Contacting includes in solution and in solid phase. The test composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008–1012, 1985), allele-specific oligonucleotide (ASO) probe analysis (Conner, et al., *Proc. Natl. Acad. Sci. USA,* 80:278, 1983), oligonucleotide ligation assays (OLAs) (Landegren, et al., *Science,* 241:1077, 1988), and the like. Molecular techniques for DNA analysis have been reviewed (Landegren, et al., *Science,* 242:229–237, 1988).

Also included in the screening method of the invention is combinatorial chemistry methods for identifying chemical compounds that affect CNT1.

The same expression system provides a screening assay for compounds which are potential new CNT1 (system cit) permeants, as exemplified by the studies of AZT and ddC described above and shown in FIG. 5. Oocytes injected with water or in vitro transcribed RNA from pQQH1 were incubated with radiolabeled permanent (10 $\mu$M) for 30 min (open columns) or 1 h (hatched columns) at 20° C. Each value represents the mean ±S. E. of 8–10 ooctyes. Similarly, the expression system can be used to determine the transport characteristics (kinetic parameters) of new permeants or inhibitors and to assess the effects of changes in nucleoside structure on these parameters as in FIG. 3b.

As will be understood by those skilled in the/ art, other suitable expression systems may be similarly employed; for example, nucleoside transport-deficient COS-7 cells may be prepared using the protocol of Crawford et al, (1990), J. Biol. Chem., v. 265, pp. 13730–734) and transfected with CNT1 cDNA constructs to produce transient and stable transfectants e. g. by the procedure of Matthews, K. E., Mills, G. B., Horsfall, W., Hack, N., Skoreeki, K. & Keating, A. (1993) Exptl. Hematol. 21:697–702. Alternatively, native COS-7 cells (or other appropriate cell type) may be transfected and CNT1-mediated transport activity assayed in the presence of NBMPR and/or dipyridamole to block endogenous es and ei transport activity.

CNT1 oligonucleotide and antibody probes will have application in studies of nucleoside physiology and pharmacology allowing, for example, analysis of the distribution, amounts and regulation of transport protein in normal cells and tissues and in pathologic (eg. neoplastic) states. Such information, together with the development of transport inhibitors and nucleoside drugs specific for different nucleoside transporter subtypes) will allow cellular targeting of therapeutic nucleosides.

The purified polypeptide or fragments; or purified polynucleotide or fragments thereof can be used to study three-dimensional molecular docking of compounds or compositions. The methods and computer programs for molecular docking are known to those skilled in the art. The results from these studies will be useful for the design of compounds or compositions which can modulate nucleoside transport.

Some gene therapy strategies for in vivo delivery of therapeutic genes are described in Toshiyoshi, F., Grimm, A. & Roth, J. A. (1994) Curr. Opinion Oncol. 6:96–105. These methods may be employed to accomplish gene therapy with the CNT1 gene and related genes.

Without further elaboration, it is believed that one skilled in the art can, using the preceding description, utilize the present invention to its fullest extent. The following examples are illustrative only, and not limiting of the remainder of the disclosure in any way whatsoever.

EXAMPLES

Example 1 cDNA Cloning and Sequencing—A rat jejunum poly(A)+ RNA(mRNA) size fraction (median 2.3 kb) that induced peak Na+-dependent uridine transport activity (Huang et al, 1993) was reverse transcribed using the Rioboclone (Promega) cDNA synthesis system with an Xba primer adaptor consisting of oligo(dT) adjacent to an XbaI restriction site. Digestion of the resulting double-stranded cDNA with XbaI gave orientation-specific DNA with a 5' EcoRI terminus and a 3' XbaI terminus. cDNAs≧2 kb were ligated into the EcoRI and XbaI restriction enzyme sites of the plasmid expression vector pGEM-3Z (Promega) and transformed into *Escherichia coli* (JM 109) to give a cDNA library containing 6,800 primary recombinants. Plasmid DNA was transcribed in vitro from 20 pools of ~700 clones, and the resulting cRNA was injected into oocytes. Two pools were identified that increased the uptake of 10 μM uridine 8-fold above that of oocytes injected with cRNA transcribed from the total library and 140-fold above that of control water-injected oocytes. Colonies from the master plate of one of these pools were individually seeded into the wells of 96-well flat-bottom microtiter plates to produce a grid system. Testing of rows and columns for uridine transport activity identified a single positive colony from which we isolated a plasmid (pQQH1) with a 2.4-kb insert. The insert was sequenced in both directions by overlapping deletions generated by exonuclease III (Erase-a-base System, Promega) and verified by sequencing with synthetic oligonucleotides. Sequencing by the dideoxynucleotide chain termination method was performed by Taq DyeDeoxy terminator cycle sequencing with an automated Model 373A DNA Sequencer (Applied Biosystems, Inc.).

Example 2

Expression of cNT1 in Oocytes-Plasmid pQQH1 DNA was linearized with XbaI and transcribed with T7 polymerase in the presence of the m$^7$GpppG cap using the MEGAscript (Ambion) transcription system. Remaining template was removed by digestion with RQ1 DNase. Oocytes were treated with collagenase to remove follicular layers (Huang et al, 1993) and injected with 10 ng of pQQH1 cRNA or water. Nucleoside uptake was measured after 3 days and was traced with the respective $^3$H-labeled nucleoside (Moravek Biochemicals)(20 μC/ml), which was purified by high performance liquid chromatography before use. Flux measurements were performed at 20° C. on groups of 10–20 oocytes in transport buffer (0.2 ml) containing 100 mM NaCl or 100 mM choline chloride, 2 mM KCl, 1 mM CaCl$_2$, 1 mM MgCl, 10 mM HEPES, pH 7.5. At the end of the incubation, extracellular label was removed by six rapid ice-cold washes in the appropriate transport buffer. Individual oocytes were dissolved in 5% SDS for quantitation of oocyte-associated $^3$H by liquid scintillation counting (LS 6000 IC, Beckman).

Example 3

Northern Blot Analysis—Poly(A)+ RNA from rat jejunum (10 jig) was separated on a 0.8% formaldehyde-agarose gel and blotted onto a Hybond-N transfer membrane (Amersham Corp. ). PstI—PstI (420 bp) and AccI-BamH1 (617 bp) fragments of pQQH1 that represented coding sequences for CNT1 amino acid residues 75–213 and 385–588, respectively, were labeled with $^{32}$P using a T7 QuickPrime kit (Pharmacia Biotech). Hybridization was for 16 h at 42° C. in 50% formamide. The membrane was washed twice in 0.1× SSC, 0.1% SDS at room temperature and twice at 65° C. A multiple rat tissue blot (Clontech) (2 μg of poly(A)+ RNA/lane) was probed with the 32 P-labeled AccI-BamHI fragment under identical conditions.

Example 4 cDNA Cloning and Sequencing—PCR amplification of hCNT1 partial cDNA was performed on plasmid DNA from a Clontech 5'-Stretch pYEUra3 human kidney cDNA library using primers (Q1,Q2) complementary to two conserved 3'-coding regions of rCNT1 cDNA (FIG. 8). The PCR reaction (100 μl) contained 5 μl template DNA (5 ng/μl), 2.5 units Taq DNA polymerase and 50 pmol each of Q1 and Q2 corresponding to rCNT1 cDNA nucleotide positions 1565–1588 (sense, 5'-CTGTGGCCTTCTTGATGGGTGTGG-3') (SEQ ID NO. 9) and 1777–1801 (antisense, 5'-CCCGATGGAGCTGAAGTTGGCAAA-3') (SEQ ID NO. 10), respectively. Amplification for 30 cycles at 94° C. for 1 min, 50° C. for 1.5 min and 72° C. for 1.5 min (Robocycler™ 40 Temperature Cycler, Stratagene) generated an hCNT1 235-bp fragment that was 86% identical to the corresponding region of rCNT1. This cDNA, labelled with $^{32}$P (QuickPrime kit, Pharmacia Biotech), was used to screen 5×10 colonies from the pYEUra3 cDNA library and 10$^6$ colonies from a Clontech 5'-Stretch Plus pCDNAI human kidney cDNA library. Three positive, incomplete pYEUra3 clones and seven positive, incomplete pCDNAI clones were sequenced in both directions by Taq DyeDeoxy terminator cycle sequencing using an automated Model 373A DNA Sequencer (Applied Biosystems, Inc.). Sequence alignments indicated that all 10 cDNAs were derived from the same RNA transcript. One pCDNAI clone contained 5'-untranslated sequence and a downstream open reading frame that ended 23-bp short of the Q2 priming site. A second pcDNAI clone contained 3'-untranslated sequence, including a polyA tail, and an open reading frame that extended 590-bp upstream of the Q1 priming site. These overlapping cDNAs were spliced at an Acc1 restriction site 256-bp upstream of Q1 and subcloned into pBluescript H KS +/− (Stratagene) to yield a composite 2.79-kb full-length hCNT1 clone (pMHK1).

hCNT1 cDNA was also obtained by RT-PCR amplification of human kidney RNA (Clontech) using primers flanking the pMHK1 open reading frame. First strand cDNA was synthesized using the SuperScript Preamplification System (GibcoBRL) and oligo-dT as primer. The PCR reaction (30 µl) contained 50 ng template 1st strand cDNA, 2.5 units Taq/Deep Vent DNA polymerase (100:1) and 10 pmol each of primers Q3 and Q4 corresponding to pMHK1 nucleotide positions 170 to 192 (sense, 5'-TGGAAGGTCTGGGACATGGAGAA-3') (SEQ ID NO. 11) and 2227 to 2249 (antisense, 5'-TCTAAGTCCTGTGGCTTCCCTGA-3') (SEQ ID NO. 12). Amplification for 1 cycle at 94° C. for 5 min, 59° C. for 1.5 min and 72° C. for 1.5 min, 25 cycles at 94° C. for 1 min, 58° C. for 1.5 min and 72° C. for 1.5 min and 1 cycle at 72° C. for 10 min generated a ~2-kb product that was ligated into the PCR vector pGEM-T (Promega) and subdloned into Bluescript II KS +/−. Three RT-PCR clones (pMHK2–pMHK4) and the RT-PCR product from which they were derived were sequenced in both directions.

Example 5

Expression of hCNT1 in oocytes—Plasid DNA (pMHK1–pMHK4) was linearised with NotI and bed with T7 polymerase in the presence of the a $^{7m}$GpppG cap using the MEGAscript (Ambion) transcription system (see Example 2). Defolliculated oocytes (Huang et al. 1993) were injected with either 10 nl of water containing 10 ng RNA transcript or 10 nl of water alone. Nucleoside uptake was measured after 3 d and was traced with the respective [$^3$H] or [$^{14}$C]nucleoside (Moravek Biochemicals)(5 µC 3H/ml, 1 µC 14C/ml). Initial rates of transport (influx) were determined at 20° C. in NaCl or choline chloride transport buffer using incubation periods of either 1 min (uridine) or 10 min (adenosine, deoxyadenosine, guanosine, AZT). The transport buffer for adenosine influx experiments contained 1 µM deoxycoformycin to inhibit adenosine deaminase activity. Results are presented as means ±SEM for 10–12 individual oocytes. Kinetic constants were determined by non-linear regression analysis (ENZFITTER, Elsevier-Biosoft). Each experiment was performed at least twice on different batches of oocytes.

Example 6

Northern Blot Analysis—Human kidney MRNA (Clontech) (5 µg) was separated on a 0.8% formaldehyde agarose gel, blotted onto a Hybond-N transfer membrane (Amersham) and probed with a $^{32}$P-labelled 585-bp fragment of pMHK1 encoding hCNT1 amino acid residues 396–590. Hybridization was for 16 h at 42° C. in 50% formamide as previously described.

Example 7

Chromosomal fluorescence in situ hybridization (FISH)—FISH analysis of normal human lymphocyte metaphase chromosomes counterstained with propidium iodide and DAPI was performed by methods described previously (Campbell et al. 1995) using a 2 kb cDNA probe corresponding to the full-length open reading frame of hCNT1a. Biotinylated probe was detected with avidin-FITC (Campbell et al. 1995). Chromosomal localization of the hCNT1 gene was also determined by screening a human PI-derived artificial chromosome (PAC) library (Ioannou et al. 1994).

Example 8

CNT1 or CNT1-specific antibody probes (polyclonal/monoclonal) may be obtained by raising antibodies against fusion-protein constructs or by raising antibodies against isolated or synthetic peptides corresponding to regions of the CNT1 predicted amino acid sequence by standard techniques (for example Harlow, E. & Lane, D.,1988; Davies, A. et al.,1990,; Koerner, T. J. et al., 1991). The whole CNT1 peptide or a portion of CNT1 could be utilized to generate antibodies. Small peptides, for example, could be linked to a carrier using methods known to those skilled in the art to immunize animals.

Similar antibody probes can also be developed for CNT1 nucleotide sequences or portions thereof using techniques known to those skilled in the art.

These antibodies could be provided in a kit. The antibodies could be unlabeled; or suitably labelled.

Anti-CNT1 antibodies and probes will have application in studies of nucleoside physiology and pharmacology allowing, for example, analysis of the distribution, amounts and regulation of transport protein in normal cells and tissues and in pathologic (eg. neoplastic) states. Such information, together with the development of transport inhibitors and nucleoside drugs specific for different nucleoside transporter subtypes will permit the custom design of chemotherapy for an individual's specific cancer, or for the design of nucleoside therapies to treat particular diseases.

The entire amino acid sequences described in FIGS. 1 (SEQ ID NO. 8) and 7 (SEQ ID NO. 4, 5, 6) or portions thereof can be used to generate antibodies.

For identification of CNT transporters in intact cells antibodies capable of binding to extracellular regions would be desired. For intact cells, preferred antibody epitomes include but are not limited to the extracellular amino acids regions as indicated in FIG. 2 including but not limited to rat amino acid sequences 225 to 238 inclusive; 285 to 298 inclusive; 448 or 459 inclusive or 554 to 574 inclusive or corresponding human amino acid sequences. These amino acids or fragments thereof could be used to generate antibodies. Someone skilled in the art would know how to attached the amino acids to a carrier so that they would be immunogenic and someone skilled in the art could generate monoclonal or polyclonal antibodies without undue experimentation.

For permeabilized cells or membrane, either extracellular or intracellular amino acid sequences but not transmembrane sequences would be preferred as antibody binding sites.

Preferred amino acid sequences for the production of antibodies include but are not limited to EPGFIAFQWLGDQI (rat CNT1 225 to 238), EPGFIAFEWLGEQI (human CNT1), LMQWVILKIAWLMQ (rat CNT1 285 to 298 and corresponding human CNT1 sequence); WLGDMVDIQGLS (rat CNT1 448 or 459 and correspending human CNT1 sequence), LTSLVPQRRSDFSQIVLRALI (rat CNT1 554 to 574), LTSMVPQRKSDFSQIVLRALF (human CNT sequence) (SEQ ID NO. 13–18, respectively) or portion thereof.

The invention provides a cDNA sequence encoding a Na+-dependent nucleoside transport protein, CNT1 or CNT 1.

Example 9

Design of chemotherapy

For the treatment of disease, knowledge of the characteristics of the target cells and normal cells is important to the design of the treatment. Antibodies or nucleotide probes capable of binding to the sequences described herein can be utilized to help identify the types of NT that are present in specific types of cells or tissues.

For treatment of cancer, knowing the type of transporter (s), their levels of expression and their functional properties in the neoplastic cells is important. In cancer chemotherapy, drugs that are nucleoside analogs or act like nucleoside analogs must be able to enter the cell to be effective. If the neoplastic cells express a high number of CNT1, therapy may include drugs that are good permeants for CNT1.

If the neoplastic cells are deficient in the expression of CNT1, permeants that are more suitable for other transporters may be required. If the permeant can also be transported through CNT1 then some protection of normal tissues from the chemotherapy may be possible by using a CNT1 inhibitor.

Although the invention has been described with reference to the presently preferred embodiment, it should be understood that various modifications can be made without departing from the spirit of the invention. Accordingly, the invention is limited only by the following claims.

All of the following references are incorporated by reference in their entirety:

Amara, S. G., and Kuhar, M. J. (1993) Annu. Rev. Neurosci. 16, 73–93.

Belardinelli, L., J. Linden, and R. M. Berne. The cardiac effects of adenosine. Prog. Cardiovasc. Dis. 32: 73–97, 1989.

Belardinelli, L. et al. (1989) Prog. Cardiovasc. Dis. 32, 73–97

Belt, J. A., N. M. Marina, and D. A. Phelps. Nucleoside transport in normal and neoplastic cells. Adv. Enz. Regul. 33: 235–252, 1993.

Betcher, S. L., J. N. Forrest Jr, R. G. Knickelbein, and J. W. Dobbins. Sodium-adenosine cotransport in brush-border membranes from rabbit ileum. Am. J. Physiol. 259:G504–510, 1990.

Bleasby, A. J., and Wootton, J. C. (1990) Protein Eng. 3, 153–159.

Campbell, C., K. Goodrich, G. Casey and B. Beatty. Cloning and mapping of a human gene (IBX2) sharing a highly conserved protein motif with the drosophila omb gene. Genomics 28: 255–260, 1995.

Cass, C. E. Nucleoside transport. In: Drug transport in antimicrobial and anticancer chemotherapy, edited by N. H. Georgopapadakou. New York: Marcel Dekker, 1995, p. 403–451.

Chan, T. C. K., Boon, G. D., Shaffer, L., and Redmond, R. (1992) Eur.J. Haematol. 49, 71–76.

Chan, T. C. K., Shaffer, L., Redmond, R., and Pennington, K. L. (1993) Biochem. Pharmacol. 46, 273–278.

Che, M., D. F. Ortiz, and I. M. Arias. Primary structure and functional expression of a cDNA encoding the bile canalicular purine-specific Na+-nucleoside cotransporter. J. Biol. Chem. 270: 13596–13599, 1995.

Che, M., T. Nishida, Z. Gatmaitan, and I. M. Arias. A nucleoside transporter is functionally linked to ectonucleotidases in rat liver canalicular membrane. J. Biol. Chem. 267: 9684–9688, 1992.

Clumeck, N. Current use of anti-HIV drugs in AIDS. J. Antimicrobiol. Chemother. 32 Suppl.A: 133–138, 1993.

Craig, J. E., Y. Zhang, and M. R. Gallagher. Cloning of the nupC gene of Escherichia coli encoding a nucleoside transport system, and identification of an adjacent insertion element, IS186. Mol. Microbiol. 11: 1159–1168, 1994.

Domin, B. A., Mahoney, W. B., and Zimmerman, T. P. (1993) Biochem.Pharmacol. 46, 725–729.

Fang, X., F. E. Parkinson, D. A. Mowles, J. D. Young, and C. E. Cass. Functional characterization of a recombinant sodium-dependent nucleoside transporter with selectivity for pyrimidine nucleosides (CNT1 rat) by transient expression in cultured mammalian cells. Biochem. J. 317: 457–465, 1996.

Good, S. S., C. S., Koble, R. Crouch, R. L. Rideout, and P. De Miranda. Isolation and characterization of an ether glucuronide of zidovudine, a major metabolite in monkeys and humans. Drug Metab. Disp. 18: 321–326, 1990.

Griffiths, D. A., S. D. Hall and P. R. Sokol. Efect of 3'-azido3'-deoxythymidine (AZT) on organic ion transport in rat renal brush border membrane vesicles. J. Pharmacol. Exptl. Therap. 260: 128–133, 1992.

Gutierrez, M. M. and K. M. Giacomini. Substrate selectively, potential sensitivity and stoichiometry of Na+-nucleoside transport in brush border membranes vesicles from human kidney. Biochem. Biophys. Acta 1149: 202–208, 1993.

Gutierrez, M. M. and K. M. Giacomini. Expression of a human renal sodium nucleoside cotransporter in Xenopus laevis oocytes. Biochem. Pharmacol. 48: 2251–2253, 1994.

Gutierrez, M. M., and Giacomini, K. M. (1993) Biochem. Biophys. Acta 1149, 202–208.

Handschumacher, R. E. and Cheng, C. Y. (1993) in Cancer Metabolism (Holland, E., Frei, E., Bast, R. C., Kufe, D. W., Morton, D. L., and Weichselbaum, R. R. eds)pp. 712–732, Lea & Febiger, Philadelphia.

Hediger, M. A., Coady, M. J., Ikeda, T. S., and Wright, E. M. (1987) Nature 330, 379–381.

Huang, Q. -Q., C. M. Harvey, A. R. P. Paterson, C. E. Cass, and J. D. Young. Functional expression of Na-dependent nucleoside transport systems of rat intestine in isolated oocytes of Xenopus laevis. Demonstration that rat jejunum expresses the purine-selective system Ni (cif) and a second novel system N3 having board specificity for purine and pyrimidine nucleosides. J. Biol. Chem. 268: 20613–20619, 1993.

Huang, Q. -Q., S. Y. M. Yao, M. W. L. Ritzel, A. R. P. Paterson, C. E. Cass and J. D. Young. Cloning and functional expression of a complementary DNA encoding a mammalian nucleoside transport protein. J. Biol. Chem. 269: 17757–17760, 1994.

Ioannou, P. A., C. T. Amemiya, J. Games, P. M. Kroisel, H. Shizuya, C. Chen, M. A. Batzer and P. J. de Jong. A new bacteriophage PI-derived vector for the propogation of large human DNA fragments. Nature Genetics 6: 84–89, 1994.

Jacobson, K. A., J. W. Daly, and V. Manganiello. In: Purines in Cellular Signalling: Targets for New Drugs. Springer Verlag, N.Y., 1990.

Jarvis, S. M. (1989) Biochem. Biophys. Acta 979, 132–138.

Jarvis, S. M., and Griffith, D. A. (1991) Biochem. J. 278, 605–607.

Kanai, Y. Smith, C. P., and Hediger, M. A. (1993) Trends Neurol. Sci. 16, 365–370.

Kaye, S. B. Gemcitabine: current status of phase I and II trials. J. Clin. Oncol. 12, 1527–1531 (1994).

Kuttesch, J. F. and J. A. Nelson. Renal handling of 2'-deoxyadenosine and adenosine in humans and mice. Cancer Chemoth. Pharmacol. 8: 221–229, 1982.

Kwong, F. Y. P. et al. Enzymic cleavage as a probe of the molecular structures of mammalian equilibrative nucleoside transporters. J. Biol. Chem. 268, 22127–22134 (1993).

Kwong, F. Y. P. et al. Mammalian nitrobenzylthioinosine-sensitive nucleoside transport proteins: immunological evidence that transporters differing in size and inhibitor-sensitivity share sequence homology. J. Biol. Chem. 267, 21954–21960 (1992).

Kwong, F. Y. P., A. Davies, C. -M. Tse, J. D. Young, P. J. F. Henderson, and S. A. Baldwin. Purification of the human erythrocyte nucleoside transporter by immunoaffinity chromatography. Biochem. J. 255: 243–249, 1988.

Kwong, F. Y. P., H. E. Fincham, A. Davies, N. Beaumont, P. J. E. Henderson, J. D. Young, and S. A. Baldwin. Mammalian nitrobenzylthioinosine-sensitive nucleoside transport proteins. J.Biol. Chem. 267: 21954–21960, 1992.

Kwong, F. Y. P., J. S. R. Wu, M. M. Shi, H. E. Fincham, A. Davies, P. J. F. Henderson, S. A. Baldwin, and J. D. Young. Enzymatic cleavage as a probe of the molecular structures of mammalian equilibrative nucleoside transporters. J. Biol. Chem. 268: 22127–22134, 1993.

Le Hir, M. and U. C. Dubach Sodium-gradient-energized concentrative transport of adenosine in renal brush border vesicles. Pflugers Arch. 401: 58–63, 1984.

Lee, C. W., Cheeseman, C. I. and Jarvis, S. M. (1990) Am. J. Physiol. 258, F1203-F1210.

Melvin, G. C., S. R. Ellison, C. M. Monk, and T. R. Bates. Existence of a flip-flop kinetic model for zidovudine (AZT) after oral adminstration. Res. Commun. Chem. Pathol. Pharmacol. 70: 193–204, 1990.

Munch-Petersen, A., and Mygind, B. (1983) in Metabolism of Nucleotides, Nucleosides and Nucleobases in Microorganisms (Munch-Petersen, A., ed) Academic Press, London.

Nelson, J. A., J. F. Kuttesch and B. H. Herbert. renal secretion of purine nucleosides and their analogs in mice. Biochem. Pharmacol. 32: 2323–2327, 1983.

Pajor, A. M. Molecular cloning and expression of SNST1, a renal sodium/nucleoside cotransporter. Drug Develop. Res. 31: 305, 1994.

Pajor, A. M., and E. R. Wright. Cloning and functional expression of a mammalian Na+/nucleoside cotransporter. A member of the SGLT family. J. Biol. Chem. 267: 3557–3560, 1992.

Park, G. B. and A. K. Mitra Mechanism and site dependency of intestinal mucosal transport and metabolism of thymidine analogs. Pharmaceut. Res. 9: 326–331, 1992.

Paterson et al. (1991) in Role of Adenosine and Adenine Nucleotides in Biological Systems (Imai, S., and Nakazawa, M., eds) pp.133–148.

Paterson, A. R. P. et al. (1983) in Regulatory Functions of Adenosine (Berne, R. M., Rall, T. W and Rubio, R. eds) pp. 203–220, Martinus Nijhoff, The Hague.

Paterson, A. R. P., W. P. Gati and D. Vijayalakshmi. Inhibitor-sensitive, Na+-linked transport of nucleoside analogs in leukemia cells from patients. Proc. Am. Assoc. Cancer Res. 34: 14, 1993.

Perigaud, C., G. Gossselin, and J. L. Imbach. Nucleoside analogues as chemotherapeutic agents: a review. Nucleosides and Nucleotides 11: 903–945, 1992.

Plagemann, P. G. W. Na+-dependent, concentrative nucleoside transport in rat marcophages. Specificity for natural nucleosides and nucleoside analogs, including dideoxynucleosides, and comparison of nucleoside transport in rat, mouse and human macrophages. Biochem. Pharmacol. 42: 247–252, 1991.

Plagemann, P. G. W., J. M. Aran, and C. Woffendin. Na+-dependent, active and Na+-independent, facilitated transport of formycin B in mouse spleen lymphocytes. Biochem. Biophys. Acta. 1022: 93–102, 1990.

Roden, M., Paterson, A. R. P. and Tumheim, K. (1991) Gastroenterology 100, 1553–1562.

Stein, WD. (1986) Transport and Diffusion across Cell Membranes, pp. 397–400, Academic Press, London.

Terasaki, T., Kadowaki, A., Higashida, H., Nakayama, K., Tamai, I. and Tsuji, A. (1993) Biol. Pharm. Bull. 16, 493–496.

Trimble, M. E. and R. Coulson. Adenosine transport in perfused rat kidney and renal cortical membrane vesicles. Am. J. Physiol. 15:F794-F803, 1984

Turner, R. J., and Weiner, J. H. (1993) Biochem. Biophys. Acta 1202, 161–168.

Ullman, B. (1989) J. Physiol. 601, 416–421.

Vijayalakshmi, D. and J. A. Belt. Sodium-dependent nucleoside transport in mouse intestinal epithelial cells. J. Biol. Chem. 263: 19419–19423, 1988.

von Heijne, G. (1992) J. Mol. Biol. 225, 487–494.

Wang, C. D., Buck, M. A., and Fraser, C. M. (1991) Mol. Pharmacol. 40, 168–179.

Williams, T. C., A. J. Doherty, D. A. Griffith, and S. M. Jarvis. Characterization of sodium-dependent and sodium-independent nucleoside transport systems in rabbit brush-border and basolateral plasma-membrane vesicles from renal outer cortex. Biochem. J. 264: 223–231, 1989.

Williams, T. C., and Jarvis, S. M. (1991) Biochem. J. 274,27–33.

Wu, J. S. et al. (1983) J. Biol. Chem. 258, 13745–13751.

Wu, X. et al. (1992) J. Biol. Chem. 267, 8813–8818.

Wu, X., M. M. Gutierrez, and K. M. Giacomini. Further characterization of the sodium-dependent nucleoside transporter (N3) in choroid plexus from rabbit. Biochem. Biophys. Acta 1191: 190–196, 1994.

Yao, S. Y. M., A. M. L. Ng, M. W. L. Ritzel, C. E. Cass and J. D. Young. Transport of adenosine by recombinant NI/cif and N2/cit sodium/nucleoside cotransporters from rat jejunum expressed in Xenopus oocytes. Mol. Pharmacol., 1996. (submitted, under revision)

Yao, S. Y. M., C. E. Cass, and J. D. Young. Transport of the antiviral nucleoside analogs 3'-azido-3'-deoxythymidine (AZT) and 2',3'-dideoxycytidine (ddC) by a recombinant nucleoside transporter (rCNT1) expressed in Xenopus oocytes. Mol. Pharmacol.,1996 (in press)

Young, J. D. & Jarvis, S. M. Nucleoside transport in animal cells. Biosci. Rep. 3, 309–322 (1983).

Zimmerman, T. P., Mahoney, W. P., and Prus, K. L. (1987) J. Biol. Chem. 262, 5748–5754.

What is claimed is:

1. An isolated polynucleotide encoding a polypeptide having the amino acid sequence selected from the group consisting of SEQ ID NO:4, SEQ ID NO:5, and SEQ ID NO:6.

2. A host cell containing the polynucleotide of claim 1.

3. A recombinant expression vector containing the polynucleotide of claim 1.

4. The vector of claim 3, which is derived from a virus.

5. The vector of claim 4, wherein the virus is an RNA virus.

6. The vector of claim 5, wherein the RNA virus is a retrovirus.

7. The vector of claim 3, wherein the vector is a plasmid.

8. An isolated polynucleotide selected from the group consisting of:
   (a) a polynucleotide having the nucleotide sequence of SEQ ID NO:7, wherein T can also be U;
   (b) a polynucleotide having a nucleotide sequence complimentary to (a); and
   (c) a fragment of (a) or (b) that is at least 15 nucleotide bases in length and that hybridizes under stringent conditions to DNA which encodes a polypeptide of SEQ ID NO:8.

9. An isolated polynucleotide selected from the group consisting of:
   (a) a polynucleotide having the nucleotide sequence of SEQ ID NO: 1, 2 or 3, wherein T can also be U;
   (b) a polynucleotide having a nucleotide sequence complementary to (a); and
   (c) a fragment of of (a) or (b) that is at least 15 nucleotide bases in length and that hybridizes under stringent conditions to DNA which encodes the polypeptide of SEQ ID NO: 4, 5 or 6.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 2790 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 1..2790

(xi) SEQUENCE DESCRIPTION: SEQ ID NO:1:

```
CTGGCTGTGC TGTTCATCTC CTAGATGAAT GGGATGGTCT ACATTCATCC ATTTGGATTT      60

GGCCAAAGAC ACCAACACCC CTTTCTCCCT CTACATAAGC TGCACTGCAT GGTTGCTGCT     120

GGATGTGTTG TGTTCCTGGC TTCCCTCTGG ATGCTGACAG AAACAAGGCT GGAAGGTCTG     180

GGAC ATG GAG AAC GAC CCC TCG AGA CGA AGA GAG TCC ATC TCT CTC ACA      229
     Met Glu Asn Asp Pro Ser Arg Arg Arg Glu Ser Ile Ser Leu Thr
     1               5                   10                  15

CCT GTG GCC AAG GGT CTG GAG AAC ATG GGG GCT GAT TTC TTG GAA AGC       277
Pro Val Ala Lys Gly Leu Glu Asn Met Gly Ala Asp Phe Leu Glu Ser
                20                  25                  30

CTG GAG GGA GGC CAG CTC CCT AGG AGT GAC TTG AGC CCC GCA GAG ATC       325
Leu Glu Gly Gly Gln Leu Pro Arg Ser Asp Leu Ser Pro Ala Glu Ile
            35                  40                  45

AGG AGC AGC TGG AGC GAG GCG GCG CCG AAG CCC TTC TCC AGA TGG AGG       373
Arg Ser Ser Trp Ser Glu Ala Ala Pro Lys Pro Phe Ser Arg Trp Arg
        50                  55                  60

AAC CTG CAG CCA GCC CTG AGA GCC AGA AGC TTC TGC AGG GAG CAC ATG       421
Asn Leu Gln Pro Ala Leu Arg Ala Arg Ser Phe Cys Arg Glu His Met
    65                  70                  75

CAG CTG TTT CGA TGG ATC GGC ACA GGC CTG CTC TGC ACT GGG CTC TCT       469
Gln Leu Phe Arg Trp Ile Gly Thr Gly Leu Leu Cys Thr Gly Leu Ser
80                  85                  90                  95

GCC TTC CTG CTG GTG GCC TGC CTC CTG GAT TTC CAG AGG GCC CTG GCT       517
Ala Phe Leu Leu Val Ala Cys Leu Leu Asp Phe Gln Arg Ala Leu Ala
                100                 105                 110

CTG TTT GTC CTC ACC TGT GTG GTC CTC ACC TTC CTG GGC CAC CGC CTG       565
Leu Phe Val Leu Thr Cys Val Val Leu Thr Phe Leu Gly His Arg Leu
            115                 120                 125

CTG AAA CGG CTT CTG GGG CCA AAG CTG AGG AGG TTT CTT GTC AAG CCT       613
Leu Lys Arg Leu Leu Gly Pro Lys Leu Arg Arg Phe Leu Val Lys Pro
        130                 135                 140

CAG GGC CAT CCC CGC CTG CTG CTC TGG TTT AAG AGG GGT CTA GCT CTT       661
Gln Gly His Pro Arg Leu Leu Leu Trp Phe Lys Arg Gly Leu Ala Leu
    145                 150                 155

GCT GCT TTC CTG GGC CTG GTC CTG TGG CTG TCT CTG GAC ACC TCC CAG       709
Ala Ala Phe Leu Gly Leu Val Leu Trp Leu Ser Leu Asp Thr Ser Gln
160                 165                 170                 175

CGG CCT GAG CAA CTG GTG TCC TTC GCA GGA ATC TGC GTG TTC GTC GCT       757
Arg Pro Glu Gln Leu Val Ser Phe Ala Gly Ile Cys Val Phe Val Ala
                180                 185                 190

CTC CTC TTT GCC TGC TCA AAG CAT CAT TGC GCA GTG TCC TGG AGG GCC       805
Leu Leu Phe Ala Cys Ser Lys His His Cys Ala Val Ser Trp Arg Ala
            195                 200                 205
```

```
GTG TCT TGG GGA CTT GGA CTG CAG TTT GTA CTT GGA CTC CTC GTC ATC        853
Val Ser Trp Gly Leu Gly Leu Gln Phe Val Leu Gly Leu Leu Val Ile
        210                 215                 220

AGA ACA GAA CCA GGA TTC ATT GCG TTC GAG TGG CTG GGC GAG CAG ATC        901
Arg Thr Glu Pro Gly Phe Ile Ala Phe Glu Trp Leu Gly Glu Gln Ile
225                 230                 235

CGG ATC TTC CTG AGC TAC ACG AAG GCT GGC TCC AGC TTC GTG TTT GGG        949
Arg Ile Phe Leu Ser Tyr Thr Lys Ala Gly Ser Ser Phe Val Phe Gly
240                 245                 250                 255

GAG GCG CTG GTC AAG GAT GTC TTT GCC TTT CAG GTT CTG CCC ATC ATT        997
Glu Ala Leu Val Lys Asp Val Phe Ala Phe Gln Val Leu Pro Ile Ile
                260                 265                 270

GTC TTT TTC AGC TGT GTC ATA TCC GTT CTC TAC CAC GTG GGC CTC ATG       1045
Val Phe Phe Ser Cys Val Ile Ser Val Leu Tyr His Val Gly Leu Met
            275                 280                 285

CAG TGG GTG ATC CTG AAG ATT GCC TGG CTG ATG CAA GTC ACC ATG GGC       1093
Gln Trp Val Ile Leu Lys Ile Ala Trp Leu Met Gln Val Thr Met Gly
        290                 295                 300

ACC ACA GCC ACT GAG ACC CTG AGT GTG GCT GGA AAC ATC TTT GTG AGC       1141
Thr Thr Ala Thr Glu Thr Leu Ser Val Ala Gly Asn Ile Phe Val Ser
    305                 310                 315

CAG ACC GAG GCT CCA TTA CTG ATC CGG CCC TAC TTG GCA GAC ATG ACA       1189
Gln Thr Glu Ala Pro Leu Leu Ile Arg Pro Tyr Leu Ala Asp Met Thr
320                 325                 330                 335

CTC TCT GAA GTC CAC GTT GTC ATG ACC GGA GGT TAC GCC ACC ATT GCT       1237
Leu Ser Glu Val His Val Val Met Thr Gly Gly Tyr Ala Thr Ile Ala
                340                 345                 350

GGC AGC CTG CTG GGT GCC TAC ATC TCC TTT GGG ATC GAT GCC ACC TCG       1285
Gly Ser Leu Leu Gly Ala Tyr Ile Ser Phe Gly Ile Asp Ala Thr Ser
            355                 360                 365

TTG ATT GCA GCC TCT GTG ATG GCT GCC CCT TGT GCC TTG GCC CTC TCC       1333
Leu Ile Ala Ala Ser Val Met Ala Ala Pro Cys Ala Leu Ala Leu Ser
        370                 375                 380

AAA CTG GTC TAC CCG GAG GTG GAG GAG TCC AAG TTT AGG AGG GAG GAA       1381
Lys Leu Val Tyr Pro Glu Val Glu Glu Ser Lys Phe Arg Arg Glu Glu
    385                 390                 395

GGA GTG AAA CTG ACC TAT GGA GAT GCT CAG AAC CTC ATA GAA GCA GCC       1429
Gly Val Lys Leu Thr Tyr Gly Asp Ala Gln Asn Leu Ile Glu Ala Ala
400                 405                 410                 415

AGC ACT GGG GCC GCC ATC TCC GTG AAG GTG GTC GCC AAC ATC GCT GCC       1477
Ser Thr Gly Ala Ala Ile Ser Val Lys Val Val Ala Asn Ile Ala Ala
                420                 425                 430

AAC CTG ATT GCG TTC CTG GCT GTG CTG GAC TTT ATC AAT GCT GCC CTC       1525
Asn Leu Ile Ala Phe Leu Ala Val Leu Asp Phe Ile Asn Ala Ala Leu
            435                 440                 445

TCC TGG CTG GGA GAC ATG GTG GAC ATC CAG GGG CTC AGC TTC CAG CTC       1573
Ser Trp Leu Gly Asp Met Val Asp Ile Gln Gly Leu Ser Phe Gln Leu
        450                 455                 460

ATC TGC TCC TAC ATC CTG CGG CCT GTA GCC TTC TTG ATG GGT GTG GCG       1621
Ile Cys Ser Tyr Ile Leu Arg Pro Val Ala Phe Leu Met Gly Val Ala
    465                 470                 475

TGG GAG GAC TGC CCA GTG GTA GCT GAG CTG CTG GGG ATC AAG CTG TTT       1669
Trp Glu Asp Cys Pro Val Val Ala Glu Leu Leu Gly Ile Lys Leu Phe
480                 485                 490                 495

CTG AAC GAG TTT GTG GCC TAT CAA GAC CTC TCC AAG TAC AAG CAA CGC       1717
Leu Asn Glu Phe Val Ala Tyr Gln Asp Leu Ser Lys Tyr Lys Gln Arg
                500                 505                 510

CGC CTG GCA GGG GCC GAG GAG TGG GTC GGC GAC AGG AAG CAG TGG ATC       1765
Arg Leu Ala Gly Ala Glu Glu Trp Val Gly Asp Arg Lys Gln Trp Ile
```

-continued

```
                515                 520                 525
TCC GTC AGA GCT GAA GTC CTC ACG ACG TTT GCC CTC TGT GGA TTT GCC    1813
Ser Val Arg Ala Glu Val Leu Thr Thr Phe Ala Leu Cys Gly Phe Ala
        530                 535                 540

AAT TTC AGC TCC ATT GGG ATC ATG CTG GGA GGC TTG ACC TCC ATG GTC    1861
Asn Phe Ser Ser Ile Gly Ile Met Leu Gly Gly Leu Thr Ser Met Val
545                 550                 555

CCC CAA CGG AAG AGC GAC TTC TCC CAG ATA GTG CTC CGG GCG CTC TTC    1909
Pro Gln Arg Lys Ser Asp Phe Ser Gln Ile Val Leu Arg Ala Leu Phe
560                 565                 570                 575

ACG GGA GCC TGT GTG TCC CTG GTG AAC GCC TGT ATG GCA GGG ATC CTC    1957
Thr Gly Ala Cys Val Ser Leu Val Asn Ala Cys Met Ala Gly Ile Leu
                580                 585                 590

TAC ATG CCC AGG GGG GCT GAA GTT GAC TGC ATG TCC CTC TTG AAC ACG    2005
Tyr Met Pro Arg Gly Ala Glu Val Asp Cys Met Ser Leu Leu Asn Thr
            595                 600                 605

ACC CTC AGC AGC AGC AGC TTT GAG ATT TAC CAG TGC TGC CGT GAG GCC    2053
Thr Leu Ser Ser Ser Ser Phe Glu Ile Tyr Gln Cys Cys Arg Glu Ala
        610                 615                 620

TTC CAG AGC GTC AAT CCA GAG TTC AGC CCA GAG GCC CTG GAC AAC TGC    2101
Phe Gln Ser Val Asn Pro Glu Phe Ser Pro Glu Ala Leu Asp Asn Cys
    625                 630                 635

TGT CGG TTT TAC AAC CAC ACG ATC TGT GCA CAG TGA GGACAGAACA         2147
Cys Arg Phe Tyr Asn His Thr Ile Cys Ala Gln
640                 645                 650

TGCTTGTGCT TCTGCGCTTC TGAGGGCTGT TCTCCCCCGG GAACCATCTG TCCCCACCTT  2207

CCCTTTCCCA GAGCCCTCTT CAGGGAAGCC ACAGGACTTA GACCCAGCTC AATCCCACAA  2267

TTGGGAAGGG GTCATGGAGT GAGTGTGCAG AGAGTGAGTG AGGACATAAG GAAGGACATG  2327

TCCCACTCCA TCCCCCTTCC TGCTCCCCCA TTTCCTAACT CCCCCAGTGT GAATTCTCAG  2387

GGTCACTTCT GCCTCCTCCC GTTTCCCCTC ACATCCAAA  CAGCACCCTG GTCCTCTCTA  2447

TCCCCCCTCT CCTGGGGTCC CTCACATGCC CCTTCCCTTC TGTTGTGGGC TGCACACCAA  2507

AGCCTCCTCC CCTCCCCACT TCCTAGGCAC TAGGATCTCT CTGTGGCTTC CCCTGCTGGG  2567

TGGTGTCACC TCTTTCTCTG CTTTCAGAGA AACCCTTCCC GCCTTTCCTC AGAGTGCTTC  2627

CCAAACTGAG GTCCCATGGC ACACTGTCCT GGGAGGCGTT CAGAGGGTTC CATGATGGAC  2687

TAGGTTTGGA ACCACTGGGT TAAATAAACT TAGAGAGGGC TGTTTAAAAA AAAAAAAAA   2747

AAAAAAAAAA AAAAAAAAA  AAAAAAAAA  AAAAAAAAA  AAA                   2790
```

(2) INFORMATION FOR SEQ ID NO:2:

(i) SEQUENCE CHARACTERISTICS:
        (A) LENGTH: 2078 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..2078

(xi) SEQUENCE DESCRIPTION: SEQ ID NO:2:

```
TGGAAGGTCT GGGAC ATG GAG AAC GAC CCC TCG AGA CGG AGA GAG TCC       48
                Met Glu Asn Asp Pro Ser Arg Arg Arg Glu Ser
                1               5                   10

ATC TCT CTC ACA CCT GTG GCC AAG GGT CTG GAG AAC ATG GGG GCT GAT    96
Ile Ser Leu Thr Pro Val Ala Lys Gly Leu Glu Asn Met Gly Ala Asp
        15                  20                  25
```

```
TTC TTG GAA AGC CTG GAG GAA GGC CAG CTC CCT AGG AGT GAC TTG AGC      144
Phe Leu Glu Ser Leu Glu Glu Gly Gln Leu Pro Arg Ser Asp Leu Ser
         30                      35                      40

CCC GCA GAG ATC AGG AGC AGC TGG AGC GAG GCG GCG CCG AAG CCC TTC      192
Pro Ala Glu Ile Arg Ser Ser Trp Ser Glu Ala Ala Pro Lys Pro Phe
     45                      50                      55

TCC AGA TGG AGG AAC CTG CAG CCA GCC CTG AGA GCC AGA AGC TTC TGC      240
Ser Arg Trp Arg Asn Leu Gln Pro Ala Leu Arg Ala Arg Ser Phe Cys
60                      65                      70                  75

AGG GAG CAC ATG CAG CTG TTT CGA TGG ATC GGC ACA GGC CTG CTC TGC      288
Arg Glu His Met Gln Leu Phe Arg Trp Ile Gly Thr Gly Leu Leu Cys
             80                      85                      90

ACT GGG CTC TCT GCC TTC CTG CTG GTG GCC TGC CTC CTG GAT TTC CAG      336
Thr Gly Leu Ser Ala Phe Leu Leu Val Ala Cys Leu Leu Asp Phe Gln
         95                      100                     105

AGG GCC CTG GCT CTG TTT GTC CTC ACC TGT GTG GTC CTC ACC TTC CTG      384
Arg Ala Leu Ala Leu Phe Val Leu Thr Cys Val Val Leu Thr Phe Leu
     110                     115                     120

GGC CAC CGC CTG CTG AAA CGG CTT CTG GGG CCA AAG CTG AGG AGG TTT      432
Gly His Arg Leu Leu Lys Arg Leu Leu Gly Pro Lys Leu Arg Arg Phe
125                     130                     135

CTC AAG CCT CAG GGC CAT CCC CGC CTG CTG CTC TGG TTT AAG AGG GGT      480
Leu Lys Pro Gln Gly His Pro Arg Leu Leu Leu Trp Phe Lys Arg Gly
140                     145                     150                 155

CTA GCT CTT GCT GCT TTC CTG GGC CTG GTC CTG TGG CTG TCT CTG GAC      528
Leu Ala Leu Ala Ala Phe Leu Gly Leu Val Leu Trp Leu Ser Leu Asp
             160                     165                     170

ACC TCC CAG CGG CCT GAG CAG CTG GTG TCC TTC GCA GGA ATC TGC GTG      576
Thr Ser Gln Arg Pro Glu Gln Leu Val Ser Phe Ala Gly Ile Cys Val
         175                     180                     185

TTC ATC GCT CTC CTC TTT GCC TGC TCA AAG CAT CAT TGC GCA GTG TCC      624
Phe Ile Ala Leu Leu Phe Ala Cys Ser Lys His His Cys Ala Val Ser
     190                     195                     200

TGG AGG GCC GTG TCT TGG GGA CTT GGA CTG CAG TTT GTA CTT GGA CTC      672
Trp Arg Ala Val Ser Trp Gly Leu Gly Leu Gln Phe Val Leu Gly Leu
205                     210                     215

CTC GTC ATC AGA ACA GAA CCA GGA TTC ATT GCG TTC GAG TGG CTG GGC      720
Leu Val Ile Arg Thr Glu Pro Gly Phe Ile Ala Phe Glu Trp Leu Gly
220                     225                     230                 235

GAG CAG ATC CGG ATC TTC CTG AGC TAC ACG AAG GCT GGC TCC AGC TTC      768
Glu Gln Ile Arg Ile Phe Leu Ser Tyr Thr Lys Ala Gly Ser Ser Phe
             240                     245                     250

GTG TTT GGG GAG GCG CTG GTC AAG GAT GTC TTT GCC TTT CAG GTT CTG      816
Val Phe Gly Glu Ala Leu Val Lys Asp Val Phe Ala Phe Gln Val Leu
         255                     260                     265

CCC ATC ATT GTC TTT TTC AGC TGT GTC ATA TCC GTT CTC TAC CAC GTG      864
Pro Ile Ile Val Phe Phe Ser Cys Val Ile Ser Val Leu Tyr His Val
     270                     275                     280

GGC CTC ATG CAG TGG GTG ATC CTG AAG ATT GCC TGG CTG ATG CAA GTC      912
Gly Leu Met Gln Trp Val Ile Leu Lys Ile Ala Trp Leu Met Gln Val
285                     290                     295

ACC ATG GGC ACC ACA GCC ACT GAG ACC CTG AGT GTG GCT GGA AAC ATC      960
Thr Met Gly Thr Thr Ala Thr Glu Thr Leu Ser Val Ala Gly Asn Ile
300                     305                     310                 315

TTT GTG AGC CAG ACC GAG GCT CCA TTA CTG ATC CGG CCC TAC TTG GCA     1008
Phe Val Ser Gln Thr Glu Ala Pro Leu Leu Ile Arg Pro Tyr Leu Ala
             320                     325                     330

GAC ATG ACA CTC TCT GAA GTC CAC GTT GTC ATG ACC GGA GGT TAC GCC     1056
Asp Met Thr Leu Ser Glu Val His Val Val Met Thr Gly Gly Tyr Ala
         335                     340                     345
```

-continued

```
ACC ATT GCT GGC AGC CTG CTG GGT GCC TAC ATC TCC TTT GGG ATC GAT      1104
Thr Ile Ala Gly Ser Leu Leu Gly Ala Tyr Ile Ser Phe Gly Ile Asp
        350                 355                 360

GCC ACC TCG TTG ATT GCA GCC TCT GTG ATG GCT GCC CCT TGT GCC TTG      1152
Ala Thr Ser Leu Ile Ala Ala Ser Val Met Ala Ala Pro Cys Ala Leu
        365                 370                 375

GCC CTC TCC AAG CTG GTC TAC CCG GAG GTG GAG GAG TCC AAG TTT AGG      1200
Ala Leu Ser Lys Leu Val Tyr Pro Glu Val Glu Glu Ser Lys Phe Arg
380                 385                 390                 395

AGG GAG GAA GGA GTG AAA CTG ACC TAT GGA GAT GCT CAG AGC CTC ATA      1248
Arg Glu Glu Gly Val Lys Leu Thr Tyr Gly Asp Ala Gln Ser Leu Ile
                400                 405                 410

GAA GCA GCC AGC ACT GGG GCC GCC ATC TCC GTG AAG GTG GTC GCC AAC      1296
Glu Ala Ala Ser Thr Gly Ala Ala Ile Ser Val Lys Val Val Ala Asn
            415                 420                 425

ATC GCT GCC AAC CTG ATT GCG TTC CTG GCT GTG CTG GAC TTT ATC AAT      1344
Ile Ala Ala Asn Leu Ile Ala Phe Leu Ala Val Leu Asp Phe Ile Asn
            430                 435                 440

GCT GCC CTC TCC TGG CTG GGA GAC ATG GTG GAC ATC CAG GGG CTC AGC      1392
Ala Ala Leu Ser Trp Leu Gly Asp Met Val Asp Ile Gln Gly Leu Ser
        445                 450                 455

TTC CAG CTC ATC TGC TCC TAC ATC CTG CGG CCT GTA GCC TTC TTG ATG      1440
Phe Gln Leu Ile Cys Ser Tyr Ile Leu Arg Pro Val Ala Phe Leu Met
460                 465                 470                 475

GGT GTG GCG TGG GAG GAC TGC CCA GTG GTA GCT GAG CTG CTG GGG ATC      1488
Gly Val Ala Trp Glu Asp Cys Pro Val Val Ala Glu Leu Leu Gly Ile
                480                 485                 490

AAG CTG TTT CTG AAC GAG TTT GTG GCC TAT CAA GAC CTC TCC AAG TAC      1536
Lys Leu Phe Leu Asn Glu Phe Val Ala Tyr Gln Asp Leu Ser Lys Tyr
            495                 500                 505

AAG CAA CGC CGC CTG GCA GGG GCC GAG GAG TGG GTC GGC AAC AGG AAG      1584
Lys Gln Arg Arg Leu Ala Gly Ala Glu Glu Trp Val Gly Asn Arg Lys
            510                 515                 520

CAG TGG ATC TCC GTC AGA GCT GAA GTC CTC ACG ACG TTT GCC CTC TGT      1632
Gln Trp Ile Ser Val Arg Ala Glu Val Leu Thr Thr Phe Ala Leu Cys
        525                 530                 535

GGA TTT GCC AAT TTC AGC TCC ATT GGG ATC ATG CTG GGA GGC TTG ACC      1680
Gly Phe Ala Asn Phe Ser Ser Ile Gly Ile Met Leu Gly Gly Leu Thr
540                 545                 550                 555

TCC ATG GTC CCC CAA CGG AAG AGC GAC TTC TCC CAG ATA GTG CTC CGG      1728
Ser Met Val Pro Gln Arg Lys Ser Asp Phe Ser Gln Ile Val Leu Arg
                560                 565                 570

GCG CTC TTC ACG GGA GCC TGT GTG TCC CTG GTG AAC GCC TGT ATG GCA      1776
Ala Leu Phe Thr Gly Ala Cys Val Ser Leu Val Asn Ala Cys Met Ala
            575                 580                 585

GGG ATC CTC TAC ATG CCC AGG GGG GCT GAA GTT GAC TGC ATG TCC CTC      1824
Gly Ile Leu Tyr Met Pro Arg Gly Ala Glu Val Asp Cys Met Ser Leu
            590                 595                 600

TTG AAC ACG ACC CTC AGC AGC AGT AGC TTT GAG ATT TAC CAG TGC TGC      1872
Leu Asn Thr Thr Leu Ser Ser Ser Ser Phe Glu Ile Tyr Gln Cys Cys
605                 610                 615

CGT GAG GCC TTC CAG AGC GTC AAT CCA GAG TTC AGC CCA GAG GCC CTG      1920
Arg Glu Ala Phe Gln Ser Val Asn Pro Glu Phe Ser Pro Glu Ala Leu
620                 625                 630                 635

GAC AAC TGC TGT CGG TTT TAC AAC CAC ACG ATC TGC GCA CAG TGA          1965
Asp Asn Cys Cys Arg Phe Tyr Asn His Thr Ile Cys Ala Gln
                640                 645

GGACAGAACA TGCTTGTGCT TCTGCGCTTC TGAGGGCTGT TCTCCCCCGG GAACCATCTG    2025
```

```
TCCCCACCTT CCCTTTCCCA GAGCCCTCTT CAGGGAAGCC ACAGGACTTA GAT          2078

(2) INFORMATION FOR SEQ ID NO:3:

(i) SEQUENCE CHARACTERISTICS:
        (A) LENGTH: 2078 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..2078

(xi) SEQUENCE DESCRIPTION: SEQ ID NO:3:

TGGAAGGTCT  GGGAC ATG GAG AAC GAC CCC TCG AGA CGG AGA GAG TCC           48
                  Met Glu Asn Asp Pro Ser Arg Arg Arg Glu Ser
                   1               5                  10

ATC TCT CTC ACA CCT GTG GCC AAG GGT CTG GAG AAC ATG GGG GCT GAT         96
Ile Ser Leu Thr Pro Val Ala Lys Gly Leu Glu Asn Met Gly Ala Asp
                15                  20                  25

TTC TTG GAA AGC CTG GAG GAA GGC CAG CTC CCT AGG AGT GAC TTG AGC        144
Phe Leu Glu Ser Leu Glu Glu Gly Gln Leu Pro Arg Ser Asp Leu Ser
         30                  35                  40

CCC GCA GAG ATC AGG AGC AGC TGG AGC GAG GCG GCG CCG AAG CCC TTC        192
Pro Ala Glu Ile Arg Ser Ser Trp Ser Glu Ala Ala Pro Lys Pro Phe
     45                  50                  55

TCC AGA TGG AGG AAC CTG CAG CCA GCC CTG AGA GCC AGA AGC TTC TGC        240
Ser Arg Trp Arg Asn Leu Gln Pro Ala Leu Arg Ala Arg Ser Phe Cys
 60                  65                  70                  75

AGG GAG CAC ATG CAG CTG TTT CGA TGG ATC GGC ACA GGC CTG CTC TGC        288
Arg Glu His Met Gln Leu Phe Arg Trp Ile Gly Thr Gly Leu Leu Cys
                 80                  85                  90

ACT GGG CTC TCT GCC TTC CTG CTG GTG GCC TGC CTC CTG GAT TTC CAG        336
Thr Gly Leu Ser Ala Phe Leu Leu Val Ala Cys Leu Leu Asp Phe Gln
             95                 100                 105

AGG GCC CTG GCT CTG TTT GTC CTC ACC TGT GTG GTC CTC ACC TTC CTG        384
Arg Ala Leu Ala Leu Phe Val Leu Thr Cys Val Val Leu Thr Phe Leu
        110                 115                 120

GGC CAC CGC CTG CTG AAA CGG CTT CTG GGG CCA AAG CTG AGG AGG TTT        432
Gly His Arg Leu Leu Lys Arg Leu Leu Gly Pro Lys Leu Arg Arg Phe
        125                 130                 135

CTC AAG CCT CAG GGC CAT CCC CGC CTG CTG CTC TGG TTT AAG AGG GGT        480
Leu Lys Pro Gln Gly His Pro Arg Leu Leu Leu Trp Phe Lys Arg Gly
140                 145                 150                 155

CTA GCT CTT GCT GCT TTC CTG GGC CTG GTC CTG TGG CTG TCT CTG GAC        528
Leu Ala Leu Ala Ala Phe Leu Gly Leu Val Leu Trp Leu Ser Leu Asp
                160                 165                 170

ACC TCC CAG CGG CCT GAG CAG CTG GTG TCC TTC GCA GGA ATC TGC GTG        576
Thr Ser Gln Arg Pro Glu Gln Leu Val Ser Phe Ala Gly Ile Cys Val
            175                 180                 185

TTC ATC GCT CTC CTC TTT GCC TGC TCA AAG CAT CAT TGC GCA GTG TCC        624
Phe Ile Ala Leu Leu Phe Ala Cys Ser Lys His His Cys Ala Val Ser
        190                 195                 200

TGG AGG GCC GTG TCT TGG GGA CTT GGA CTG CAG TTT GTA CTT GGA CTC        672
Trp Arg Ala Val Ser Trp Gly Leu Gly Leu Gln Phe Val Leu Gly Leu
        205                 210                 215

CTC GTC ATC AGA ACA GAA CCA GGA TTC ATT GCG TTC GAG TGG CTG GGC        720
Leu Val Ile Arg Thr Glu Pro Gly Phe Ile Ala Phe Glu Trp Leu Gly
220                 225                 230                 235

GAG CAG ATC CGG ATC TTC CTG AGC TAC ACG AAG GCT GGC TCC AGC TTC        768
Glu Gln Ile Arg Ile Phe Leu Ser Tyr Thr Lys Ala Gly Ser Ser Phe
```

-continued

```
            240                 245                 250
GTG TTT GGG GAG GCG CTG GTC AAG GAT GTC TTT GCC TTT CAG GTT CTG     816
Val Phe Gly Glu Ala Leu Val Lys Asp Val Phe Ala Phe Gln Val Leu
                255                 260                 265

CCC ATC ATT GTC TTT TTC AGC TGT GTC ATA TCC GTT CTC TAC CAC GTG     864
Pro Ile Ile Val Phe Phe Ser Cys Val Ile Ser Val Leu Tyr His Val
                270                 275                 280

GGC CTC ATG CAG TGG GTG ATC CTG AAG ATT GCC TGG CTG ATG CAA GTC     912
Gly Leu Met Gln Trp Val Ile Leu Lys Ile Ala Trp Leu Met Gln Val
            285                 290                 295

ACC ATG GGC ACC ACA GCC ACT GAG ACC CTG AGT GTG GCT GGA AAC ATC     960
Thr Met Gly Thr Thr Ala Thr Glu Thr Leu Ser Val Ala Gly Asn Ile
300                 305                 310                 315

TTT GTG AGC CAG ACC GAG GCT CCA TTA CTG ATC CGG CCC TAC TTG GCA    1008
Phe Val Ser Gln Thr Glu Ala Pro Leu Leu Ile Arg Pro Tyr Leu Ala
                320                 325                 330

GAC ATG ACA CTC TCT GAA GTC CAC GTT GTC ATG ACC GGA GGT TAC GCC    1056
Asp Met Thr Leu Ser Glu Val His Val Val Met Thr Gly Gly Tyr Ala
                335                 340                 345

ACC ATT GCT GGC AGC CTG CTG GGT GCC TAC ATC TCC TTT GGG ATC GAT    1104
Thr Ile Ala Gly Ser Leu Leu Gly Ala Tyr Ile Ser Phe Gly Ile Asp
            350                 355                 360

GCC ACC TCG TTG ATT GCA GCC TCT GTG ATG GCT GCC CCT TGT GCC TTG    1152
Ala Thr Ser Leu Ile Ala Ala Ser Val Met Ala Ala Pro Cys Ala Leu
365                 370                 375

GCC CTC TCC AAG CTG GTC TAC CCG GAG GTG GAG GAG TCC AAG TTT AGG    1200
Ala Leu Ser Lys Leu Val Tyr Pro Glu Val Glu Glu Ser Lys Phe Arg
380                 385                 390                 395

AGG GAG GAA GGA GTG AAA CTG ACC TAT GGA GAT GCT CAG AAC CTC ATA    1248
Arg Glu Glu Gly Val Lys Leu Thr Tyr Gly Asp Ala Gln Asn Leu Ile
                400                 405                 410

GAA GCA GCC AGC ACT GGG GCC GCC ATC TCC GTG AAG GTG GTC GCC AAC    1296
Glu Ala Ala Ser Thr Gly Ala Ala Ile Ser Val Lys Val Val Ala Asn
                415                 420                 425

ATC GCT GCC AAC CTG ATT GCG TTC CTG GCT GTG CTG GAC TTT ATC AAT    1344
Ile Ala Ala Asn Leu Ile Ala Phe Leu Ala Val Leu Asp Phe Ile Asn
            430                 435                 440

GCT GCC CTC TCC TGG CTG GGA GAC ATG GTG GAC ATC CAG GGG CTC AGC    1392
Ala Ala Leu Ser Trp Leu Gly Asp Met Val Asp Ile Gln Gly Leu Ser
            445                 450                 455

TTC CAG CTC ATC TGC TCC TAC ATC CTG CGG CCT GTA GCC TTC TTG ATG    1440
Phe Gln Leu Ile Cys Ser Tyr Ile Leu Arg Pro Val Ala Phe Leu Met
460                 465                 470                 475

GGT GTG GCG TGG GAG GAC TGC CCA GTG GTA GCT GAG CTG CTG GGG ATC    1488
Gly Val Ala Trp Glu Asp Cys Pro Val Val Ala Glu Leu Leu Gly Ile
                480                 485                 490

AAG CTG TTT CTG AAC GAG TTT GTG GCC TAT CAA GAC CTC TCC AAG TAC    1536
Lys Leu Phe Leu Asn Glu Phe Val Ala Tyr Gln Asp Leu Ser Lys Tyr
                495                 500                 505

AAG CAA CGC CGC CTG GCA GGG GCC GAG GAG TGG GTC GGC AAC AGG AAG    1584
Lys Gln Arg Arg Leu Ala Gly Ala Glu Glu Trp Val Gly Asn Arg Lys
                510                 515                 520

CAG TGG ATC TCC GTC AGA GCT GAA GTC CTC ACG ACG TTT GCC CTC TGT    1632
Gln Trp Ile Ser Val Arg Ala Glu Val Leu Thr Thr Phe Ala Leu Cys
            525                 530                 535

GGA TTT GCC AAT TTC AGC TCC ATT GGG ATC ATG CTG GGA GGC TTG ACC    1680
Gly Phe Ala Asn Phe Ser Ser Ile Gly Ile Met Leu Gly Gly Leu Thr
540                 545                 550                 555

TCC ATG GTC CCC CAA CGG AAG AGC GAC TTC TCC CAG ATA GTG CTC CGG    1728
```

```
Ser Met Val Pro Gln Arg Lys Ser Asp Phe Ser Gln Ile Val Leu Arg
                560                 565                 570

GCG CTC TTC ACG GGA GCC TGT GTG TCC CTG GTG AAC GCC TGT ATG GCA       1776
Ala Leu Phe Thr Gly Ala Cys Val Ser Leu Val Asn Ala Cys Met Ala
            575                 580                 585

GGG ATC CTC TAC ATG CCC AGG GGG GCT GAA GTT GAC TGC ATG TCC CTC       1824
Gly Ile Leu Tyr Met Pro Arg Gly Ala Glu Val Asp Cys Met Ser Leu
                590                 595                 600

TTG AAC ACG ACC CTC AGC AGC AGT AGC TTT GAG ATT TAC CAG TGC TGC       1872
Leu Asn Thr Thr Leu Ser Ser Ser Ser Phe Glu Ile Tyr Gln Cys Cys
605                 610                 615

CGT GAG GCC TTC CAG AGC GTC AAT CCA GAG TTC AGC CCA GAG GCC CTG       1920
Arg Glu Ala Phe Gln Ser Val Asn Pro Glu Phe Ser Pro Glu Ala Leu
620                 625                 630                 635

GAC AAC TGC TGT CGG TTT TAC AAC CAC ACG ATC TGC GCA CAG TGA GGA       1968
Asp Asn Cys Cys Arg Phe Tyr Asn His Thr Ile Cys Ala Gln
                640                 645

CAGAACATGC TTGTGCTTCT GCGCTTCTGA GGGCTGTTCT CCCCCGGGAA CCATCTGTCC     2028

CCACCTTCCC TTTCCCAGAG CCCTCTTCAG GGAAGCCACA GGACTTAGAT               2078

(2) INFORMATION FOR SEQ ID NO:4:

(i) SEQUENCE CHARACTERISTICS:
        (A) LENGTH: 650 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Asn Asp Pro Ser Arg Arg Glu Ser Ile Ser Leu Thr Pro
1               5                   10                  15

Val Ala Lys Gly Leu Glu Asn Met Gly Ala Asp Phe Leu Glu Ser Leu
                20                  25                  30

Glu Gly Gly Gln Leu Pro Arg Ser Asp Leu Ser Pro Ala Glu Ile Arg
            35                  40                  45

Ser Ser Trp Ser Glu Ala Ala Pro Lys Pro Phe Ser Arg Trp Arg Asn
50                  55                  60

Leu Gln Pro Ala Leu Arg Ala Arg Ser Phe Cys Arg Glu His Met Gln
65                  70                  75                  80

Leu Phe Arg Trp Ile Gly Thr Gly Leu Leu Cys Thr Gly Leu Ser Ala
                85                  90                  95

Phe Leu Leu Val Ala Cys Leu Leu Asp Phe Gln Arg Ala Leu Ala Leu
            100                 105                 110

Phe Val Leu Thr Cys Val Val Leu Thr Phe Leu Gly His Arg Leu Leu
        115                 120                 125

Lys Arg Leu Leu Gly Pro Lys Leu Arg Arg Phe Leu Val Lys Pro Gln
130                 135                 140

Gly His Pro Arg Leu Leu Leu Trp Phe Lys Arg Gly Leu Ala Leu Ala
145                 150                 155                 160

Ala Phe Leu Gly Leu Val Leu Trp Leu Ser Leu Asp Thr Ser Gln Arg
                165                 170                 175

Pro Glu Gln Leu Val Ser Phe Ala Gly Ile Cys Val Phe Val Ala Leu
            180                 185                 190

Leu Phe Ala Cys Ser Lys His His Cys Ala Val Ser Trp Arg Ala Val
        195                 200                 205

Ser Trp Gly Leu Gly Leu Gln Phe Val Leu Gly Leu Leu Val Ile Arg
```

```
            210                 215                 220
Thr Glu Pro Gly Phe Ile Ala Phe Glu Trp Leu Gly Glu Gln Ile Arg
225                 230                 235                 240
Ile Phe Leu Ser Tyr Thr Lys Ala Gly Ser Ser Phe Val Phe Gly Glu
                245                 250                 255
Ala Leu Val Lys Asp Val Phe Ala Phe Gln Val Leu Pro Ile Ile Val
                260                 265                 270
Phe Phe Ser Cys Val Ile Ser Val Leu Tyr His Val Gly Leu Met Gln
                275                 280                 285
Trp Val Ile Leu Lys Ile Ala Trp Leu Met Gln Val Thr Met Gly Thr
                290                 295                 300
Thr Ala Thr Glu Thr Leu Ser Val Ala Gly Asn Ile Phe Val Ser Gln
305                 310                 315                 320
Thr Glu Ala Pro Leu Leu Ile Arg Pro Tyr Leu Ala Asp Met Thr Leu
                325                 330                 335
Ser Glu Val His Val Val Met Thr Gly Gly Tyr Ala Thr Ile Ala Gly
                340                 345                 350
Ser Leu Leu Gly Ala Tyr Ile Ser Phe Gly Ile Asp Ala Thr Ser Leu
                355                 360                 365
Ile Ala Ala Ser Val Met Ala Ala Pro Cys Ala Leu Ala Leu Ser Lys
                370                 375                 380
Leu Val Tyr Pro Glu Val Glu Ser Lys Phe Arg Arg Glu Glu Gly
385                 390                 395                 400
Val Lys Leu Thr Tyr Gly Asp Ala Gln Asn Leu Ile Glu Ala Ala Ser
                405                 410                 415
Thr Gly Ala Ala Ile Ser Val Lys Val Val Ala Asn Ile Ala Ala Asn
                420                 425                 430
Leu Ile Ala Phe Leu Ala Val Leu Asp Phe Ile Asn Ala Ala Leu Ser
                435                 440                 445
Trp Leu Gly Asp Met Val Asp Ile Gln Gly Leu Ser Phe Gln Leu Ile
                450                 455                 460
Cys Ser Tyr Ile Leu Arg Pro Val Ala Phe Leu Met Gly Val Ala Trp
465                 470                 475                 480
Glu Asp Cys Pro Val Val Ala Glu Leu Leu Gly Ile Lys Leu Phe Leu
                485                 490                 495
Asn Glu Phe Val Ala Tyr Gln Asp Leu Ser Lys Tyr Lys Gln Arg Arg
                500                 505                 510
Leu Ala Gly Ala Glu Glu Trp Val Gly Asp Arg Lys Gln Trp Ile Ser
                515                 520                 525
Val Arg Ala Glu Val Leu Thr Thr Phe Ala Leu Cys Gly Phe Ala Asn
                530                 535                 540
Phe Ser Ser Ile Gly Ile Met Leu Gly Gly Leu Thr Ser Met Val Pro
545                 550                 555                 560
Gln Arg Lys Ser Asp Phe Ser Gln Ile Val Leu Arg Ala Leu Phe Thr
                565                 570                 575
Gly Ala Cys Val Ser Leu Val Asn Ala Cys Met Ala Gly Ile Leu Tyr
                580                 585                 590
Met Pro Arg Gly Ala Glu Val Asp Cys Met Ser Leu Leu Asn Thr Thr
                595                 600                 605
Leu Ser Ser Ser Phe Glu Ile Tyr Gln Cys Cys Arg Glu Ala Phe
                610                 615                 620
Gln Ser Val Asn Pro Glu Phe Ser Pro Glu Ala Leu Asp Asn Cys Cys
625                 630                 635                 640
```

Arg Phe Tyr Asn His Thr Ile Cys Ala Gln
            645                 650

(2) INFORMATION FOR SEQ ID NO:5:

(i) SEQUENCE CHARACTERISTICS:
       (A) LENGTH: 649 amino acids
       (B) TYPE: amino acid
       (D) TOPOLOGY: linear (ii) MOLECULE TYPE: protein (xi) SEQUENCE DESCRIPTION: SEQ ID NO:5:

Met Glu Asn Asp Pro Ser Arg Arg Glu Ser Ile Ser Leu Thr Pro
1               5                   10                  15

Val Ala Lys Gly Leu Glu Asn Met Gly Ala Asp Phe Leu Glu Ser Leu
            20                  25                  30

Glu Glu Gly Gln Leu Pro Arg Ser Asp Leu Ser Pro Ala Glu Ile Arg
            35                  40                  45

Ser Ser Trp Ser Glu Ala Ala Pro Lys Pro Phe Ser Arg Trp Arg Asn
50                  55                  60

Leu Gln Pro Ala Leu Arg Ala Arg Ser Phe Cys Arg Glu His Met Gln
65                  70                  75                  80

Leu Phe Arg Trp Ile Gly Thr Gly Leu Leu Cys Thr Gly Leu Ser Ala
                85                  90                  95

Phe Leu Leu Val Ala Cys Leu Leu Asp Phe Gln Arg Ala Leu Ala Leu
                100                 105                 110

Phe Val Leu Thr Cys Val Val Leu Thr Phe Leu Gly His Arg Leu Leu
                115                 120                 125

Lys Arg Leu Leu Gly Pro Lys Leu Arg Arg Phe Leu Lys Pro Gln Gly
130                 135                 140

His Pro Arg Leu Leu Leu Trp Phe Lys Arg Gly Leu Ala Leu Ala Ala
145                 150                 155                 160

Phe Leu Gly Leu Val Leu Trp Leu Ser Leu Asp Thr Ser Gln Arg Pro
                165                 170                 175

Glu Gln Leu Val Ser Phe Ala Gly Ile Cys Val Phe Ile Ala Leu Leu
                180                 185                 190

Phe Ala Cys Ser Lys His His Cys Ala Val Ser Trp Arg Ala Val Ser
                195                 200                 205

Trp Gly Leu Gly Leu Gln Phe Val Leu Gly Leu Leu Val Ile Arg Thr
210                 215                 220

Glu Pro Gly Phe Ile Ala Phe Glu Trp Leu Gly Glu Gln Ile Arg Ile
225                 230                 235                 240

Phe Leu Ser Tyr Thr Lys Ala Gly Ser Ser Phe Val Phe Gly Glu Ala
                245                 250                 255

Leu Val Lys Asp Val Phe Ala Phe Gln Val Leu Pro Ile Ile Val Phe
                260                 265                 270

Phe Ser Cys Val Ile Ser Val Leu Tyr His Val Gly Leu Met Gln Trp
                275                 280                 285

Val Ile Leu Lys Ile Ala Trp Leu Met Gln Val Thr Met Gly Thr Thr
                290                 295                 300

Ala Thr Glu Thr Leu Ser Val Ala Gly Asn Ile Phe Val Ser Gln Thr
305                 310                 315                 320

Glu Ala Pro Leu Leu Ile Arg Pro Tyr Leu Ala Asp Met Thr Leu Ser
                325                 330                 335

```
Glu Val His Val Val Met Thr Gly Gly Tyr Ala Thr Ile Ala Gly Ser
                340                 345                 350

Leu Leu Gly Ala Tyr Ile Ser Phe Gly Ile Asp Ala Thr Ser Leu Ile
            355                 360                 365

Ala Ala Ser Val Met Ala Ala Pro Cys Ala Leu Ala Leu Ser Lys Leu
        370                 375                 380

Val Tyr Pro Glu Val Glu Ser Lys Phe Arg Arg Glu Glu Gly Val
385                 390                 395                 400

Lys Leu Thr Tyr Gly Asp Ala Gln Ser Leu Ile Glu Ala Ala Ser Thr
                405                 410                 415

Gly Ala Ala Ile Ser Val Lys Val Val Ala Asn Ile Ala Ala Asn Leu
            420                 425                 430

Ile Ala Phe Leu Ala Val Leu Asp Phe Ile Asn Ala Ala Leu Ser Trp
        435                 440                 445

Leu Gly Asp Met Val Asp Ile Gln Gly Leu Ser Phe Gln Leu Ile Cys
    450                 455                 460

Ser Tyr Ile Leu Arg Pro Val Ala Phe Leu Met Gly Val Ala Trp Glu
465                 470                 475                 480

Asp Cys Pro Val Val Ala Glu Leu Leu Gly Ile Lys Leu Phe Leu Asn
                485                 490                 495

Glu Phe Val Ala Tyr Gln Asp Leu Ser Lys Tyr Lys Gln Arg Arg Leu
            500                 505                 510

Ala Gly Ala Glu Glu Trp Val Gly Asn Arg Lys Gln Trp Ile Ser Val
        515                 520                 525

Arg Ala Glu Val Leu Thr Thr Phe Ala Leu Cys Gly Phe Ala Asn Phe
    530                 535                 540

Ser Ser Ile Gly Ile Met Leu Gly Gly Leu Thr Ser Met Val Pro Gln
545                 550                 555                 560

Arg Lys Ser Asp Phe Ser Gln Ile Val Leu Arg Ala Leu Phe Thr Gly
                565                 570                 575

Ala Cys Val Ser Leu Val Asn Ala Cys Met Ala Gly Ile Leu Tyr Met
            580                 585                 590

Pro Arg Gly Ala Glu Val Asp Cys Met Ser Leu Leu Asn Thr Thr Leu
        595                 600                 605

Ser Ser Ser Ser Phe Glu Ile Tyr Gln Cys Cys Arg Glu Ala Phe Gln
    610                 615                 620

Ser Val Asn Pro Glu Phe Ser Pro Glu Ala Leu Asp Asn Cys Cys Arg
625                 630                 635                 640

Phe Tyr Asn His Thr Ile Cys Ala Gln
                645

(2) INFORMATION FOR SEQ ID NO:6:

(i) SEQUENCE CHARACTERISTICS:
        (A) LENGTH: 649 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Asn Asp Pro Ser Arg Arg Glu Ser Ile Ser Leu Thr Pro
1               5                   10                  15

Val Ala Lys Gly Leu Glu Asn Met Gly Ala Asp Phe Leu Glu Ser Leu
            20                  25                  30

Glu Glu Gly Gln Leu Pro Arg Ser Asp Leu Ser Pro Ala Glu Ile Arg
```

```
              35                  40                  45
Ser Ser Trp Ser Glu Ala Ala Pro Lys Pro Phe Ser Arg Trp Arg Asn
    50                  55                  60

Leu Gln Pro Ala Leu Arg Ala Arg Ser Phe Cys Arg Glu His Met Gln
65                  70                  75                  80

Leu Phe Arg Trp Ile Gly Thr Gly Leu Leu Cys Thr Gly Leu Ser Ala
                85                  90                  95

Phe Leu Leu Val Ala Cys Leu Leu Asp Phe Gln Arg Ala Leu Ala Leu
            100                 105                 110

Phe Val Leu Thr Cys Val Val Leu Thr Phe Leu Gly His Arg Leu Leu
            115                 120                 125

Lys Arg Leu Leu Gly Pro Lys Leu Arg Arg Phe Leu Lys Pro Gln Gly
130                 135                 140

His Pro Arg Leu Leu Leu Trp Phe Lys Arg Gly Leu Ala Leu Ala Ala
145                 150                 155                 160

Phe Leu Gly Leu Val Leu Trp Leu Ser Leu Asp Thr Ser Gln Arg Pro
                165                 170                 175

Glu Gln Leu Val Ser Phe Ala Gly Ile Cys Val Phe Ile Ala Leu Leu
            180                 185                 190

Phe Ala Cys Ser Lys His His Cys Ala Val Ser Trp Arg Ala Val Ser
            195                 200                 205

Trp Gly Leu Gly Leu Gln Phe Val Leu Gly Leu Leu Val Ile Arg Thr
210                 215                 220

Glu Pro Gly Phe Ile Ala Phe Glu Trp Leu Gly Glu Gln Ile Arg Ile
225                 230                 235                 240

Phe Leu Ser Tyr Thr Lys Ala Gly Ser Ser Phe Val Phe Gly Glu Ala
                245                 250                 255

Leu Val Lys Asp Val Phe Ala Phe Gln Val Leu Pro Ile Ile Val Phe
            260                 265                 270

Phe Ser Cys Val Ile Ser Val Leu Tyr His Val Gly Leu Met Gln Trp
            275                 280                 285

Val Ile Leu Lys Ile Ala Trp Leu Met Gln Val Thr Met Gly Thr Thr
290                 295                 300

Ala Thr Glu Thr Leu Ser Val Ala Gly Asn Ile Phe Val Ser Gln Thr
305                 310                 315                 320

Glu Ala Pro Leu Leu Ile Arg Pro Tyr Leu Ala Asp Met Thr Leu Ser
                325                 330                 335

Glu Val His Val Val Met Thr Gly Gly Tyr Ala Thr Ile Ala Gly Ser
            340                 345                 350

Leu Leu Gly Ala Tyr Ile Ser Phe Gly Ile Asp Ala Thr Ser Leu Ile
            355                 360                 365

Ala Ala Ser Val Met Ala Ala Pro Cys Ala Leu Ala Leu Ser Lys Leu
370                 375                 380

Val Tyr Pro Glu Val Glu Glu Ser Lys Phe Arg Arg Glu Glu Gly Val
385                 390                 395                 400

Lys Leu Thr Tyr Gly Asp Ala Gln Asn Leu Ile Glu Ala Ala Ser Thr
                405                 410                 415

Gly Ala Ala Ile Ser Val Lys Val Val Ala Asn Ile Ala Ala Asn Leu
            420                 425                 430

Ile Ala Phe Leu Ala Val Leu Asp Phe Ile Asn Ala Ala Leu Ser Trp
            435                 440                 445

Leu Gly Asp Met Val Asp Ile Gln Gly Leu Ser Phe Gln Leu Ile Cys
450                 455                 460
```

```
Ser Tyr Ile Leu Arg Pro Val Ala Phe Leu Met Gly Val Ala Trp Glu
465                 470                 475                 480

Asp Cys Pro Val Val Ala Glu Leu Leu Gly Ile Lys Leu Phe Leu Asn
                485                 490                 495

Glu Phe Val Ala Tyr Gln Asp Leu Ser Lys Tyr Lys Gln Arg Arg Leu
                500                 505                 510

Ala Gly Ala Glu Glu Trp Val Gly Asn Arg Lys Gln Trp Ile Ser Val
                515                 520                 525

Arg Ala Glu Val Leu Thr Thr Phe Ala Leu Cys Gly Phe Ala Asn Phe
530                 535                 540

Ser Ser Ile Gly Ile Met Leu Gly Gly Leu Thr Ser Met Val Pro Gln
545                 550                 555                 560

Arg Lys Ser Asp Phe Ser Gln Ile Val Leu Arg Ala Leu Phe Thr Gly
                565                 570                 575

Ala Cys Val Ser Leu Val Asn Ala Cys Met Ala Gly Ile Leu Tyr Met
                580                 585                 590

Pro Arg Gly Ala Glu Val Asp Cys Met Ser Leu Leu Asn Thr Thr Leu
                595                 600                 605

Ser Ser Ser Ser Phe Glu Ile Tyr Gln Cys Cys Arg Glu Ala Phe Gln
610                 615                 620

Ser Val Asn Pro Glu Phe Ser Pro Glu Ala Leu Asp Asn Cys Cys Arg
625                 630                 635                 640

Phe Tyr Asn His Thr Ile Cys Ala Gln
                645
```

(2) INFORMATION FOR SEQ ID NO:7:

(i) SEQUENCE CHARACTERISTICS:
        (A) LENGTH: 2400 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..2401

(xi) SEQUENCE DESCRIPTION: SEQ ID NO:7:

```
CCTGACGCTG CCTTCTCACT GCAGATAAGT GAGTAGTACA GGACCCTCTC CCCTCTCTAT      60

GCAGCCCTGT GTCTGTGAGT GCCCAGGGAG CAGGCATTTA CCAGGTCTGG TGGCTGCGTG     120

TCCACACGTC CTCATGAGGC TGAAGAGCCA AGCAC ATG GCA GAC AAC ACA CAG        173
                                       Met Ala Asp Asn Thr Gln
                                         1               5

AGC CAA AGA GAG TCC ATT TCC CTC ACG CCT ATG GCC CAC GGC CTG GAG       221
Ser Gln Arg Glu Ser Ile Ser Leu Thr Pro Met Ala His Gly Leu Glu
            10                  15                  20

AAC ATG GGG GCA GAA TTC CTG GAA AGC ATG GAG GAA GGC CGA CTC CCT       269
Asn Met Gly Ala Glu Phe Leu Glu Ser Met Glu Glu Gly Arg Leu Pro
                25                  30                  35

CAC AGT CAC TCA AGC CTG CCG GAG GGT GAA GGT GGC CTG AAC AAA GCA       317
His Ser His Ser Ser Leu Pro Glu Gly Glu Gly Gly Leu Asn Lys Ala
        40                  45                  50

GAG CGG AAG GCC TTC TCC CGA TGG AGG AGT CTG CAG CCG ACT GTG CAA       365
Glu Arg Lys Ala Phe Ser Arg Trp Arg Ser Leu Gln Pro Thr Val Gln
55                  60                  65                  70

GCG AGA AGC TTC TGC AGG GAG CAC CGG CAG CTG TTT GGA TGG ATC TGC       413
Ala Arg Ser Phe Cys Arg Glu His Arg Gln Leu Phe Gly Trp Ile Cys
                75                  80                  85
```

-continued

```
AAA GGC CTG CTC TCT ACT GCA TGT CTT GGC TTC TTG ATG GTC GCC TGC      461
Lys Gly Leu Leu Ser Thr Ala Cys Leu Gly Phe Leu Met Val Ala Cys
            90                  95                 100

CTC CTG GAC CTC CAG AGG GCC CTA GCA CTG TTG ATC ATC ACC TGT GTG      509
Leu Leu Asp Leu Gln Arg Ala Leu Ala Leu Leu Ile Ile Thr Cys Val
           105                 110                 115

GTT CTC GTC TTT CTG GCC TAT GAT CTG CTA AAG AGG CTT CTG GGG TCC      557
Val Leu Val Phe Leu Ala Tyr Asp Leu Leu Lys Arg Leu Leu Gly Ser
       120                 125                 130

AAG CTG AGG AGG TGT GTG AAG TTT CAA GGC CAT TCT TGC CTG AGC CTC      605
Lys Leu Arg Arg Cys Val Lys Phe Gln Gly His Ser Cys Leu Ser Leu
135                 140                 145                 150

TGG CTG AAA AGA GGT CTA GCC CTT GCT GCT GGT GTG GGC CTG ATC TTG      653
Trp Leu Lys Arg Gly Leu Ala Leu Ala Ala Gly Val Gly Leu Ile Leu
               155                 160                 165

TGG CTA TCT CTG GAC ACC GCC CAG CGG CCT GAA CAG CTG GTG TCC TTT      701
Trp Leu Ser Leu Asp Thr Ala Gln Arg Pro Glu Gln Leu Val Ser Phe
           170                 175                 180

GCA GGG ATC TGT GTG TTC CTT GTC CTT CTC TTT GCT GGC TCA AAG CAT      749
Ala Gly Ile Cys Val Phe Leu Val Leu Leu Phe Ala Gly Ser Lys His
       185                 190                 195

CAC CGT GCG GTG TCA TGG CGA GCT GTG TCC TGG GGC CTT GGG CTG CAG      797
His Arg Ala Val Ser Trp Arg Ala Val Ser Trp Gly Leu Gly Leu Gln
200                 205                 210

TTT GTG CTT GGG CTC TTC GTC ATC AGA ACA GAA CCA GGG TTC ATT GCA      845
Phe Val Leu Gly Leu Phe Val Ile Arg Thr Glu Pro Gly Phe Ile Ala
215                 220                 225                 230

TTC CAG TGG CTA GGG GAT CAG ATC CAG GTC TTC CTG AGT TAC ACC GAG      893
Phe Gln Trp Leu Gly Asp Gln Ile Gln Val Phe Leu Ser Tyr Thr Glu
               235                 240                 245

GCA GGC TCC AGC TTC GTC TTC GGA GAG GCT CTG GTG AAG GAT GTC TTT      941
Ala Gly Ser Ser Phe Val Phe Gly Glu Ala Leu Val Lys Asp Val Phe
           250                 255                 260

GCC TTT CAG GTT TTG CCC ATC ATC ATC TTC TTC AGC TGC GTC ATG TCT      989
Ala Phe Gln Val Leu Pro Ile Ile Ile Phe Phe Ser Cys Val Met Ser
       265                 270                 275

GTT CTG TAC TAT CTG GGC CTC ATG CAG TGG GTG ATC CTG AAG ATT GCC     1037
Val Leu Tyr Tyr Leu Gly Leu Met Gln Trp Val Ile Leu Lys Ile Ala
280                 285                 290

TGG TTG ATG CAG GTC ACC ATG GGC ACC TCA GCC ACC GAG ACA CTG AGT     1085
Trp Leu Met Gln Val Thr Met Gly Thr Ser Ala Thr Glu Thr Leu Ser
295                 300                 305                 310

GTG GCG GGA AAC ATC TTT GTG AGC CAG ACT GAA GCT CCT CTG CTG ATC     1133
Val Ala Gly Asn Ile Phe Val Ser Gln Thr Glu Ala Pro Leu Leu Ile
               315                 320                 325

CGG CCC TAT CTG GCA GAC ATG ACA CTC TCT GAA GTT CAC GTT GTC ATG     1181
Arg Pro Tyr Leu Ala Asp Met Thr Leu Ser Glu Val His Val Val Met
           330                 335                 340

ACT GGA GGC TAT GCT ACC ATT GCT GGC AGC CTC CTG GGC GCC TAC ATC     1229
Thr Gly Gly Tyr Ala Thr Ile Ala Gly Ser Leu Leu Gly Ala Tyr Ile
       345                 350                 355

TCC TTT GGG ATC GAC GCT GCT TCC TTA ATC GCA GCC TCT GTC ATG GCC     1277
Ser Phe Gly Ile Asp Ala Ala Ser Leu Ile Ala Ala Ser Val Met Ala
360                 365                 370

GCC CCT TGT GCG TTG GCT CTC TCC AAG CTG GTC TAC CCA GAG GTG GAG     1325
Ala Pro Cys Ala Leu Ala Leu Ser Lys Leu Val Tyr Pro Glu Val Glu
375                 380                 385                 390

GAG TCC AAG TTC CGG AGT GAG AAT GGC GTG AAG CTG ACC TAT GGA GAC     1373
Glu Ser Lys Phe Arg Ser Glu Asn Gly Val Lys Leu Thr Tyr Gly Asp
```

```
                395                 400                       405
GCT CAG AAC CTC TTG GAA GCA GCC AGT GCT GGG GCT GCC ATC TCA GTG         1421
Ala Gln Asn Leu Leu Glu Ala Ala Ser Ala Gly Ala Ala Ile Ser Val
            410                 415                 420

AAG GTC GTT GGC AAC ATT GCT GCC AAT CTG ATT GCC TTC CTG GCT GTA         1469
Lys Val Val Gly Asn Ile Ala Ala Asn Leu Ile Ala Phe Leu Ala Val
            425                 430                 435

CTA GCC TTC GTC AAT GCT GCC CTC TCC TGG CTA GGG GAC ATG GTG GAC         1517
Leu Ala Phe Val Asn Ala Ala Leu Ser Trp Leu Gly Asp Met Val Asp
            440                 445                 450

ATC CAG GGA CTC AGC TTC CAG CTC ATC TGC TCC TAC GTC CTG CGG CCT         1565
Ile Gln Gly Leu Ser Phe Gln Leu Ile Cys Ser Tyr Val Leu Arg Pro
455                 460                 465                 470

GTG GCC TTC TTG ATG GGT GTG GCC TGG GAG GAC TGT CCG GTA GTG GCT         1613
Val Ala Phe Leu Met Gly Val Ala Trp Glu Asp Cys Pro Val Val Ala
            475                 480                 485

GAG TTG CTG GGC ATC AAG TTC TTT CTG AAT GAG TTT GTG GCC TAT CAA         1661
Glu Leu Leu Gly Ile Lys Phe Phe Leu Asn Glu Phe Val Ala Tyr Gln
            490                 495                 500

GAG CTT TCC CAG TAC AAG CAA CGA CGC CTG GCA GGG GCT GAG GAG TGG         1709
Glu Leu Ser Gln Tyr Lys Gln Arg Arg Leu Ala Gly Ala Glu Glu Trp
            505                 510                 515

CTT GGT GAC AAG AAA CAG TGG ATC TCT GTC AGA GCA GAA ATC CTG ACT         1757
Leu Gly Asp Lys Lys Gln Trp Ile Ser Val Arg Ala Glu Ile Leu Thr
            520                 525                 530

ACA TAC GCC CTC TGT GGA TTT GCC AAC TTC AGC TCC ATC GGC ATC ATG         1805
Thr Tyr Ala Leu Cys Gly Phe Ala Asn Phe Ser Ser Ile Gly Ile Met
535                 540                 545                 550

TTG GGA GGC CTG ACC TCC CTA GTC CCC CAG CGG AGG AGC GAC TTC TCC         1853
Leu Gly Gly Leu Thr Ser Leu Val Pro Gln Arg Arg Ser Asp Phe Ser
            555                 560                 565

CAG ATT GTA CTC CGG GCA CTG ATC ACA GGG GCT TTC GTG TCC CTG CTA         1901
Gln Ile Val Leu Arg Ala Leu Ile Thr Gly Ala Phe Val Ser Leu Leu
            570                 575                 580

AAC GCC TGT GTG GCA GGG ATC CTC TAT GTA CCC AGG GGG GTC GAG GTG         1949
Asn Ala Cys Val Ala Gly Ile Leu Tyr Val Pro Arg Gly Val Glu Val
            585                 590                 595

GAC TGC GTG TCC CTT CTG AAC CAA ACT GTC AGC AGC AGC AGC TTT GAG         1997
Asp Cys Val Ser Leu Leu Asn Gln Thr Val Ser Ser Ser Ser Phe Glu
            600                 605                 610

GTT TAC CTG TGC TGC CGC CAA GTC TTC CAG AGC ACT AGC TCG GAG TTC         2045
Val Tyr Leu Cys Cys Arg Gln Val Phe Gln Ser Thr Ser Ser Glu Phe
615                 620                 625                 630

AGC CAA GTG GCA CTG GAC AAC TGC TGT CGA TTT TAC AAC CAC ACA GTC         2093
Ser Gln Val Ala Leu Asp Asn Cys Cys Arg Phe Tyr Asn His Thr Val
            635                 640                 645

TGC ACA TA GCTGGGACGG AGCATCTTCC TAGCCTCAGG GCTCATCCAG                  2141
Cys Thr

CCCAGAGAGG CCGTGGGACT CGTCACTACC TCCATCCCAC AATTGGGAAG GGTGCAACGG       2201

TCATCGCTGC TCCCATGTCT GCCTCTCCAA GTACGAGTTC CCAGAGTCTG GTCTGCTCTC       2261

CTGCCCTTTG GGAGCCAACA TTCTGGTCCT CTTGAGTCCT CTTTCCTTGG GAACCTCATG       2321

TGCACCAGCC AAAAGCCTCC TCCCTGCTCC CTCCCAAGCA CCCAGCTTGT TGGGTATCCC       2381

CCCAAAAGCT GTCTCTAGA                                                    2400
```

(2) INFORMATION FOR SEQ ID NO:8:

(i) SEQUENCE CHARACTERISTICS:

(A) LENGTH: 648 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Asp Asn Thr Gln Ser Gln Arg Glu Ser Ile Ser Leu Thr Pro
 1               5                  10                  15

Met Ala His Gly Leu Glu Asn Met Gly Ala Glu Phe Leu Glu Ser Met
                20                  25                  30

Glu Glu Gly Arg Leu Pro His Ser His Ser Ser Leu Pro Glu Gly Glu
            35                  40                  45

Gly Gly Leu Asn Lys Ala Glu Arg Lys Ala Phe Ser Arg Trp Arg Ser
    50                  55                  60

Leu Gln Pro Thr Val Gln Ala Arg Ser Phe Cys Arg Glu His Arg Gln
65                  70                  75                  80

Leu Phe Gly Trp Ile Cys Lys Gly Leu Leu Ser Thr Ala Cys Leu Gly
                85                  90                  95

Phe Leu Met Val Ala Cys Leu Leu Asp Leu Gln Arg Ala Leu Ala Leu
               100                 105                 110

Leu Ile Ile Thr Cys Val Val Leu Val Phe Leu Ala Tyr Asp Leu Leu
           115                 120                 125

Lys Arg Leu Leu Gly Ser Lys Leu Arg Arg Cys Val Lys Phe Gln Gly
       130                 135                 140

His Ser Cys Leu Ser Leu Trp Leu Lys Arg Gly Leu Ala Leu Ala Ala
145                 150                 155                 160

Gly Val Gly Leu Ile Leu Trp Leu Ser Leu Asp Thr Ala Gln Arg Pro
               165                 170                 175

Glu Gln Leu Val Ser Phe Ala Gly Ile Cys Val Phe Leu Val Leu Leu
           180                 185                 190

Phe Ala Gly Ser Lys His His Arg Ala Val Ser Trp Arg Ala Val Ser
       195                 200                 205

Trp Gly Leu Gly Leu Gln Phe Val Leu Gly Leu Phe Val Ile Arg Thr
210                 215                 220

Glu Pro Gly Phe Ile Ala Phe Gln Trp Leu Gly Asp Gln Ile Gln Val
225                 230                 235                 240

Phe Leu Ser Tyr Thr Glu Ala Gly Ser Ser Phe Val Phe Gly Glu Ala
               245                 250                 255

Leu Val Lys Asp Val Phe Ala Phe Gln Val Leu Pro Ile Ile Ile Phe
           260                 265                 270

Phe Ser Cys Val Met Ser Val Leu Tyr Tyr Leu Gly Leu Met Gln Trp
       275                 280                 285

Val Ile Leu Lys Ile Ala Trp Leu Met Gln Val Thr Met Gly Thr Ser
290                 295                 300

Ala Thr Glu Thr Leu Ser Val Ala Gly Asn Ile Phe Val Ser Gln Thr
305                 310                 315                 320

Glu Ala Pro Leu Leu Ile Arg Pro Tyr Leu Ala Asp Met Thr Leu Ser
               325                 330                 335

Glu Val His Val Val Met Thr Gly Gly Tyr Ala Thr Ile Ala Gly Ser
           340                 345                 350

Leu Leu Gly Ala Tyr Ile Ser Phe Gly Ile Asp Ala Ala Ser Leu Ile
       355                 360                 365

Ala Ala Ser Val Met Ala Ala Pro Cys Ala Leu Ala Leu Ser Lys Leu
370                 375                 380

```
Val Tyr Pro Glu Val Glu Ser Lys Phe Arg Ser Glu Asn Gly Val
385                 390                 395                 400

Lys Leu Thr Tyr Gly Asp Ala Gln Asn Leu Leu Glu Ala Ala Ser Ala
            405                 410                 415

Gly Ala Ala Ile Ser Val Lys Val Val Gly Asn Ile Ala Ala Asn Leu
                420                 425                 430

Ile Ala Phe Leu Ala Val Leu Ala Phe Val Asn Ala Ala Leu Ser Trp
        435                 440                 445

Leu Gly Asp Met Val Asp Ile Gln Gly Leu Ser Phe Gln Leu Ile Cys
    450                 455                 460

Ser Tyr Val Leu Arg Pro Val Ala Phe Leu Met Gly Val Ala Trp Glu
465                 470                 475                 480

Asp Cys Pro Val Val Ala Glu Leu Leu Gly Ile Lys Phe Phe Leu Asn
                485                 490                 495

Glu Phe Val Ala Tyr Gln Glu Leu Ser Gln Tyr Lys Gln Arg Arg Leu
                500                 505                 510

Ala Gly Ala Glu Glu Trp Leu Gly Asp Lys Lys Gln Trp Ile Ser Val
            515                 520                 525

Arg Ala Glu Ile Leu Thr Thr Tyr Ala Leu Cys Gly Phe Ala Asn Phe
    530                 535                 540

Ser Ser Ile Gly Ile Met Leu Gly Gly Leu Thr Ser Leu Val Pro Gln
545                 550                 555                 560

Arg Arg Ser Asp Phe Ser Gln Ile Val Leu Arg Ala Leu Ile Thr Gly
                565                 570                 575

Ala Phe Val Ser Leu Leu Asn Ala Cys Val Ala Gly Ile Leu Tyr Val
            580                 585                 590

Pro Arg Gly Val Glu Val Asp Cys Val Ser Leu Leu Asn Gln Thr Val
        595                 600                 605

Ser Ser Ser Ser Phe Glu Val Tyr Leu Cys Cys Arg Gln Val Phe Gln
        610                 615                 620

Ser Thr Ser Ser Glu Phe Ser Gln Val Ala Leu Asp Asn Cys Cys Arg
625                 630                 635                 640

Phe Tyr Asn His Thr Val Cys Thr
                645
```